US009963699B2

(12) United States Patent
Bennett et al.

(10) Patent No.: US 9,963,699 B2
(45) Date of Patent: May 8, 2018

(54) METHODS FOR MODULATING C9ORF72 EXPRESSION

(71) Applicants: Ionis Pharmaceuticals, Inc., Carlsbad, CA (US); Ludwig Institute for Cancer Research, New York, NY (US); The Regents of the University of California, Oakland, CA (US)

(72) Inventors: C. Frank Bennett, Carlsbad, CA (US); Susan M. Freier, San Diego, CA (US); Frank Rigo, Carlsbad, CA (US); Don W. Cleveland, Del Mar, CA (US); Clotilde Lagier-Tourenne, La Jolla, CA (US); John M. Ravits, La Jolla, CA (US); Michael W. Baughn, La Jolla, CA (US)

(73) Assignees: Ionis Pharmaceuticals, Inc., Carlsbad, CA (US); Ludwig Institute for Cancer Research, New York, NY (US); The Regents of the University of California, Oakland, CA (US)

( * ) Notice: Subject to any disclaimer, the term of this patent is extended or adjusted under 35 U.S.C. 154(b) by 0 days. days.

(21) Appl. No.: 14/436,030

(22) PCT Filed: Oct. 15, 2013

(86) PCT No.: PCT/US2013/065067
§ 371 (c)(1),
(2) Date: Apr. 15, 2015

(87) PCT Pub. No.: WO2014/062686
PCT Pub. Date: Apr. 24, 2014

(65) Prior Publication Data
US 2015/0267197 A1    Sep. 24, 2015

Related U.S. Application Data

(60) Provisional application No. 61/714,139, filed on Oct. 15, 2012.

(51) Int. Cl.
*C12N 15/113* (2010.01)
(52) U.S. Cl.
CPC ........ *C12N 15/113* (2013.01); *C12N 2310/11* (2013.01); *C12N 2310/14* (2013.01); *C12N 2310/315* (2013.01); *C12N 2310/3181* (2013.01); *C12N 2310/3231* (2013.01); *C12N 2310/3233* (2013.01); *C12N 2310/3341* (2013.01); *C12N 2310/341* (2013.01)

(58) Field of Classification Search
CPC . C12N 15/111; C12N 15/113; C12N 2310/11; C12N 2310/341
See application file for complete search history.

(56) References Cited

U.S. PATENT DOCUMENTS

| 5,801,154 | A |   | 9/1998  | Baracchini et al. |
|-----------|---|---|---------|-------------------|
| 5,998,148 | A | * | 12/1999 | Bennett ................ C12N 15/113 435/325 |
| 6,268,490 | B1|   | 7/2001  | Imanishi et al.   |
| 6,525,191 | B1|   | 2/2003  | Ramasamy          |
| 6,582,908 | B2|   | 6/2003  | Fodor et al.      |
| 6,670,461 | B1| * | 12/2003 | Wengel ................ C07H 21/00 536/22.1 |
| 6,770,748 | B2|   | 8/2004  | Imanishi et al.   |
| 6,794,499 | B2|   | 9/2004  | Wengel et al.     |
| 7,034,133 | B2|   | 4/2006  | Wengel et al.     |
| 7,053,207 | B2|   | 5/2006  | Wengel            |
| 7,399,845 | B2|   | 7/2008  | Seth et al.       |
| 7,427,672 | B2|   | 9/2008  | Imanishi et al.   |
| 7,547,684 | B2|   | 6/2009  | Seth et al.       |
| 7,696,345 | B2|   | 4/2010  | Allerson et al.   |
| 8,501,805 | B2|   | 8/2013  | Seth et al.       |
| 8,530,640 | B2|   | 9/2013  | Seth et al.       |
| 8,546,556 | B2|   | 10/2013 | Seth et al.       |
| 9,012,421 | B2|   | 4/2015  | Migawa et al.     |
| 2001/0053519 | A1 |   | 12/2001 | Fodor et al.    |
| 2003/0228597 | A1 |   | 12/2003 | Cowsert et al.  |

(Continued)

FOREIGN PATENT DOCUMENTS

| EP | 1752536 | 2/2007 |
| WO | WO 1998/039352 | 9/1998 |

(Continued)

OTHER PUBLICATIONS

Bieniek et al., "Tau pathology in frontotemporal lobar degeneration with C9ORF72 hexanucleotide repeat expansion" (2013) 125(2):289-302.

(Continued)

*Primary Examiner* — J. E. Angell
(74) *Attorney, Agent, or Firm* — McNeil Baur PLLC

(57) ABSTRACT

Disclosed herein are methods for reducing expression of C9ORF72 mRNA and protein in an animal with C9ORF72 specific inhibitors. Such methods are useful to treat, prevent, or ameliorate neurodegenerative diseases in an individual in need thereof. Such C9ORF72 specific inhibitors include antisense compounds. Examples of neurodegenerative diseases that can be treated, prevented, and ameliorated with the administration C9ORF72 specific inhibitors include amyotrophic lateral sclerosis (ALS), frontotemporal dementia (FTD), corticalbasal degeneration syndrome (CBD), atypical Parkinsonian syndrome, and olivopontocerellar degeneration (OPCD).

28 Claims, No Drawings

(56) References Cited

U.S. PATENT DOCUMENTS

| | | |
|---|---|---|
| 2004/0171570 A1 | 9/2004 | Allerson et al. |
| 2004/0181048 A1 | 9/2004 | Wang |
| 2005/0130923 A1 | 6/2005 | Bhat et al. |
| 2007/0031844 A1 | 2/2007 | Khvorova et al. |
| 2008/0039618 A1 | 2/2008 | Allerson et al. |
| 2009/0012281 A1 | 1/2009 | Swayze et al. |
| 2010/0216864 A1 | 8/2010 | Staarup et al. |
| 2012/0149757 A1 | 6/2012 | Krainer et al. |
| 2012/0214865 A1 | 8/2012 | Bennett et al. |
| 2013/0035366 A1 | 2/2013 | Swayze et al. |
| 2014/0255936 A1 | 9/2014 | Rademakers |
| 2014/0303238 A1* | 10/2014 | Linsley .............. C07H 21/04 514/44 A |
| 2015/0148404 A1 | 5/2015 | de Visser et al. |
| 2015/0251655 A1 | 9/2015 | Lakehal-Ayat et al. |
| 2015/0259679 A1 | 9/2015 | Bennett et al. |
| 2016/0024496 A1 | 1/2016 | Bennett et al. |
| 2016/0108396 A1 | 4/2016 | Jensen et al. |
| 2016/0251656 A1 | 9/2016 | Freier et al. |
| 2016/0304871 A1 | 10/2016 | Rigo |

FOREIGN PATENT DOCUMENTS

| | | |
|---|---|---|
| WO | WO 1999/014226 | 3/1999 |
| WO | WO 2003/004602 | 1/2003 |
| WO | WO 2004/106356 | 12/2004 |
| WO | WO 2005/021570 | 3/2005 |
| WO | WO 2005/040180 | 5/2005 |
| WO | WO 2007/134181 | 11/2007 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2011/135396 | 11/2011 |
| WO | WO 2012/012467 | 1/2012 |
| WO | WO 2012/092367 | 7/2012 |
| WO | WO 2013/030588 | 3/2013 |
| WO | WO 2013/086207 | 6/2013 |
| WO | WO 2014/062686 | 4/2014 |
| WO | WO 2014/062691 | 4/2014 |
| WO | WO 2014/062736 | 4/2014 |
| WO | WO 2014/114660 | 7/2014 |
| WO | WO 2015/054676 | 4/2015 |
| WO | WO 2016/024205 | 2/2016 |
| WO | WO 2016/060919 | 4/2016 |
| WO | WO 2016/168592 | 10/2016 |

OTHER PUBLICATIONS

Donnelly et al., "Limited availability of ZBP1 restricts axonal mRNA localization and nerve regeneration capacity" EMBO J. (2011) 30:4665-4677.

Donnelly et al., "RNA toxicity from the ALS/FTD C9ORF72 expansion is mitigated by antisense intervention" (2013) 80(2):415-428.

International Search Report for application No. PCT/US2013/065073 dated Apr. 22, 2014.

International Search Report for application PCT/US2013/065131 dated Feb. 14, 2014.

Jeong et al., "Rapid Identification of Monospecific Monoclonal Antibodies Using a Human Proteome Microarray." Mol. Cell. Proteomics (2012) 11(6): O111.016253-1 to O111.016253-10.

Klein et al., "Gain of RNA function in pathological cases: Focus on myotonic dystrophy" Biochimie (2011) 93(11):2006-2012.

Lagier-Tourenne et al., "Targeted Degradation of Sense and Antisense C9ORF72 RNA Foci as Therapy for ALS and Frontotemporal Degeneration" PNAS (2013) 1-10.

Madson, "Antisense Against C9ORF72", http://alsn.mda.org/article/antisense-against-c9orf72 (printed Oct. 28, 2015).

Mulders et al., "Triplet-repeat oligonucleotide-mediated reversal of RNA toxicity in myotonic dystrophy" (2009) 106(33):13915-13920.

Rabin et al., "Sporadic ALS has compartment-specific aberrant exon splicing and altered cell-matrix adhesion biology" Hum Mol Genet. (2010) 19(2):313-328.

"The ALS Association and the Packard Center Partner to Develop Animal Model Systems for Most Common Cause of Familial ALS", http://www.alsa.org/news/archive/new-animal-model-systems.html (printed Oct. 23, 2015).

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.

Altmann et al., "Second Generation Antisense Oligonucleotides-Inhibition of PKC-α and c-raf Kinase Expression by Chimeric Oligonucleotides Incorporating 6"-Substituted Carbocyclic Nucleosides and 2"-O-Ethylene Glycol Substituted Ribonucleosides" Nuclewsodies Nucleotides. (1997) 16:917-926.

Altmann et al., "Second Generation of Antisense Oligonucleotides: From Nuclease Resistance to Biological Efficacy in Animals" Chimia. (1996) 50(4):168-176.

Altmann et al., "Second-generation antisense oligonucleotides: structure-activity relationships and the design of improved signal-transduction inhibitors" Biochem. Soc. Trans. (1996) 24:630-637.

Altschul et al., "Basic Local Alignment Search Tool" J. Mol. Biol. (1990) 215:403-410.

Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272:11994-12000.

Boxer et al. "Clinical, neuroimaging and neuropathological features of a new chromosome 9p-linked FTD-ALS family" J. Neurol. Neurosurg. Psychiatry (2011) 82:196-203.

Braasch et al., "Locked nucleic acid (LNA): fine-tuning the recognition of DNA and RNA" Chem. Biol. (2001) 8:1-7.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Chio et al., "Prevalence of SOD1 mutations in the Italian ALS population" Neurology (2008) 70:533-537.

Crooke et al., "Basic Principles of Antisense Therapeutics" Antisense Research and Application (1998) Chapter 1:1-50.

Dejesus-Hernandez et al., "Expanded GGGGCC Hexanucleotide Repeat in Noncoding Region of C9ORF72 Causes Chromosome 9p-Linked FTD and ALS" Neuron (2011) 72:245-256.

Elayadi et al., "Application of PNA and LNA oligomers to chemotherapy" Curr. Opinion Invens. Drugs (2001) 2:558-561.

Freier et al., "The ups and downs of nucleic acid duplex stability: structure-stability studies on chemically-modified DNA:RNA duplexes" Nucleic Acids Research (1997) 25(22):4429-4443.

Frieden et al., "Expanding the design horizon of antisense oligonucleotides with alpha-L-LNA" Nucleic Acids Research (2003) 31(21):6365-6372.

Gautschi et al., "Activity of a novel bcl-2/bcl-xLbispecific antisense oligonucleotide against tumors of diverse histologic origins" J. Natl. Cancer Inst. (2001) 93:463-471.

Hirtz et al., "How common are the "common" neurologic disorders?" Neurology (2007) 68:326-337.

International Search Report for application PCT/US13/65067 dated Jan. 24, 2014.

Johnson et al., "Exome sequencing reveals VCP mutations as a cause of familial ALS" Neuron (2010) 68:857-864.

Jones et al., "RNA quantitation by fluorescence-based solution assay: RiboGreen reagent characterization" Analytical Biochemistry (1998) 265(2):368-374.

Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.

(56) References Cited

OTHER PUBLICATIONS

Kumar et al., "The first analogues of LNA (locked nucleic acids): phosphorothioate-LNA and 2'-thio-LNA" Bioorg Med Chem Lett. (1998) 8:2219-2222.

Kwiatkowski et al., "Mutations in the FUS/TLS gene on chromosome 16 cause familial amyotrophic lateral sclerosis" Science (2009) 323:1205-1208.

Laaksovirta et al, "Chromosome 9p21 in amyotrophic lateral sclerosis in Finland: a genome-wide association study" Lancet Neurol. (2010) 9:978-985.

Leumann et al., "DNA Analogues: From Supramolecular Principles to Biological Properties" Bioorganic & Medicinal Chemistry (2002) 10:841-854.

Lillo et al., "Frontotemporal dementia and motor neurone disease: overlapping clinic-pathological disorders" J. Clin. Neurosci. (2009) 16:1131-1135.

Maher et al., "Comparative hybrid arrest by tandem antisense oligodeoxyribonucleotides or oligodeoxyribonucleoside methylphosphonates in a cell-free system" Nucl. Acid. Res. (1998) 16(8):3341-3358.

Margolis et al., "DM2 intronic expansions: evidence for CCUG accumulation without flanking sequence or effects on ZNF9 mRNA processing or protein expression" Hum. Mol. Genet. (2006) 15:1808-1815.

Martin, "New acces to 2'-O-alkylated ribonucleosides and properties of 2'-O-alkylated oligoribonucleotides" Helv. Chim. Acta. (1995) 78:486-504.

Maruyama et al., "Mutations of optineurin in amyotrophic lateral sclerosis" Nature (2010) 465:223-226.

Morita et al., "A locus on chromosome 9p confers susceptibility to ALS and frontotemporal dementia" Neurology (2006) 66:839-844.

Neumann et al., "Ubiquitinated TDP-43 in frontotemporal lobar degeneration and amyotrophic lateral sclerosis" Science (2006) 314:130-133.

New England Biolabs 1998/99 Catalog (cover page and pp. 121 and 284).

Orum et al., "Locked nucleic acids: A promising molecular family for gene-function analysis and antisense drug development" Curr. Opinion Mol. Ther. (2001) 3:239-243.

Pearson et al., "Familial frontotemporal dementia with amyotrophic lateral sclerosis and a shared haplotype on chromosome 9p" J. Nerol. (2011) 258:647-655.

Renton et al., "A Hexanucleotide Repeat Expansion in C9ORF72 is the Cause of Chromosome 9p21-Linked ALS-FTD" Neuron (2011) 72:257-268.

Reynolds et al., "Rational siRNA design for RNA interference" Nature Biotechnology (2004) 22(3):326-330.

Rosen et al., "Mutations in Cu/Zn superoxide dismutase gene are associated with familial amyotrophic lateral sclerosis" Nature (1993) 362:59-62.

Rowland et al., "Amyotrophic lateral sclerosis" N. Engl. J. Med. (2001) 344(22):1688-1700.

Sanghvi et al., "Heterocyclic Base Modifications in Nucleic Acids and Their Applications in Antisense Oligonucleotides" Antisense Research and Applications (1993) pp. 273-288.

Singh et al., "LNA (locked nucleic acids): synthesis and high-affinity nucleic acid recognition" Chem. Commun. (1998) 455-456.

Singh et al., "Synthesis of 2'-amino-LNA: A novel conformationally restricted high-affinity oligonucleotide analogue with a handle" J. Org. Chem. (1998) 63: 10035-10039.

Smith et al., "Comparison of biosequences" Adv. Appl. Math. (1981) 2(4):482-489.

Sreedharan et al., "TDP-43 mutations in familial and sporadic amyotrophic lateral sclerosis" Science (2008) 319:1668-1672.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.

Vance et al., "Familial amyotrophic lateral sclerosis with frontotemporal dementia is linked to a locus on chromosome 9p13.2-21.3" Brain (2006) 129:868-876.

Wahlestedt et al., "Potent and nontoxic antisense oligonucleotide containing locked nucleic acids" Proc. Natl. Acad. Sci. USA (2000) 97: 5633-5638.

Woolf et al., "Specificity of antisense oligonucleotides in vivo" PNAS (1992) 89: 7305-7309.

Zhang et al., "PowerBLAST: A New Network BLAST Application for Interactive or Automated Sequence Analysis and Annotation" Genome Res. (1997) 7:649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

Al-Sarraj et al., "p62 positive, TDP-43 negative, neuronal cytoplasmic and intranuclear inclusions in the cerebellum and hippocampus define the pathology of C9orf72-linked FTLD and MND/ALS" Acta Neuropathol (2011) 122:691-702.

Baloh, R.H, "Generation of Non-Integrating iPS Cells and Motor Neurons from C9orf72 Repeat Expansion ALS Patients" 65th AAN Annual Meeting, San Diego, CA, Mar. 16-23, 2013.

Baloh, R.H., "Targeting RNA foci shows a therapeutic effect in iPSC-derived motor neurons from C9orf72 repeat patients" ALSMND meeting, Milan, Dec. 6, 2013.

Baloh, R.H., "Induced Pluripotent stem cell models from C9orf72 patients." Oral presentation, California ALS PAC 10 Research Summit, Los Angeles, CA, Nov. 11, 2012.

Baughn et al., "Antisense Oligonucleotide as a Potential Therapy for Amyotrophic Lateral Sclerosis with C9orf72 Expansion" Poster Presentation, Keystone Symposia, New Frontiers in Neurodegenerative Disease Research, Santa Fe, NM, Feb. 3-8, 2013.

Baughn et al, "Sense and Anti-Sense RNA Foci in c9ALS/FTD: More Light in a House of Mirrors" Annals of Neurology (Dec. 2013) 74(17): p. S60.

Brettschneider et al., "Microglial activation correlates with disease progression and upper motor neuron clinical symptoms in Amyotrophic Lateral Sclerosis", Plos One (2012) 7:e39216.

Donnelly et al., "Development of a C9ORF72 ALS antisense therapy and a therapeutic biomarker" Abstracts of the Society for Neuroscience, Washington, DC, US, Oct. 17, 2012, Retrieved from the Internet Aug. 15, 2016: http://www.abstractsonline.com/Plan/ViewAbstract.aspx?sKey=c4cccfd5-5e4c-4dle-9569-9albleb21d80&cKey=c5c69155-5d2b-467c-8d1f-87299c514c7f&mKey=%7b70007181-01C9-4DE9-A0A2-EEBFA14CD9F1%7d.

Donnelly et al., "Development of C9ORF72 ALS Biomarkers and Therapeutics" American Neurological Association 2012 Annual Meeting, Poster Presentation, Boston, MA Oct. 10, 2012.

Donnelly et al., "Development of C9orf72 ALS Biomarkers and Therapeutics" Annals of Neuology (Oct. 10, 2012) 72(16):S67-S68.

Donnelly et al., "Transcriptome analysis of C9orf72 ALS patient derived CNS iPS cells and autopsy tissue reveals a unique expression and splicing profile." Abstracts of the Society for Neuroscience, Washington, DC, US, Oct. 16, 2012, Retrieved from the Internet Aug. 19, 2016: http://www.abstractsonline.com/Plan/ViewAbstract.aspx?sKey=99bd542e-9dff-4338-9756-dfbeb1839aa6&cKey=63d1b086-9f01-43d4-ab3f-d258faa86d9e&mKey=%7b70007181-01C9-4DE9-A0A2-EEBFA14CD9F1%7d.

Donnelly et al., "Transcriptome analysis of C9orf72 ALS patient derived CNS iPS cells and autopsy tissue reveals a unique expression and splicing profile." Oral Presentation, Neuroscience 2012, Washington, DC, US, Oct. 17, 2012.

European Search Report for application No. 13847957.1 dated Jul. 13, 2016.

European Search Report for application No. 13846313.8 dated May 11, 2016.

European Search Report for application No. 13847099.2 dated May 25, 2016.

File History of U.S. Appl. No. 14/436,024, filed Apr. 15, 2015.

File History of U.S. Appl. No. 14/436,039, filed Apr. 15, 2015.

(56) References Cited

OTHER PUBLICATIONS

Ganesalingam et al., "Combination of neurofiliment heavy chain and complement C3 as CSF biomarkers for ALS" Journal of Neurochemistry (2011) 117: 528-537.
Ince et al., "Molecular pathology and genetic advances in amyotrophic lateral sclerosis: an emerging molecular pathway and the significance of glial pathology," Acta Neuro. (2011) 122:657-671.
Jiang et al., "Antisense oligonucleotide therapy for ALS/FTD caused by a gain of toxicity from C9orf72 hexanucleotide expansions." Poster Presentation, 10th Brain Research Conference, RNA Metabolism in Neurological Disease, Oct. 16, 2015.
Jiang et al. "Gain of Toxicity from ALS/FTG-Linked Repeat Expansions in C9ORF72 is Alleviated by Antisense Oligonucleotides Targeting GGGCC-Containing RNAs." Neuron (2016) 90:535-550.
Lagier-Tourenne, et al., "Sense and Antisense RNA Foci in C9-ALS/FTD: More Light in a House of Mirrors." Poster Presentation, American Neurological Association 2013 Annual Meeting; Oct. 14, 2013.
Lagier-Tourenne, C., "Targeted degradation of sense and antisense C9orf72 nuclear foci as therapy for ALS and FTD" Oral Presentation, 24th International Symposium on ALS/MND, Milan, Dec. 6, 2013.
Lagier-Tourenne, C., "Identifying mechanisms and therapy for ALS/FTD from C9orf72 expansion", Oral Presentation, ALSA and AFTD Symposium, Society for Neuroscience Annual Meeting, New Orleans; Oct. 15, 2012.
Lagier-Tourenne, C. "Therapy Development for ALS/MND and Frontotemporal Dementia with C9orf72 Expansion: Antisense Oligonucleotide Mediated Reduction in Nuclear RNA Foci." ALS FD (Nov. 4, 2013) 14(sup2): p. 17.
Lindquist et al, "Corticobasal and ataxia syndromes widen the spectrum of C9ORF72 hexanucleotide expansion disease." Clin Genet (2013) 83:279-283.
O'Rourke et al., "C9orf72 BAC Transgenic Mice Display Typical Pathologic Features of ALS/FTD." Neuron (2015) 88(5):892-901.
Ostrow et al., "The C9orf72 ALS mutation causes both increased expression and aberrant splicing og the endothelin-B receptor, and its ligand endothelin-1 is increased in CNS tissue from ALS patients and mutant mice," Abstracts of the Society for Neuroscience (Oct. 17, 2012) 42: p. 1.
Ravits, J., "Expanding Neurodegeneration: C9orf72-ALS/FTD" Oral Presentation, ANA Meeting, New Orleans, LA, (Oct. 15, 2013).
Ravits. J., "Regional Spread in ALS: Mechanisms and Pathogenesis." Oral Presentation, 2nd Annual Neuromuscular Colloquium, UC Irvine, Newport Beach, CA, May 4, 2012.
Riboldi et al., "Antisense Oligonucleotide Therapy for the Treatment of C9ORF72 ALS/FTD Diseses." Mol Neurobiol (2014) 50:721-732.
Rigo, F., "ASO therapy for ALS and FTD caused by a gain of toxicity from hexanucleotide expansion in the C9orf72 gene." Oral Presentation, OTS Annual Meeting, Leiden, the Netherlands; Oct. 11-14, 2015.
Sareen, et al., "Targeting RNA foci shows a therapeutic effect in iPSC-derived motor neurons from C9orf72 repeat patients." ALS FD (Nov. 4, 2013) 14(sup2): pp. 16-17.
Sareen et al., "Targeting RNA foci in iPSC-derived motor neurons from ALS patients with a C9ORF72 repeat expansion." Sci Tran Med (2013) 5(208): 1-13.
Simon-Sanchez et al., "The clinical and pathological phenoype of C9OFR72 hexanucleotide repeat expansions", Brain: Journal of Neurology (2012) 135:723-735.
Todd et al. "RNA mediated neurodegeneration in repeat expansion disorders," Annals of Neruology (2009) 67(3):291-300.
Wojciechowska et al., "Cellular toxicity of expanded RNA repeats: focus on RNA foci" Human Molecular Genetics (2011) 1-11.
Zhang et al., "The C9orf72 repeat expansion disrupts nucleocytoplasmic transport." Nature (2015) 525(7567):56-61.
File History of U.S. Appl. No. 15/028,626, filed Apr. 11, 2016.
File History of U.S. Appl. No. 15/130,818, filed Apr. 15, 2016.
International Search Report for application on. PCT/US2014/060194 dated Apr. 14, 2015.
Nelson et al., "The unstable repeats—three evolving faces of neurological disease." Neuron (2013) 77(5):825-43.
GenBank: JU333328.1 TSA: Macaca mulatta Mamu_527777 mRNA sequence. Mar. 26, 2012 (Retrieved from the internet Sep. 12, 2016: http://www.ncbi.nlm.nih.gov/nuccore/380810415?sat=18 &satkey=24474174).
"The ALS Association and the Packard Center Partner to Develop Animal Model Systems for Most Common Cause of Familial ALS", http://www.alsa.org/news/archive/new-animal-model-systems.html Mar. 1, 2012 (printed Oct. 23, 2015).
Baughn et al, "Sense and Anti-Sense RNA Foci in c9ALS/FTD: More Light in a House of Mirrors" Annals of Neurology (Oct. 14, 2013) 74(17): p. S60.
Madson, "Antisense Against C9ORF72", http://alsn.mda.org/article/antisense-against-c90rf72 Jul. 1, 2012 (printed Oct. 28, 2015).
Ash et al., "Unconventional Translation of C9ORF72 GGGGCC Expansion Generates Insoluble Ploypeptides Specific to c9FTD/ALS" Neuron (2013) 77(4): 639-646.
Extended European Search Report for application No. 14852924.1 dated Jun. 20, 2017.
Fernandes et al., "Oligonucleotide-Based Therapy for FTD/ALS Caused by the C9ORF72 Repeat Expansion: A Perspective," Journal of Nucleic Acids, 2013, 1-11.
Gendron et al., "Poly(GP) Proteins are a Useful Pharmacodynamic Marker for C9ORF72-Associated Amyotrophic Lateral Sclerosis," Sci Tran Med, 2017, 9(383):1-12.
International Search Report and Written Opinion for PCT/US2016/027747, dated Sep. 30, 2016, 12 pages.
Lee et al., "Antisense Therapy in Neurology," Journal of Personalized Medicine, 2013, 3(3):144-176.
Sha et al., "Treatment Implications of C9ORF72," Alzheimers Res Ther, 2012, 4(6):46, 7 pages.
Thomsen, "Dramatically Improved RNA in 1-15 Situ Hybridization Signals Using LNA-Modified Probes," RNA, 2005, 11(11):1745-1748.
International Search Report for application No. PCT/US17/27355 dated Jul. 26, 2017.
Mahoney et al., "Frontotemporal dementia with the C9ORF72 hexanucleotide repeat expansion: clinical, neuroanatomical and neuropathological features" Brain (2012) 135: 736-750.

* cited by examiner

SEQUENCE LISTING

```
<160> NUMBER OF SEQ ID NOS: 23

<210> SEQ ID NO 1
<211> LENGTH: 3339
<212> TYPE: DNA
<213> ORGANISM: Homo sapiens
<220> FEATURE:
<221> NAME/KEY: CDS
<222> LOCATION: (203)..(1648)

<400> SEQUENCE: 1
acgtaaccta cggtgtcccg ctaggaaaga gaggtgcgtc aaacagcgac aagttccgcc      60
cacgtaaaag atgacgcttg gtgtgtcagc cgtccctgct gcccggttgc ttctcttttg     120
ggggcggggt ctagcaagag caggtgtggg tttaggagat atctccggag catttggata    180
atgtgacagt tggaatgcag tg atg tcg act ctt tgc cca ccg cca tct cca    232
                         Met Ser Thr Leu Cys Pro Pro Pro Ser Pro
                          1               5                  10 gct gtt gcc aag aca gag att gct tta agt ggc aaa tca cct tta tta    280
Ala Val Ala Lys Thr Glu Ile Ala Leu Ser Gly Lys Ser Pro Leu Leu
                15                  20                  25 gca gct act ttt gct tac tgg gac aat att ctt ggt cct aga gta agg    328
Ala Ala Thr Phe Ala Tyr Trp Asp Asn Ile Leu Gly Pro Arg Val Arg
         30                  35                  40 cac att tgg gct cca aag aca gaa cag gta ctt ctc agt gat gga gaa    376
His Ile Trp Ala Pro Lys Thr Glu Gln Val Leu Leu Ser Asp Gly Glu
     45                  50                  55 ata act ttt ctt gcc aac cac act cta aat gga gaa atc ctt cga aat    424
Ile Thr Phe Leu Ala Asn His Thr Leu Asn Gly Glu Ile Leu Arg Asn
 60                  65                  70 gca gag agt ggt gct ata gat gta aag ttt ttt gtc ttg tct gaa aag    472
Ala Glu Ser Gly Ala Ile Asp Val Lys Phe Phe Val Leu Ser Glu Lys
75                   80                  85                  90 gga gtg att att gtt tca tta atc ttt gat gga aac tgg aat ggg gat    520
Gly Val Ile Ile Val Ser Leu Ile Phe Asp Gly Asn Trp Asn Gly Asp
                 95                 100                 105 cgc agc aca tat gga cta tca att ata ctt cca cag aca gaa ctt agt    568
Arg Ser Thr Tyr Gly Leu Ser Ile Ile Leu Pro Gln Thr Glu Leu Ser
            110                 115                 120 ttc tac ctc cca ctt cat aga gtg tgt gtt gat aga tta aca cat ata    616
Phe Tyr Leu Pro Leu His Arg Val Cys Val Asp Arg Leu Thr His Ile
        125                 130                 135 atc cgg aaa gga aga ata tgg atg cat aag gaa aga caa gaa aat gtc    664
Ile Arg Lys Gly Arg Ile Trp Met His Lys Glu Arg Gln Glu Asn Val
    140                 145                 150 cag aag att atc tta gaa ggc aca gag aga atg gaa gat cag ggt cag    712
```

```
                Gln Lys Ile Ile Leu Glu Gly Thr Glu Arg Met Glu Asp Gln Gly Gln
                155                 160                 165                 170 agt att att cca atg ctt act gga gaa gtg att cct gta atg gaa ctg             760
Ser Ile Ile Pro Met Leu Thr Gly Glu Val Ile Pro Val Met Glu Leu
                175                 180                 185 ctt tca tct atg aaa tca cac agt gtt cct gaa gaa ata gat ata gct             808
Leu Ser Ser Met Lys Ser His Ser Val Pro Glu Glu Ile Asp Ile Ala
                190                 195                 200 gat aca gta ctc aat gat gat gat att ggt gac agc tgt cat gaa ggc             856
Asp Thr Val Leu Asn Asp Asp Asp Ile Gly Asp Ser Cys His Glu Gly
            205                 210                 215 ttt ctt ctc aat gcc atc agc tca cac ttg caa acc tgt ggc tgt tcc             904
Phe Leu Leu Asn Ala Ile Ser Ser His Leu Gln Thr Cys Gly Cys Ser
            220                 225                 230 gtt gta gta ggt agc agt gca gag aaa gta aat aag ata gtc aga aca             952
Val Val Val Gly Ser Ser Ala Glu Lys Val Asn Lys Ile Val Arg Thr
235                 240                 245                 250 tta tgc ctt ttt ctg act cca gca gag aga aaa tgc tcc agg tta tgt            1000
Leu Cys Leu Phe Leu Thr Pro Ala Glu Arg Lys Cys Ser Arg Leu Cys
                255                 260                 265 gaa gca gaa tca tca ttt aaa tat gag tca ggg ctc ttt gta caa ggc            1048
Glu Ala Glu Ser Ser Phe Lys Tyr Glu Ser Gly Leu Phe Val Gln Gly
                270                 275                 280 ctg cta aag gat tca act gga agc ttt gtg ctg cct ttc cgg caa gtc            1096
Leu Leu Lys Asp Ser Thr Gly Ser Phe Val Leu Pro Phe Arg Gln Val
            285                 290                 295 atg tat gct cca tat ccc acc aca cac ata gat gtg gat gtc aat act            1144
Met Tyr Ala Pro Tyr Pro Thr Thr His Ile Asp Val Asp Val Asn Thr
300                 305                 310 gtg aag cag atg cca ccc tgt cat gaa cat att tat aat cag cgt aga            1192
Val Lys Gln Met Pro Pro Cys His Glu His Ile Tyr Asn Gln Arg Arg
315                 320                 325                 330 tac atg aga tcc gag ctg aca gcc ttc tgg aga gcc act tca gaa gaa            1240
Tyr Met Arg Ser Glu Leu Thr Ala Phe Trp Arg Ala Thr Ser Glu Glu
                335                 340                 345 gac atg gct cag gat acg atc atc tac act gac gaa agc ttt act cct            1288
Asp Met Ala Gln Asp Thr Ile Ile Tyr Thr Asp Glu Ser Phe Thr Pro
            350                 355                 360 gat ttg aat att ttt caa gat gtc tta cac aga gac act cta gtg aaa            1336
Asp Leu Asn Ile Phe Gln Asp Val Leu His Arg Asp Thr Leu Val Lys
            365                 370                 375 gcc ttc ctg gat cag gtc ttt cag ctg aaa cct gga tta tct ctc aga            1384
Ala Phe Leu Asp Gln Val Phe Gln Leu Lys Pro Gly Leu Ser Leu Arg
380                 385                 390 agt act ttc ctt gca cag ttt cta ctt gtc ctt cac aga aaa gcc ttg            1432
Ser Thr Phe Leu Ala Gln Phe Leu Leu Val Leu His Arg Lys Ala Leu
395                 400                 405                 410 aca cta ata aaa tat ata gaa gac gat acg cag aag gga aaa aag ccc            1480
Thr Leu Ile Lys Tyr Ile Glu Asp Asp Thr Gln Lys Gly Lys Lys Pro
                415                 420                 425 ttt aaa tct ctt cgg aac ctg aag ata gac ctt gat tta aca gca gag            1528
Phe Lys Ser Leu Arg Asn Leu Lys Ile Asp Leu Asp Leu Thr Ala Glu
                430                 435                 440 ggc gat ctt aac ata ata atg gct ctg gct gag aaa att aaa cca ggc            1576
Gly Asp Leu Asn Ile Ile Met Ala Leu Ala Glu Lys Ile Lys Pro Gly
            445                 450                 455 cta cac tct ttt atc ttt gga aga cct ttc tac act agt gtg caa gaa            1624
Leu His Ser Phe Ile Phe Gly Arg Pro Phe Tyr Thr Ser Val Gln Glu
460                 465                 470
```

```
cga gat gtt cta atg act ttt taa atgtgtaact taataagcct attccatcac   1678
Arg Asp Val Leu Met Thr Phe
475                 480 aatcatgatc gctggtaaag tagctcagtg gtgtggggaa acgttcccct ggatcatact   1738
ccagaattct gctctcagca attgcagtta agtaagttac actacagttc tcacaagagc   1798
ctgtgagggg atgtcaggtg catcattaca ttgggtgtct cttttcctag atttatgctt   1858
ttgggataca gacctatgtt tacaatataa taaatattat tgctatcttt taaagatata   1918
ataataggat gtaaacttga ccacaactac tgttttttg aaatacatga ttcatggttt     1978
acatgtgtca aggtgaaatc tgagttggct tttacagata gttgactttc tatcttttgg   2038
cattctttgg tgtgtagaat tactgtaata cttctgcaat caactgaaaa ctagagcctt   2098
taaatgattt caattccaca gaaagaaagt gagcttgaac ataggatgag ctttagaaag   2158
aaaattgatc aagcagatgt ttaattggaa ttgattatta gatcctactt tgtggattta   2218
gtccctggga ttcagtctgt agaaatgtct aatagttctc tatagtcctt gttcctggtg   2278
aaccacagtt agggtgtttt gtttatttta ttgttcttgc tattgttgat attctatgta   2338
gttgagctct gtaaaaggaa attgtatttt atgttttagt aattgttgcc aactttttaa   2398
attaattttc attattttg agccaaattg aaatgtgcac ctcctgtgcc ttttttctcc    2458
ttagaaaatc taattacttg gaacaagttc agatttcact ggtcagtcat tttcatcttg   2518
ttttcttctt gctaagtctt accatgtacc tgctttggca atcattgcaa ctctgagatt   2578
ataaaatgcc ttagagaata tactaactaa taagatcttt ttttcagaaa cagaaaatag   2638
ttccttgagt acttccttct tgcatttctg cctatgtttt tgaagttgtt gctgtttgcc   2698
tgcaataggc tataaggaat agcaggagaa attttactga agtgctgttt tcctaggtgc   2758
tactttggca gagctaagtt atctttttgtt ttcttaatgc gtttggacca ttttgctggc   2818
tataaaataa ctgattaata taattctaac acaatgttga cattgtagtt acacaaacac   2878
aaataaatat tttatttaaa attctggaag taatataaaa gggaaaatat atttataaga   2938
aagggataaa ggtaatagag cccttctgcc ccccacccac caaatttaca caacaaaatg   2998
acatgttcga atgtgaaagg tcataatagc tttcccatca tgaatcagaa agatgtggac   3058
agcttgatgt tttagacaac cactgaacta gatgactgtt gtactgtagc tcagtcattt   3118
aaaaaatata taaatactac cttgtagtgt cccatactgt gttttttaca tggtagattc   3178
ttatttaagt gctaactggt tattttcttt ggctggttta ttgtactgtt atacagaatg   3238
taagttgtac agtgaaataa gttattaaag catgtgtaaa cattgttata tatcttttct   3298
cctaaatgga gaattttgaa taaaatatat ttgaaatttt g                       3339

<210> SEQ ID NO 2
<211> LENGTH: 30001
<212> TYPE: DNA
<213> ORGANISM: Homo sapiens

<400> SEQUENCE: 2
caaagaaaag ggggaggttt tgttaaaaaa gagaaatgtt acatagtgct ctttgagaaa     60
attcattggc actattaagg atctgaggag ctggtgagtt caactggtg agtgatggtg    120 gtagataaaa ttagagctgc agcaggtcat tttagcaact attagataaa actggtctca    180
ggtcacaacg ggcagttgca gcagctggac ttggagagaa ttacactgtg ggagcagtgt    240
catttgtcct aagtgctttt ctaccccta ccccactat tttagttggg tataaaaga      300 atgacccaat ttgtatgatc aactttcaca aagcatagaa cagtaggaaa agggtctgtt    360
```

```
tctgcagaag gtgtagacgt tgagagccat tttgtgtatt tattcctccc tttcttcctc    420
ggtgaatgat taaaacgttc tgtgtgattt ttagtgatga aaaagattaa atgctactca    480
ctgtagtaag tgccatctca cacttgcaga tcaaaaggca cacagtttaa aaaacctttg    540 ttttttttaca catctgagtg gtgtaaatgc tactcatctg tagtaagtgg aatctataca    600
cctgcagacc aaaagacgca aggtttcaaa aatctttgtg tttttttacac atcaaacaga    660 atggtacgtt tttcaaaagt taaaaaaaaa caactcatcc acatattgca actagcaaaa    720
atgacattcc ccagtgtgaa aatcatgctt gagagaattc ttacatgtaa aggcaaaatt    780
gcgatgactt tgcaggggac cgtgggattc ccgcccgcag tgccggagct gtcccctacc    840
agggtttgca gtggagtttt gaatgcactt aacagtgtct tacggtaaaa acaaaatttc    900
atccaccaat tatgtgttga gcgcccactg cctaccaagc acaaacaaaa ccattcaaaa    960
ccacgaaatc gtcttcactt tctccagatc cagcagcctc ccctattaag gttcgcacac   1020
gctattgcgc caacgctcct ccagagcggg tcttaagata aagaacagg acaagttgcc    1080 ccgcccatt tcgctagcct cgtgagaaaa cgtcatcgca catagaaaac agacagacgt    1140
aacctacggt gtcccgctag gaaagagagg tgcgtcaaac agcgacaagt tccgcccacg    1200
taaaagatga cgcttggtgt gtcagccgtc cctgctgccc ggttgcttct cttttggggg    1260
cggggtctag caagagcagg tgtgggttta ggaggtgtgt gttttgtttt tcccacccct    1320
ctctccccac tacttgctct cacagtactc gctgagggtg aacaagaaaa gacctgataa    1380
agattaacca gaagaaaaca aggagggaaa caaccgcagc ctgtagcaag ctctggaact    1440
caggagtcgc gcgctagggg ccggggccgg ggccggggcg tggtcggggc gggcccgggg    1500
gcgggcccgg ggcggggctg cggttgcggt gcctgcgccc gcggcggcgg aggcgcaggc    1560
ggtggcgagt gggtgagtga ggaggcggca tcctggcggg tggctgtttg gggttcggct    1620
gccgggaaga ggcgcgggta gaagcggggg ctctcctcag agctcgacgc atttttactt    1680
tccctctcat ttctctgacc gaagctgggt gtcgggcttt cgcctctagc gactggtgga    1740
attgcctgca tccgggcccc gggcttcccg gcggcggcgg cggcggcggc ggcgcaggga    1800
caagggatgg ggatctggcc tcttccttgc tttcccgccc tcagtacccg agctgtctcc    1860
ttcccgggga cccgctggga gcgctgccgc tgcgggctcg agaaaaggga gcctcgggta    1920
ctgagaggcc tcgcctgggg gaaggccgga gggtgggcgg cgcgcggctt ctgcggacca    1980
agtcggggtt cgctaggaac ccgagacggt ccctgccggc gaggagatca tgcgggatga    2040 gatggggtg tggagacgcc tgcacaattt cagcccaagc ttctagagag tggtgatgac    2100
ttgcatatga gggcagcaat gcaagtcggt gtgctcccca ttctgtggga catgacctgg    2160
ttgcttcaca gctccgagat gacacagact tgcttaaagg aagtgactat tgtgacttgg    2220
gcatcacttg actgatggta atcagttgtc taaagaagtg cacagattac atgtccgtgt    2280
gctcattggg tctatctggc cgcgttgaac accaccaggc tttgtattca gaaacaggag    2340
ggaggtcctg cactttccca ggaggggtgg ccctttcaga tgcaatcgag attgttaggc    2400
tctgggagag tagttgcctg gttgtggcag ttggtaaatt tctattcaaa cagttgccat    2460
gcaccagttg ttcacaacaa gggtacgtaa tctgtctggc attacttcta cttttgtaca    2520
aaggatcaaa aaaaaaaaag atactgttaa gatatgattt ttctcagact ttgggaaact    2580
tttaacataa tctgtgaata tcacagaaac aagactatca tatagggat attaataacc     2640 tggagtcaga atacttgaaa tacggtgtca tttgacacgg gcattgttgt caccacctct    2700
```

```
gccaaggcct gccactttag gaaaaccctg aatcagttgg aaactgctac atgctgatag    2760
tacatctgaa acaagaacga gagtaattac cacattccag attgttcact aagccagcat    2820
ttacctgctc caggaaaaaa ttacaagcac cttatgaagt tgataaaata ttttgtttgg    2880
ctatgttggc actccacaat ttgctttcag agaaacaaag taaaccaagg aggacttctg    2940
tttttcaagt ctgccctcgg gttctattct acgttaatta gatagttccc aggaggacta    3000
ggttagccta cctattgtct gagaaacttg gaactgtgag aaatggccag atagtgatat    3060
gaacttcacc ttccagtctt ccctgatgtt gaagattgag aaagtgttgt gaactttctg    3120
gtactgtaaa cagttcactg tccttgaagt ggtcctgggc agctcctgtt gtggaaagtg    3180
gacggtttag gatcctgctt ctctttgggc tgggagaaaa taaacagcat ggttacaagt    3240
attgagagcc aggttggaga aggtggctta cacctgtaat gccagagctt tgggaggcgg    3300
aggcaagagg atcacttgaa gccaggagtt caagctcaac ctgggcaacg tagaccctgt    3360
ctctacaaaa aattaaaaac ttagccgggc gtggtgatgt gcacctgtag tcctagctac    3420
ttgggaggct gaggcaggag ggtcatttga gcccaagagt tgaagttac cgagagctat    3480 gatcctgcca gtgcattcca gcctggatga caaaacgaga ccctgtctct aaaaaacaag    3540
aagtgagggc tttatgattg tagaattttc actacaatag cagtggacca accacctttc    3600
taaataccaa tcagggaaga gatggttgat ttttaacag acgtttaaag aaaaagcaaa    3660
acctcaaact tagcactcta ctaacagttt tagcagatgt taattaatgt aatcatgtct    3720
gcatgtatgg gattatttcc agaaagtgta ttgggaaacc tctcatgaac cctgtgagca    3780
agccaccgtc tcactcaatt tgaatctggg cttccctcaa aagactggct aatgtttggt    3840
aactctctgg agtagacagc actacatgta cgtaagatag gtacataaac aactattggt    3900
tttgagctga ttttttcag ctgcatttgc atgtatggat ttttctcacc aaagacgatg    3960
acttcaagta ttagtaaaat aattgtacag ctctcctgat tatacttctc tgtgacattt    4020
catttcccag gctatttctt ttggtaggat ttaaaactaa gcaattcagt atgatctttg    4080
tccttcattt tctttcttat tcttttttgtt tgtttgtttg tttgtttttt tcttgaggca    4140
gagtctctct ctgtcgccca ggctggagtg cagtggcgcc atctcagctc attgcaacct    4200
ctgccacctc cgggttcaag agattctcct gcctcagcct cccgagtagc tgggattaca    4260
ggtgtccacc accacacccg ctaatttttt tgtatttta gtagaggtgg ggtttcacca    4320
tgttggccag gctggtcttg agctcctgac ctcaggtgat ccacctgcct cggcctacca    4380
aagagctggg ataacaggtg tgacccacca tgcccggccc atttttttt tcttattctg    4440 ttaggagtga gagtgtaact agcagtataa tagttcaatt ttcacaacgt ggtaaaagtt    4500
tccctataat tcaatcagat tttgctccag ggttcagttc tgttttagga aatacttta    4560 ttttcagttt aatgatgaaa tattagagtt gtaatattgc ctttatgatt atccacctt    4620 ttaacctaaa agaatgaaag aaaaatatgt ttgcaatata attttatggt tgtatgttaa    4680
cttaattcat tatgttggcc tccagttttgc tgttgttagt tatgacagca gtagtgtcat    4740
taccatttca attcagatta cattcctata tttgatcatt gtaaactgac tgcttacatt    4800
gtattaaaaa cagtggatat tttaaagaag ctgtacggct tatatctagt gctgtctctt    4860
aagactatta aattgataca acatatttaa aagtaaatat tacctaaatg aattttttgaa    4920 attacaaata cacgtgttaa aactgtcgtt gtgttcaacc atttctgtac atacttagag    4980
ttaactgttt tgccaggctc tgtatgccta ctcataatg gataaaagca ctcatctaat    5040
gctctgtaaa tagaagtcag tgctttccat cagactgaac tctcttgaca agatgtggat    5100
```

```
gaaattcttt aagtaaaatt gtttactttg tcatacattt acagatcaaa tgttagctcc      5160
caaagcaatc atatggcaaa gataggtata tcatagtttg cctattagct gctttgtatt      5220
gctattatta taaatagact tcacagtttt agacttgctt aggtgaaatt gcaattcttt      5280
ttactttcag tcttagataa caagtcttca attatagtac aatcacacat tgcttaggaa      5340
tgcatcatta ggcgattttg tcattatgca aacatcatag agtgtactta cacaaaccta      5400
gatagtatag cctttatgta cctaggccgt atggtatagt ctgttgctcc taggccacaa      5460
acctgtacaa ctgttactgt actgaatact atagacagtt gtaacacagt ggtaaatatt      5520
tatctaaata tatgcaaaca gagaaaaggt acagtaaaag tatggtataa aagataatgg      5580
tatacctgtg taggccactt accacgaatg gagcttgcag gactagaagt tgctctgggt      5640
gagtcagtga gtgagtggtg aattaatgtg aaggcctaga acactgtaca ccactgtaga      5700
ctataaacac agtacgctga agctacacca aatttatctt aacagttttt cttcaataaa      5760
aaattataac tttttaactt tgtaaacttt ttaattttttt aacttttaaa atacttagct      5820
tgaaacacaa atacattgta tagctataca aaaatatttt ttctttgtat ccttattcta      5880
gaagcttttt tctattttct attttaaatt ttttttttta cttgttagtc gttttttgtta     5940 aaaactaaaa cacacacact ttcacctagg catagacagg attaggatca tcagtatcac      6000
tcccttccac ctcactgcct tccacctcca catcttgtcc cactggaagg ttttaagggg      6060
caataacaca catgtagctg tcacctatga taacagtgct ttctgttgaa tacctcctga      6120
aggacttgcc tgaggctgtt ttacatttaa cttaaaaaaa aaaaagtag aaggagtgca       6180 ctctaaaata acaataaaag gcatagtata gtgaatacat aaaccagcaa tgtagtagtt      6240
tattatcaag tgttgtacac tgtaataatt gtatgtgcta actttaaat aacttgcaaa       6300 atagtactaa gaccttatga tggttacagt gtcactaagg caatagcata ttttcaggtc      6360
cattgtaatc taatgggact accatcatat atgcagtcta ccattgactg aaacgttaca      6420
tggcacataa ctgtatttgc aagaatgatt tgttttacat taatatcaca taggatgtac      6480 cttttttagag tggtatgttt atgtggatta agatgtacaa gttgagcaag gggaccaaga     6540
gccctgggtt ctgtcttgga tgtgagcgtt tatgttcttc tcctcatgtc tgttttctca      6600
ttaaattcaa aggcttgaac gggccctatt tagcccttct gttttctacg tgttctaaat      6660
aactaaagct tttaaattct agccatttag tgtagaactc tctttgcagt gatgaaatgc      6720
tgtattggtt tcttggctag catattaaat atttttatct ttgtcttgat acttcaatgt      6780
cgttttaaac atcaggatcg ggcttcagta ttctcataac cagagagttc actgaggata      6840
caggactgtt tgcccatttt ttgttatggc tccagacttg tggtatttcc atgtctttttt     6900 ttttttttttt tttttttgacc ttttagcggc tttaaagtat ttctgttgtt aggtgttgta    6960 ttactttttct aagattactt aacaaagcac cacaaactga gtggctttaa acaacagcaa    7020
tttattctct cacaattcta gaagctagaa gtccgaaatc aaagtgttga caggggcatg     7080
atcttcaaga gagaagactc tttccttgcc tcttcctggc ttctggtggt taccagcaat     7140
cctgagtgtt cctttcttgc cttgtagttt caacaatcca gtatctgcct tttgtcttca    7200
catggctgtc taccatttgt ctctgtgtct ccaaatctct ctccttataa acacagcagt    7260
tattggatta ggccccactc taatccagta tgaccccatt ttaacatgat tacacttatt    7320
tctagataag gtcacattca cgtacaccaa gggttaggaa ttgaacatat cttttttgggg   7380 gacacaattc aacccacaag tgtcagtctc tagctgagcc tttcccttcc tgttttctc     7440
```

```
cttttttagtt gctatgggtt aggggccaaa tctccagtca tactagaatt gcacatggac      7500
tggatatttg ggaatactgc gggtctattc tatgagcttt agtatgtaac atttaatatc      7560
agtgtaaaga agccctttt  taagttattt ctttgaattt ctaaatgtat gccctgaata      7620
taagtaacaa gttaccatgt cttgtaaaat gatcatatca acaaacattt aatgtgcacc      7680
tactgtgcta gttgaatgtc tttatcctga taggagataa caggattcca catctttgac      7740
ttaagaggac aaaccaaata tgtctaaatc atttggggtt ttgatggata tcttttaaatt     7800 gctgaaccta atcattggtt tcatatgtca ttgtttagat atctccggag catttggata      7860
atgtgacagt tggaatgcag tgatgtcgac tctttgccca ccgccatctc cagctgttgc      7920
caagacagag attgctttaa gtggcaaatc acctttatta gcagctactt ttgcttactg      7980
ggacaatatt cttggtccta gagtaaggca catttgggct ccaaagacag aacaggtact      8040
tctcagtgat ggagaaataa cttttcttgc caaccacact ctaaatggag aaatccttcg      8100
aaatgcagag agtggtgcta tagatgtaaa gttttttgtc ttgtctgaaa agggagtgat      8160
tattgtttca ttaatctttg atggaaactg gaatggggat cgcagcacat atggactatc      8220
aattatactt ccacagacag aacttagttt ctacctccca cttcatagag tgtgtgttga      8280
tagattaaca catataatcc ggaaaggaag aatatgcatg cataaggtaa gtgatttttc      8340
agcttattaa tcatgttaac ctatctgttg aaagcttatt ttctggtaca tataaatctt      8400
atttttttaa ttatatgcag tgaacatcaa acaataaatg ttatttattt tgcatttacc      8460
ctattagata caaatacatc tggtctgata cctgtcatct tcatattaac tgtggaaggt      8520
acgaaatggt agctccacat tatagatgaa aagctaaagc ttagacaaat aaagaaactt      8580
ttagaccctg gattcttctt gggagccttt gactctaata cctttgtttt ccctttcatt      8640
gcacaattct gtcttttgct tactactatg tgtaagtata acagttcaaa gtaatagttt      8700
cataagctgt tggtcatgta gcctttggtc tctttaacct ctttgccaag ttcccaggtt      8760
cataaaatga ggaggttgaa tggaatggtt cccaagagaa ttccttttaa tcttacagaa      8820
attattgttt tcctaaatcc tgtagttgaa tatataatgc tatttacatt tcagtatagt      8880
tttgatgtat ctaaagaaca cattgaattc tccttcctgt gttccagttt gatactaacc      8940
tgaaagtcca ttaagcatta ccagttttaa aaggcttttg cccaatagta aggaaaaata      9000
atatctttta aaagaataat ttttactat  gtttgcaggc ttacttcctt ttttctcaca      9060
ttatgaaact cttaaaatca ggagaatctt ttaaacaaca tcataatgtt taatttgaaa      9120
agtgcaagtc attctttttcc ttttttgaaac tatgcagatg ttacattgac tgttttctgt     9180
gaagttatct ttttttcact gcagaataaa ggttgttttg atttttatttt gtattgtttta    9240 tgagaacatg catttgttgg gttaatttcc taccctgcc  cccatttttt ccctaaagta      9300
gaaagtattt ttcttgtgaa ctaaattact acacaagaac atgtctattg aaaaataagc      9360
aagtatcaaa atgttgtggg ttgttttttt aaataaattt tctcttgctc aggaaagaca      9420
agaaaatgtc cagaagatta tcttagaagg cacagagaga atggaagatc aggtatatgc      9480
aaattgcata ctgtcaaatg ttttttctcac agcatgtatc tgtataaggt tgatggctac     9540
atttgtcaag gccttggaga catacgaata agcctttaat ggagctttta tggaggtgta      9600
cagaataaac tggaggaaga tttccatatc ttaaacccaa agagttaaat cagtaaacaa      9660
aggaaaatag taattgcatc tacaaattaa tatttgctcc ctttttttt  ctgtttgccc      9720 agaataaatt ttgataact  tgttcatagt aaaaataaaa aaaattgtct ctgatatgtt      9780 cttttaaggta ctacttctcg aacctttccc tagaagtagc tgtaacagaa ggagagcata     9840
```

```
tgtacccctg aggtatctgt ctggggtgta ggcccaggtc cacacaatat ttcttctaag    9900
tcttatgttg tatcgttaag actcatgcaa tttacatttt attccataac tattttagta    9960
ttaaaatttg tcagtgatat ttcttaccct ctcctctagg aaaatgtgcc atgtttatcc   10020
cttggctttg aatgcccctc aggaacagac actaagagtt tgagaagcat ggttacaagg   10080
gtgtggcttc ccctgcggaa actaagtaca gactatttca ctgtaaagca gagaagttct   10140
tttgaaggag aatctccagt gaagaaagag ttcttcactt ttacttccat ttcctcttgt   10200
gggtgaccct caatgctcct tgtaaaactc caatatttta aacatggctg ttttgccttt   10260
ctttgcttct ttttagcatg aatgagacag atgatacttt aaaaaagtaa ttaaaaaaaa   10320
aaacttgtga aaatacatgg ccataataca gaacccaata caatgatctc ctttaccaaa   10380
ttgttatgtt tgtacttttg tagatagctt tccaattcag agacagttat tctgtgtaaa   10440
ggtctgactt aacaagaaaa gatttccctt tacccaaaga atcccagtcc ttatttgctg   10500
gtcaataagc agggtcccca ggaatggggt aactttcagc accctctaac ccactagtta   10560
ttagtagact aattaagtaa acttatcgca agttgaggaa acttagaacc aactaaaatt   10620
ctgcttttac tgggattttg ttttttcaaa ccagaaacct ttacttaagt tgactactat   10680
taatgaattt tggtctctct tttaagtgct cttcttaaaa atgttatctt actgctgaga   10740
agttcaagtt tgggaagtac aaggaggaat agaaacttaa gagattttct tttagagcct   10800
cttctgtatt tagccctgta ggattttttt tttttttttt tttttggtg ttgttgagct   10860
tcagtgaggc tattcattca cttatactga taatgtctga gatactgtga atgaaatact   10920
atgtatgctt aaacctaaga ggaaatattt tcccaaaatt attcttcccg aaaaggagga   10980
gttgcctttt gattgagttc ttgcaaatct cacaacgact ttatttgaa caatactgtt   11040
tggggatgat gcattagttt gaaacaactt cagttgtagc tgtcatctga taaaattgct   11100
tcacagggaa ggaaatttaa cacggatcta gtcattattc ttgttagatt gaatgtgtga   11160
attgtaattg taaacaggca tgataattat tactttaaaa actaaaaaca gtgaatagtt   11220
agttgtggag gttactaaag gatggttttt ttttaaataa aactttcagc attatgcaaa   11280
tgggcatatg gcttaggata aaacttccag aagtagcatc acatttaaat tctcaagcaa   11340
cttaataata tggggctctg aaaaactggt taaggttact ccaaaaatgg ccctgggtct   11400
gacaaagatt ctaacttaaa gatgcttatg aagactttga gtaaaatcat ttcataaaat   11460
aagtgaggaa aaacaactag tattaaattc atcttaaata atgtatgatt taaaaaatat   11520
gtttagctaa aaatgcatag tcatttgaca atttcattta tatctcaaaa aatttactta   11580
accaagttgg tcacaaaact gatgagactg gtggtggtag tgaataaatg agggaccatc   11640
catatttgag acactttaca tttgtgatgt gttatactga atttttcagtt tgattctata   11700
gactacaaat ttcaaaatta caatttcaag atgtaataag tagtaatatc ttgaaatagc   11760
tctaaaggga attttttctgt tttattgatt cttaaaatat atgtgctgat tttgatttgc   11820
atttgggtag attatacttt tatgagtatg gaggttaggt attgattcaa gttttcctta   11880
cctatttggt aaggatttca agtctttttt gtgcttggtt ttcctcattt ttaaatatga   11940
aatatattga tgacctttaa caaattttttt ttatctcaaa ttttaaagga gatcttttct   12000
aaaagaggca tgatgactta atcattgcat gtaacagtaa acgataaacc aatgattcca   12060
tactctctaa agaataaaag tgagcttag ggccgggcat ggtcagaaat ttgacaccaa   12120
cctggccaac atggcgaaac cccgtctcta ctaaaaatac aaaaatcagc cgggcatggt   12180
```

```
ggcggcacct atagtcccag ctacttggga ggatgagaca ggagagtcac ttgaacctgg    12240
gaggagaggt tgcagtgagc tgagatcacg ccattgcact ccagcctgag caatgaaagc    12300
aaaactccat ctcaaaaaaa aaaaagaaa  agaaagaata aaagtgagct tggattgca     12360 tataaatcct ttagacatgt agtagacttg tttgatactg tgtttgaaca aattacgaag    12420
tattttcatc aaagaatgtt attgtttgat gttattttta ttttttattg cccagcttct    12480
ctcatattac gtgattttct tcacttcatg tcactttatt gtgcagggtc agagtattat    12540
tccaatgctt actggagaag tgattcctgt aatggaactg ctttcatcta tgaaatcaca    12600
cagtgttcct gaagaaatag atgtaagttt aaatgagagc aattatacac tttatgagtt    12660
ttttggggtt atagtattat tatgtatatt attaatattc taattttaat agtaaggact    12720
ttgtcataca tactattcac atacagtatt agccacttta gcaaataagc acacacaaaa    12780
tcctggattt tatggcaaaa cagaggcatt tttgatcagt gatgacaaaa ttaaattcat    12840
tttgtttatt tcattacttt tataattcct aaaagtggga ggatcccagc tcttatagga    12900
gcaattaata tttaatgtag tgtcttttga acaaaactg  tgtgccaaag tagtaaccat    12960
taatggaagt ttacttgtag tcacaaattt agtttcctta atcatttgtt gaggacgttt    13020
tgaatcacac actatgagtg ttaagagata cctttaggaa actattcttg ttgttttctg    13080
attttgtcat ttaggttagt ctcctgattc tgacagctca gaagaggaag ttgttcttgt    13140
aaaaattgtt taacctgctt gaccagcttt cacatttgtt cttctgaagt ttatggtagt    13200
gcacagagat tgttttttgg ggagtcttga ttctcggaaa tgaaggcagt gtgttatatt    13260
gaatccagac ttccgaaaac ttgtatatta aaagtgttat ttcaacacta tgttacagcc    13320
agactaattt ttttattttt tgatgcattt tagatagctg atacagtact caatgatgat    13380
gatattggtg acagctgtca tgaaggcttt cttctcaagt aagaattttt cttttcataa    13440
aagctggatg aagcagatac catcttatgc tcacctatga caagatttgg aagaaagaaa    13500
ataacagact gtctacttag attgttctag ggacattacg tatttgaact gttgcttaaa    13560
tttgtgttat ttttcactca ttatatttct atatatattt ggtgttattc catttgctat    13620
ttaaagaaac cgagtttcca tcccagacaa gaaatcatgg ccccttgctt gattctggtt    13680
tcttgtttta cttctcatta aagctaacag aatcctttca tattaagttg tactgtagat    13740
gaacttaagt tatttaggcg tagaacaaaa ttattcatat ttatactgat cttttttccat    13800 ccagcagtgg agtttagtac ttaagagttt gtgcccttaa accagactcc ctggattaat    13860
gctgtgtacc cgtgggcaag gtgcctgaat tctctataca cctatttcct catctgtaaa    13920
atggcaataa tagtaatagt acctaatgtg tagggttgtt ataagcattg agtaagataa    13980
ataatataaa gcacttagaa cagtgcctgg aacataaaaa cacttaataa tagctctag   14040 ctaacatttc ctatttacat ttcttctaga aatagccagt atttgttgag tgcctacatg    14100
ttagttcctt tactagttgc tttacatgta ttatcttata ttctgtttta aagtttcttc    14160
acagttacag attttcatga aatttttactt ttaataaaag agaagtaaaa gtataaagta    14220
ttcactttta tgttcacagt cttttccttt aggctcatga tggagtatca gaggcatgag    14280
tgtgtttaac ctaagagcct taatggcttg aatcagaagc actttagtcc tgtatctgtt    14340
cagtgtcagc ctttcataca tcattttaaa tcccatttga ctttaagtaa gtcacttaat    14400
ctctctacat gtcaatttct tcagctataa aatgatggta tttcaataaa taaatacatt    14460
aattaaatga tattatactg actaattggg ctgttttaag gctcaataag aaaatttctg    14520
tgaaaggtct ctagaaaatg taggttccta tacaaataaa agataacatt gtgcttatag    14580
```

```
cttcggtgtt tatcatataa agctattctg agttatttga agagctcacc tactttttt    14640 tgttttagt ttgttaaatt gttttatagg caatgtttt aatctgtttt ctttaactta    14700
cagtgccatc agctcacact tgcaaacctg tggctgttcc gttgtagtag gtagcagtgc    14760
agagaaagta aataaggtag tttattttat aatctagcaa atgatttgac tctttaagac    14820
tgatgatata tcatggattg tcatttaaat ggtaggttgc aattaaaatg atctagtagt    14880
ataaggaggc aatgtaatct catcaaattg ctaagacacc ttgtggcaac agtgagtttg    14940
aaataaactg agtaagaatc atttatcagt ttattttgat agctcggaaa taccagtgtc    15000
agtagtgtat aaatggtttt gagaatatat taaaatcaga tatataaaaa aaattactct    15060
tctatttccc aatgttatct ttaacaaatc tgaagatagt catgtacttt tggtagtagt    15120
tccaaagaaa tgttatttgt ttattcatct tgatttcatt gtcttcgctt tccttctaaa    15180 tctgtcccctt ctagggagct attgggatta agtggtcatt gattattata ctttattcag    15240
taatgtttct gacccttccc ttcagtgcta cttgagttaa ttaaggatta atgaacagtt    15300
acatttccaa gcattagcta ataaactaaa ggattttgca cttttcttca ctgaccatta    15360
gttagaaaga gttcagagat aagtatgtgt atctttcaat ttcagcaaac ctaattttt    15420 aaaaaaagtt ttacatagga aatatgttgg aaatgatact ttacaaagat attcataatt    15480
tttttttgta atcagctact ttgtatattt acatgagcct taatttatat ttctcatata    15540
accatttatg agagcttagt atacctgtgt cattatattg catctacgaa ctagtgacct    15600
tattccttct gttacctcaa acaggtggct ttccatctgt gatctccaaa gccttaggtt    15660
gcacagagtg actgccgagc tgctttatga agggagaaag gctccatagt tggagtgttt    15720
tttttttttt ttttaaacat ttttcccatc ctccatcctc ttgagggaga atagcttacc    15780 tttatcttg ttttaatttg agaaagaagt tgccaccact ctaggttgaa aaccactcct    15840
ttaacataat aactgtggat atggtttgaa tttcaagata gttacatgcc ttttatttt    15900 tcctaataga gctgtaggtc aaatattatt agaatcagat ttctaaatcc cacccaatga    15960
cctgcttatt ttaaatcaaa ttcaataatt aattctcttc tttttggagg atctggacat    16020
tctttgatat ttcttacaac gaatttcatg tgtagaccca ctaaacagaa gctataaaag    16080
ttgcatggtc aaataagtct gagaaagtct gcagatgata taattcaccct gaagagtcac    16140 agtatgtagc caaatgttaa aggttttgag atgccataca gtaaatttac caagcatttt    16200
ctaaatttat ttgaccacag aatccctatt ttaagcaaca actgttacat cccatggatt    16260
ccaggtgact aaagaatact tatttcttag gatatgtttt attgataata acaattaaaa    16320
tttcagatat ctttcataag caaatcagtg gtcttttac ttcatgtttt aatgctaaaa    16380
tatttctttt tatagatagt cagaacatta tgccttttc tgactccagc agagagaaaa    16440
tgctccaggt tatgtgaagc agaatcatca tttaaatatg agtcagggct ctttgtacaa    16500
ggcctgctaa aggtatagtt tctagttatc acaagtgaaa ccacttttct aaaatcattt    16560
ttgagactct ttatagacaa atcttaaata ttagcattta atgtatctca tattgacatg    16620
cccagagact gacttccttt acacagttct gcacatagac tatatgtctt atggatttat    16680
agttagtatc atcagtgaaa caccatagaa tacccttgt gttccaggtg ggtccctgtt    16740
cctacatgtc tagcctcagg acttttttt ttttaacaca tgcttaaatc aggttgcaca    16800
tcaaaaataa gatcatttct ttttaactaa atagatttga attttattga aaaaaaattt    16860
taaacatctt taagaagctt ataggattta agcaattcct atgtatgtgt actaaaatat    16920
```

```
atatatttct atatataata tatattagaa aaaaattgta ttttcttttt atttgagtct    16980
actgtcaagg agcaaaacag agaaatgtaa attagcaatt attttataata cttaaaggga   17040 agaaagttgt tcaccttgtt gaatctatta ttgttatttc aattatagtc ccaagacgtg   17100
aagaaatagc tttcctaatg gttatgtgat tgtctcatag tgactacttt cttgaggatg   17160
tagccacggc aaaatgaaat aaaaaaattt aaaaattgtt gcaaatacaa gttatattag   17220
gcttttgtgc attttcaata atgtgctgct atgaactcag aatgatagta tttaaatata   17280
gaaactagtt aaaggaaacg tagtttctat ttgagttata catatctgta aattagaact   17340
tctcctgtta aaggcataat aaagtgctta atacttttgt ttcctcagca ccctctcatt   17400
taattatata attttagttc tgaaagggac ctataccaga tgcctagagg aaatttcaaa   17460
actatgatct aatgaaaaaa tatttaatag ttctccatgc aaatacaaat catatagttt   17520
tccagaaaat acctttgaca ttatacaaag atgattatca cagcattata atagtaaaaa   17580 aatgaaata gcctctttct tctgttctgt tcatagcaca gtgcctcata cgcagtaggt   17640
tattattaca tggtaactgg ctaccccaac tgattaggaa agaagtaaat ttgttttata   17700
aaaatacata ctcattgagg tgcatagaat aattaagaaa ttaaaagaca cttgtaattt   17760
tgaatccagt gaatacccac tgttaatatt tggtatatct ctttctagtc tttttttccc   17820
ttttgcatgt attttcttta agactcccac ccccactgga tcatctctgc atgttctaat   17880
ctgctttttt cacagcagat tctaagcctc tttgaatatc aacacaaact tcaacaactt   17940
catctataga tgccaaataa taaattcatt tttatttact taaccacttc ctttggatgc   18000
ttaggtcatt ctgatgtttt gctattgaaa ccaatgctat actgaacact tctgtcacta   18060
aaactttgca cacactcatg aatagcttct taggataaat ttttagagat ggatttgcta   18120
aatcagagac catttttaa aattaaaaaa caattattca tatcgtttgg catgtaagac   18180
agtaaatttt ccttttattt tgacaggatt caactggaag cttttgtgctg cctttccggc   18240 aagtcatgta tgctccatat cccaccacac acatagatgt ggatgtcaat actgtgaagc   18300
agatgccacc ctgtcatgaa catatttata atcagcgtag atacatgaga tccgagctga   18360
cagccttctg gagagccact tcagaagaag acatggctca ggatacgatc atctacactg   18420
acgaaagctt tactcctgat ttgtacgtaa tgctctgcct gctggtactg tagtcaagca   18480
atatgaaatt gtgtctttta cgaataaaaa caaaacagaa gttgcattta aaagaaaga   18540 aatattacca gcagaattat gcttgaagaa acatttaatc aagcattttt ttcttaaatg   18600
ttcttctttt tccatacaat tgtgtttacc ctaaaatagg taagattaac ccttaaagta   18660
aatatttaac tatttgttta ataaatatat attgagctcc taggcactgt tctaggtacc   18720
gggcttaata gtggccaacc agacagcccc agccccagcc cctacattgt gtatagtcta   18780
ttatgtaaca gttattgaat ggacttatta acaaaaccaa agaagtaatt ctaagtcttt   18840 ttttttcttga catatgaata taaaatacag caaaactgtt aaaatatatt aatgaacat   18900 ttttttactt tgcattttat attgttattc acttcttatt ttttttaaa aaaaaagcc   18960 tgaacagtaa attcaaaagg aaaagtaatg ataattaatt gttgagcatg gacccaactt   19020
gaaaaaaaaa atgatgatga taaatctata atcctaaaac cctaagtaaa cacttaaaag   19080
atgttctgaa atcaggaaaa gaattatagt atactttgt gtttctcttt tatcagttga   19140
aaaaaggcac agtagctcat gcctgtaaga acagagcttt gggagtgcaa ggcaggcgga   19200
tcacttgagg ccaggagttc cagaccagcc tgggcaacat agtgaaaccc catctctaca   19260
aaaaataaaa aagaattatt ggaatgtgtt tctgtgtgcc tgtaatccta gctattccga   19320
```

```
aagctgaggc aggaggatct tttgagccca ggagtttgag gttacaggga gttatgatgt   19380
gccagtgtac tccagcctgg ggaacaccga gactctgtct tatttaaaaa aaaaaaaaaa   19440
aaaatgcttg caataatgcc tggcacatag aaggtaacag taagtgttaa ctgtaataac   19500
ccaggtctaa gtgtgtaagg caatagaaaa attggggcaa ataagcctga cctatgtatc   19560
tacagaatca gtttgagctt aggtaacaga cctgtggagc accagtaatt acacagtaag   19620
tgttaaccaa aagcatagaa taggaatatc ttgttcaagg acccccagc cttatacatc    19680 tcaaggtgca gaaagatgac ttaatatagg acccatttt tcctagttct ccagagtttt    19740
tattggttct tgagaaagta gtaggggaat gttttagaaa atgaattggt ccaactgaaa   19800
ttacatgtca gtaagttttt atatattggt aaatttagt agacatgtag aagttttcta    19860
attaatctgt gccttgaaac attttctttt ttcctaaagt gcttagtatt ttttccgttt   19920
tttgattggt tacttgggag cttttttgag gaaatttagt gaactgcaga atgggtttgc   19980
aaccatttgg tattttgtt ttgtttttta gaggatgtat gtgtatttta acatttctta    20040
atcattttta gccagctatg tttgtttgc tgatttgaca aactacagtt agacagctat    20100
tctcattttg ctgatcatga caaaataata tcctgaattt ttaaattttg catccagctc   20160
taaattttct aaacataaaa ttgtccaaaa aatagtattt tcagccacta gattgtgtgt   20220
taagtctatt gtcacagagt cattttactt ttaagtatat gttttacat gttaattatg    20280 tttgttattt ttaattttaa cttttttaaaa taattccagt cactgccaat acatgaaaaa  20340
ttggtcactg gaattttttt tttgacttt attttaggtt catgtgtaca tgtgcaggtg    20400
tgttatacag gtaaattgcg tgtcatgagg gtttggtgta caggtgattt cattacccag   20460
gtaataagca tagtacccaa taggtagttt tttgatcctc acccttctcc caccctcaag   20520
taggccctgg tgttgctgtt tccttctttg tgtccatgta tactcagtgt ttagctccca   20580
cttagaagtg agaacatgcg gtagttggtt ttctgttcct ggattagttc acttaggata   20640
atgacctcta gctccatctg gttttatgg ctgcatagta ttccatggtg tatatgtatc    20700 acatttctt tatccagtct accattgata ggcatttagg ttgattccct gtctttgtta    20760
tcatgaatag tgctgtgatg aacatacaca tgcatgtgtc tttatggtag aaaaatttgt   20820
attcctttag gtacatatag aataatgggg ttgctagggt gaatggtagt tctattttca   20880
gttatttgag aaatcttcaa actgcttttc ataatagcta aactaattta cagtcccgcc   20940
agcagtgtat aagtgttccc ttttctccac aaccttgcca acatctgtga ttttttgact   21000
ttttaataat agccattcct agagaattga tttgcaattc tctattagtg atattaagca   21060 tttttcata tgcttttag ctgtctgtat atattcttct gaaaaatttt catgtccttt     21120
gcccagtttg tagtggggtg ggttgttttt tgcttgttaa ttagttttaa gttccttcca   21180
gattctgcat atccctttgt tggatacatg gtttgcagat attttctcc cattgtgtag    21240 gttgtctttt actctgttga tagtttcttt tgccatgcag gagctcgtta ggtcccattt   21300
gtgtttgttt ttgttgcagt tgcttttggc gtcttcatca taaaatctgt gccagggcct   21360
atgtccagaa tggtatttcc taggttgtct tccagggttt ttacaatttt agattttacg   21420
tttatgtctt taatccatct tgagttgatt tttgtatatg gcacaaggaa ggggtccagt   21480
ttcactccaa ttcctatggc tagcaattat cccagcacca tttattgaat acggagtcct   21540
ttccccattg cttgtttttt gtcaactttg ttgaagatca gatggttgta agtgtgtggc   21600
tttatttctt ggctctctat tctccattgg tctatgtgtc tgttttttata acagtaccct  21660
```

```
gctgttcagg ttcctatagc cttttagtat aaaatcggct aatgtgatgc ctccagcttt    21720 gttcttttg cttaggattg ctttggctat ttgggctcct ttttgggtcc atattaattt     21780
taaaacagtt ttttctggtt ttgtgaagga tatcattggt agtttatagg aatagcattg    21840
aatctgtaga ttgctttggg cagtatggcc attttaacaa tattaattct tcctatctat    21900
gaatatggaa tgttttttcca tgtgtttgtg tcatctcttt atacctgatg tataaagaaa   21960
agctggtatt attcctactc aatctgttcc aaaaaattga ggaggaggaa ctcttcccta    22020
atgaggccag catcattctg ataccaaaac ctggcagaga cacaacagaa aaagaaaac    22080 ttcaggccaa tatccttgat gaatatagat gcaaaaatcc tcaacaaaat actagcaaac    22140
caaatccagc agcacatcaa aaagctgatc tactttgatc aagtaggctt tatccctggg    22200
atgcaaggtt ggttcaacat acacaaatca ataagtgtga ttcatcacat aaacagagct    22260
aaaaacaaaa accacaagat tatctcaata ggtagagaaa aggttgtcaa taaaatttaa    22320
catcctccat gttaaaaacc ttcagtaggt caggtgtagt gactcacacc tgtaatccca    22380
gcactttggg aggccaaggc gggcatatct cttaagccca ggagttcaag acgagcctag    22440
gcagcatggt gaaaccccat ctctacaaaa aaaaaaaaa aaaaaaatta gcttggtatg    22500
gtgacatgca cctatagtcc cagctattca ggaggttgag gtgggaggat tgtttgagcc    22560
cgggaggcag aggttggcag cgagctgaga tcatgccacc gcactccagc ctgggcaacg    22620
gagtgagacc ctgtctcaaa aagaaaaat cacaaacaat cctaaacaaa ctaggcattg    22680
aaggaacatg cctcaaaaaa ataagaacca tctatgacag acccatagcc aatatcttac    22740
caaatgggca aaagctggaa gtattctcct tgagaaccgt aacaagacaa ggatgtccac    22800
tctcaccact ccttttcagc atagttctgg aagtcctagc cagagcaatc aggaaagaga    22860
aagaaagaaa gacattcaga taggaagaga agaagtcaaa ctatttctgt ttgcaggcag    22920
tataattctg tacctagaaa atctcatagt ctctgcccag aaactcctaa atctgttaaa    22980
aatttcagca aagttttggc attctctata ctccaacacc ttccaaagtg agagcaaaat    23040
caagaacaca gtcccattca caatagccgc aaaacgaata aaatacctag gaatccagct    23100
aaccagggag gtgaaagatc tctatgagaa ttacaaaaca ctgctgaaag aaatcagaga    23160
tgacacaaac aaatggaaat gttcttttt aacaccttgc tttatctaat tcacttatga    23220
tgaagatact cattcagtgg aacaggtata ataagtccac tcgattaaat ataagcctta    23280
ttctctttcc agagcccaag aagggcact atcagtgccc agtcaataat gacgaaatgc    23340
taatattttt cccctttacg gtttctttct tctgtagtgt ggtacactcg tttcttaaga    23400
taaggaaact tgaactacct tcctgtttgc ttctacacat acccattctc ttttttgcc    23460 actctggtca ggtataggat gatccctacc actttcagtt aaaaactcct cctcttacta    23520
aatgttctct taccctctgg cctgagtaga acctagggaa aatggaagag aaaaagatga    23580
aagggaggtg gggcctggga agggaataag tagtcctgtt tgtttgtgtg tttgctttag    23640
cacctgctat atcctaggtg ctgtgttagg cacacattat tttaagtggc cattatatta    23700
ctactactca ctctggtcgt tgccaaggta ggtagtactt tcttggatag ttggttcatg    23760
ttacttacag atggtgggct tgttgaggca aacccagtgg ataatcatcg gagtgtgttc    23820
tctaatctca ctcaaatttt tcttcacatt ttttggtttg ttttggtttt tgatggtagt    23880
ggcttatttt tgttgctggt ttgttttttg tttttttttg agatggcaag aattggtagt    23940
tttatttatt aattgcctaa gggtctctac tttttttaaa agatgagagt agtaaaatag    24000
attgatagat acatacatac ccttactggg gactgcttat attctttaga gaaaaaatta    24060
```

```
catattagcc tgacaaacac cagtaaaatg taaatatatc cttgagtaaa taaatgaatg   24120
tatattttgt gtctccaaat atatatatct atattcttac aaatgtgttt atatgtaata   24180
tcaatttata agaacttaaa atgttggctc aagtgaggga ttgtggaagg tagcattata   24240
tggccatttc aacatttgaa cttttttctt ttcttcattt tcttcttttc ttcaggaata   24300
tttttcaaga tgtcttacac agagacactc tagtgaaagc cttcctggat caggtaaatg   24360
ttgaacttga gattgtcaga gtgaatgata tgacatgttt tctttttttaa tatatcctac   24420 aatgcctgtt ctatatattt atattcccct ggatcatgcc ccagagttct gctcagcaat   24480
tgcagttaag ttagttacac tacagttctc agaagagtct gtgagggcat gtcaagtgca   24540
tcattacatt ggttgcctct tgtcctagat ttatgcttcg ggaattcaga cctttgttta   24600
caatataata aatattattg ctatctttta aagatataat aataagatat aaagttgacc   24660
acaactactg ttttttgaaa catagaattc ctggtttaca tgtatcaaag tgaaatctga   24720
cttagctttt acagatataa tatatacata tatatatcct gcaatgcttg tactatatat   24780
gtagtacaag tatatatata tgtttgtgtg tgtatatata tatagtacga gcatatatac   24840
atattaccag cattgtagga tatatatatg tttatatatt aaaaaaaagt tataaactta   24900
aaaccctatt atgttatgta gagtatatgt tatatatgat atgtaaaata tataacatat   24960
actctatgat agagtgtaat atatttttta tatatatttt aacatttata aaatgataga   25020
attaagaatt gagtcctaat ctgttttatt aggtgctttt tgtagtgtct ggtctttcta   25080
aagtgtctaa atgattttc cttttgactt attaatgggg aagagcctgt atattaacaa   25140
ttaagagtgc agcattccat acgtcaaaca acaaacattt taattcaagc attaacctat   25200
aacaagtaag tttttttttt ttttttgaga aagggaggtt gtttatttgc ctgaaatgac   25260
tcaaaaatat ttttgaaaca tagtgtactt atttaaataa catctttatt gtttcattct   25320
tttaaaaaat atctacttaa ttacacagtt gaaggaaatc gtagattata tggaacttat   25380
ttcttaatat attacagttt gttataataa cattctgggg atcaggccag gaaactgtgt   25440
catagataaa gctttgaaat aatgagatcc ttatgtttac tagaaatttt ggattgagat   25500
ctatgaggtc tgtgacatat tgcgaagttc aaggaaaatt cgtaggcctg gaatttcatg   25560
cttctcaagc tgacataaaa tccctcccac tctccacctc atcatatgca cacattctac   25620
tcctacccac ccactccacc ccctgcaaaa gtacaggtat atgaatgtct caaaccata   25680 ggctcatctt ctaggagctt caatgttatt tgaagatttg ggcagaaaaa attaagtaat   25740
acgaaataac ttatgtatga gttttaaaag tgaagtaaac atggatgtat tctgaagtag   25800
aatgcaaaat ttgaatgcat ttttaaagat aaattagaaa acttctaaaa actgtcagat   25860
tgtctgggcc tggtggctta tgcctgtaat cccagcactt tgggagtccg aggtgggtgg   25920
atcacaaggt caggagatcg agaccatcct gccaacatgg tgaaaccccg tctctactaa   25980
gtatacaaaa attagctggg cgtggcagcg tgtgcctgta atcccagcta cctgggaggc   26040
tgaggcagga gaatcgcttg aacccaggag gtgtaggttg cagtgagtca agatcgcgcc   26100
actgcacttt agcctggtga cagagctaga ctccgtctca aaaaaaaaaa aaaatatcag   26160
attgttccta cacctagtgc ttctatacca cactcctgtt aggggcatc agtggaaatg   26220 gttaaggaga tgtttagtgt gtattgtctg ccaagcactg tcaacactgt catagaaact   26280
tctgtacgag tagaatgtga gcaaattatg tgttgaaatg gttcctctcc ctgcaggtct   26340
ttcagctgaa acctggctta tctctcagaa gtactttcct tgcacagttt ctacttgtcc   26400
```

```
ttcacagaaa agccttgaca ctaataaaat atatagaaga cgatacgtga gtaaaactcc    26460
tacacggaag aaaaacctتt gtacattgtt tttttgtttt gtttcctttg tacatttict    26520 atatcataat ttttgcgctt cttttttttt tttttttttt ttttttttcca ttattttag    26580 gcagaaggga aaaaagccct taaatctct tcggaacctg aagatagacc ttgatttaac    26640
agcagagggc gatcttaaca taataatggc tctggctgag aaaattaaac caggcctaca    26700 ctctttatc tttggaagac cttctacac tagtgtgcaa gaacgagatg ttctaatgac    26760 ttttaaatg tgtaacttaa taagcctatt ccatcacaat catgatcgct ggtaaagtag    26820
ctcagtggtg tggggaaacg ttcccctgga tcatactcca gaattctgct ctcagcaatt    26880
gcagttaagt aagttacact acagttctca caagagcctg tgaggggatg tcaggtgcat    26940
cattacattg ggtgtctctt ttcctagatt tatgcttttg ggatacagac ctatgtttac    27000
aatataataa atattattgc tatcttttaa agatataata ataggatgta aacttgacca    27060
caactactgt ttttttgaaa tacatgattc atggttaca tgtgtcaagg tgaaatctga    27120 gttggcttt acagatagtt gactttctat cttttggcat tctttggtgt gtagaattac    27180
tgtaatactt ctgcaatcaa ctgaaaacta gagcctttaa atgatttcaa ttccacagaa    27240
agaaagtgag cttgaacata ggatgagctt tagaaagaaa attgatcaag cagatgttta    27300
attggaattg attattagat cctactttgt ggatttagtc cctgggattc agtctgtaga    27360
aatgtctaat agttctctat agtccttgtt cctggtgaac cacagttagg gtgttttgtt    27420
tattttattg ttcttgctat tgttgatatt ctatgtagtt gagctctgta aaaggaaatt    27480 gtatttatg ttttagtaat tgttgccaac ttttaaatt aatttttcatt attttttgagc    27540 caaattgaaa tgtgcacctc ctgtgccttt tttctcctta gaaaatctaa ttacttggaa    27600
caagttcaga tttcactggt cagtcatttt catcttgttt tcttcttgct aagtcttacc    27660
atgtacctgc tttggcaatc attgcaactc tgagattata aaatgcctta gagaatatac    27720
taactaataa gatcttttt tcagaaacag aaaatagttc cttgagtact tccttcttgc    27780
atttctgcct atgttttga agttgttgct gtttgcctgc aataggctat aaggaatagc    27840 aggagaaat ttactgaagt gctgttttcc taggtgctac tttggcagag ctaagttatc    27900
ttttgttttc ttaatgcgtt tggaccattt tgctggctat aaaataactg attaatataa    27960
ttctaacaca atgttgacat tgtagttaca caaacacaaa taaatatttt atttaaaatt    28020
ctggaagtaa tataaaaggg aaaatatatt tataagaaag ggataaaggt aatagagccc    28080
ttctgccccc cacccaccaa atttacacaa caaaatgaca tgttcgaatg tgaaaggtca    28140
taatagcttt cccatcatga atcagaaaga tgtggacagc ttgatgtttt agacaaccac    28200
tgaactagat gactgttgta ctgtagctca gtcatttaaa aaatatataa atactacctt    28260
gtagtgtccc atactgtgtt ttttacatgg tagattctta tttaagtgct aactggttat    28320 tttcttggc tggtttattg tactgttata cagaatgtaa gttgtacagt gaaataagtt    28380
attaaagcat gtgtaaacat tgttatatat cttttctcct aaatggagaa ttttgaataa    28440
aatatatttg aaattttgcc tctttcagtt gttcattcag aaaaaaatac tatgatattt    28500
gaagactgat cagcttctgt tcagctgaca gtcatgctgg atctaaactt ttttttaaaat    28560 taattttgtc ttttcaaaga aaaatatttt aaagaagctt tataatataa tcttatgtta    28620
aaaaaacttt ctgcttaact ctctggattt catttigatt tttcaaatta tatattaata    28680
tttcaaatgt aaaatactat ttagataaat tgttttaaa cattcttatt attataatat    28740
taatataacc taaactgaag ttattcatcc caggtatcta atacatgtat ccaaagtaaa    28800
```

| | | | | |
|---|---|---|---|---|
| aatccaagga | atctgaacac | tttcatctgc | aaagctagga | ataggtttga cattttcact | 28860 |
| ccaagaaaaa | gttttttttt | gaaaatagaa | tagttgggat | gagaggtttc tttaaaagaa | 28920 |
| gactaactga | tcacattact | atgattctca | aagaagaaac | caaaacttca tataatacta | 28980 |
| taaagtaaat | ataaaatagt | tccttctata | gtatatttct | ataatgctac agtttaaaca | 29040 |
| gatcactctt | atataatact | attttgattt | tgatgtagaa | ttgcacaaat tgatatttct | 29100 |
| cctatgatct | gcagggtata | gcttaaagta | acaaaaacag | tcaaccacct ccatttaaca | 29160 |
| cacagtaaca | ctatgggact | agttttatta | cttccatttt | acaaatgagg aaactaaagc | 29220 |
| ttaaagatgt | gtaatacacc | gcccaaggtc | acacagctgg | taaaggtgga tttcatccca | 29280 |
| gacagttaca | gtcattgcca | tgggcacagc | tcctaactta | gtaactccat gtaactggta | 29340 |
| ctcagtgtag | ctgaattgaa | aggagagtaa | ggaagcaggt | tttacaggtc tacttgcact | 29400 |
| attcagagcc | cgagtgtgaa | tccctgctgt | gctgcttgga | gaagttactt aacctatgca | 29460 |
| aggttcattt | tgtaaatatt | ggaaatggag | tgataatacg | tacttcacca gaggatttaa | 29520 |
| tgagacctta | tacgatcctt | agttcagtac | ctgactagtg | cttcataaat gcttttttcat | 29580 |
| ccaatctgac | aatctccagc | ttgtaattgg | ggcatttaga | acatttaata tgattattgg | 29640 |
| catggtaggt | taaagctgtc | atcttgctgt | tttctatttg | ttcttttgt tttctcctta | 29700 |
| cttttggatt | ttttttattct | actatgtctt | ttctattgtc | ttattaacta tactctttga | 29760 |
| tttattttag | tggttgtttt | agggttatac | ctctttctaa | tttaccagtt tataaccagt | 29820 |
| ttatatacta | cttgacatat | agcttaagaa | acttactgtt | gttgtctttt tgctgttatg | 29880 |
| gtcttaacgt | ttttatttct | acaaacatta | taaactccac | actttattgt tttttaattt | 29940 |
| tacttataca | gtcaattatc | ttttaaagat | atttaaatat | aaacattcaa aacaccccaa | 30000 |
| t | | | | | 30001 |

<210> SEQ ID NO 3
<211> LENGTH: 1031
<212> TYPE: DNA
<213> ORGANISM: Homo sapiens

<400> SEQUENCE: 3

| | | | | |
|---|---|---|---|---|
| attcccggga | tacgtaacct | acggtgtccc | gctaggaaag | agaggtgcgt caaacagcga | 60 |
| caagttccgc | ccacgtaaaa | gatgacgctt | ggtgtgtcag | ccgtccctgc tgcccggttg | 120 |
| cttctctttt | gggggcgggg | tctagcaaga | gcaggtgtgg | gtttaggaga tatctccgga | 180 |
| gcatttggat | aatgtgacag | ttggaatgca | gtgatgtcga | ctctttgccc accgccatct | 240 |
| ccagctgttg | ccaagacaga | gattgcttta | agtggcaaat | cacctttatt agcagctact | 300 |
| tttgcttact | gggacaatat | tcttggtcct | agagtaaggc | acatttgggc tccaaagaca | 360 |
| gaacaggtac | ttctcagtga | tggagaaata | acttttcttg | ccaaccacac tctaaatgga | 420 |
| gaaatccttc | gaaatgcaga | gagtggtgct | atagatgtaa | agttttttgt cttgtctgaa | 480 |
| aagggagtga | ttattgtttc | attaatcttt | gatggaaact | ggaatgggga tcgcagcaca | 540 |
| tatggactat | caattatact | tccacagaca | gaacttagtt | tctacctccc acttcataga | 600 |
| gtgtgtgttg | atagattaac | acatataatc | cggaaaggaa | gaatatggat gcataaggaa | 660 |
| agacaagaaa | aatgtccaga | agattatctt | agaaggcaca | gagagaatgg aagatcaggg | 720 |
| tcagagtatt | attccaatgc | ttactggaga | agtgattcct | gtaatggaaa ctgctttcct | 780 |
| ctatgaaatt | ccccggggtt | cctggaggaa | atagatatag | gctgatacag ttacccaatg | 840 |

-continued

```
atggatgaat attgggggac cgcctggtca ttgaaaggct ttcttttctc caggaaagaa      900
atttttttcc ttttccataa aaagcttggg aatggaagac aacaattccc attcttttt       960 tgcgttccac ccctatgtga aacagaaat ttttgggaa acaacaacga aaaattta         1020 tcccgcgcgc a                                                          1031

<210> SEQ ID NO 4
<211> LENGTH: 3244
<212> TYPE: DNA
<213> ORGANISM: Homo sapiens
<220> FEATURE:
<221> NAME/KEY: CDS
<222> LOCATION: (108)..(1553)

<400> SEQUENCE: 4
gggcggggct gcggttgcgg tgcctgcgcc cgcggcggcg gaggcgcagg cggtggcgag       60
tggatatctc cggagcattt ggataatgtg acagttggaa tgcagtg atg tcg act       116
                                                   Met Ser Thr
                                                    1 ctt tgc cca ccg cca tct cca gct gtt gcc aag aca gag att gct tta        164
Leu Cys Pro Pro Pro Ser Pro Ala Val Ala Lys Thr Glu Ile Ala Leu
  5                  10                  15 agt ggc aaa tca cct tta tta gca gct act ttt gct tac tgg gac aat        212
Ser Gly Lys Ser Pro Leu Leu Ala Ala Thr Phe Ala Tyr Trp Asp Asn
 20                  25                  30                  35 att ctt ggt cct aga gta agg cac att tgg gct cca aag aca gaa cag        260
Ile Leu Gly Pro Arg Val Arg His Ile Trp Ala Pro Lys Thr Glu Gln
                 40                  45                  50 gta ctt ctc agt gat gga gaa ata act ttt ctt gcc aac cac act cta        308
Val Leu Leu Ser Asp Gly Glu Ile Thr Phe Leu Ala Asn His Thr Leu
             55                  60                  65 aat gga gaa atc ctt cga aat gca gag agt ggt gct ata gat gta aag        356
Asn Gly Glu Ile Leu Arg Asn Ala Glu Ser Gly Ala Ile Asp Val Lys
         70                  75                  80 ttt ttt gtc ttg tct gaa aag gga gtg att att gtt tca tta atc ttt        404
Phe Phe Val Leu Ser Glu Lys Gly Val Ile Ile Val Ser Leu Ile Phe
 85                  90                  95 gat gga aac tgg aat ggg gat cgc agc aca tat gga cta tca att ata        452
Asp Gly Asn Trp Asn Gly Asp Arg Ser Thr Tyr Gly Leu Ser Ile Ile
100                 105                 110                 115 ctt cca cag aca gaa ctt agt ttc tac ctc cca ctt cat aga gtg tgt        500
Leu Pro Gln Thr Glu Leu Ser Phe Tyr Leu Pro Leu His Arg Val Cys
                120                 125                 130 gtt gat aga tta aca cat ata atc cgg aaa gga aga ata tgg atg cat        548
Val Asp Arg Leu Thr His Ile Ile Arg Lys Gly Arg Ile Trp Met His
            135                 140                 145 aag gaa aga caa gaa aat gtc cag aag att atc tta gaa ggc aca gag        596
Lys Glu Arg Gln Glu Asn Val Gln Lys Ile Ile Leu Glu Gly Thr Glu
        150                 155                 160 aga atg gaa gat cag ggt cag agt att att cca atg ctt act gga gaa        644
Arg Met Glu Asp Gln Gly Gln Ser Ile Ile Pro Met Leu Thr Gly Glu
    165                 170                 175 gtg att cct gta atg gaa ctg ctt tca tct atg aaa tca cac agt gtt        692
Val Ile Pro Val Met Glu Leu Leu Ser Ser Met Lys Ser His Ser Val
180                 185                 190                 195 cct gaa gaa ata gat ata gct gat aca gta ctc aat gat gat gat att        740
Pro Glu Glu Ile Asp Ile Ala Asp Thr Val Leu Asn Asp Asp Asp Ile
                200                 205                 210 ggt gac agc tgt cat gaa ggc ttt ctt ctc aat gcc atc agc tca cac        788
Gly Asp Ser Cys His Glu Gly Phe Leu Leu Asn Ala Ile Ser Ser His
```

-continued

|  |  |  |  | 215 |  |  |  | 220 |  |  |  | 225 |  |  |  |  |
|---|---|---|---|---|---|---|---|---|---|---|---|---|---|---|---|---|
| ttg | caa | acc | tgt | ggc | tgt | tcc | gtt | gta | gta | ggt | agc | agt | gca | gag | aaa | 836 |
| Leu | Gln | Thr | Cys | Gly | Cys | Ser | Val | Val | Val | Gly | Ser | Ser | Ala | Glu | Lys |  |
|  |  | 230 |  |  |  | 235 |  |  |  | 240 |  |  |  |  |  |  |
| gta | aat | aag | ata | gtc | aga | aca | tta | tgc | ctt | ttt | ctg | act | cca | gca | gag | 884 |
| Val | Asn | Lys | Ile | Val | Arg | Thr | Leu | Cys | Leu | Phe | Leu | Thr | Pro | Ala | Glu |  |
| 245 |  |  |  |  | 250 |  |  |  |  | 255 |  |  |  |  |  |  |
| aga | aaa | tgc | tcc | agg | tta | tgt | gaa | gca | gaa | tca | tca | ttt | aaa | tat | gag | 932 |
| Arg | Lys | Cys | Ser | Arg | Leu | Cys | Glu | Ala | Glu | Ser | Ser | Phe | Lys | Tyr | Glu |  |
| 260 |  |  |  |  | 265 |  |  |  |  | 270 |  |  |  |  | 275 |  |
| tca | ggg | ctc | ttt | gta | caa | ggc | ctg | cta | aag | gat | tca | act | gga | agc | ttt | 980 |
| Ser | Gly | Leu | Phe | Val | Gln | Gly | Leu | Leu | Lys | Asp | Ser | Thr | Gly | Ser | Phe |  |
|  |  |  |  | 280 |  |  |  |  | 285 |  |  |  |  | 290 |  |  |
| gtg | ctg | cct | ttc | cgg | caa | gtc | atg | tat | gct | cca | tat | ccc | acc | aca | cac | 1028 |
| Val | Leu | Pro | Phe | Arg | Gln | Val | Met | Tyr | Ala | Pro | Tyr | Pro | Thr | Thr | His |  |
|  |  |  | 295 |  |  |  |  | 300 |  |  |  |  | 305 |  |  |  |
| ata | gat | gtg | gat | gtc | aat | act | gtg | aag | cag | atg | cca | ccc | tgt | cat | gaa | 1076 |
| Ile | Asp | Val | Asp | Val | Asn | Thr | Val | Lys | Gln | Met | Pro | Pro | Cys | His | Glu |  |
|  | 310 |  |  |  |  | 315 |  |  |  |  | 320 |  |  |  |  |  |
| cat | att | tat | aat | cag | cgt | aga | tac | atg | aga | tcc | gag | ctg | aca | gcc | ttc | 1124 |
| His | Ile | Tyr | Asn | Gln | Arg | Arg | Tyr | Met | Arg | Ser | Glu | Leu | Thr | Ala | Phe |  |
| 325 |  |  |  |  | 330 |  |  |  |  | 335 |  |  |  |  |  |  |
| tgg | aga | gcc | act | tca | gaa | gaa | gac | atg | gct | cag | gat | acg | atc | atc | tac | 1172 |
| Trp | Arg | Ala | Thr | Ser | Glu | Glu | Asp | Met | Ala | Gln | Asp | Thr | Ile | Ile | Tyr |  |
| 340 |  |  |  |  | 345 |  |  |  |  | 350 |  |  |  |  | 355 |  |
| act | gac | gaa | agc | ttt | act | cct | gat | ttg | aat | att | ttt | caa | gat | gtc | tta | 1220 |
| Thr | Asp | Glu | Ser | Phe | Thr | Pro | Asp | Leu | Asn | Ile | Phe | Gln | Asp | Val | Leu |  |
|  |  |  | 360 |  |  |  |  | 365 |  |  |  |  | 370 |  |  |  |
| cac | aga | gac | act | cta | gtg | aaa | gcc | ttc | ctg | gat | cag | gtc | ttt | cag | ctg | 1268 |
| His | Arg | Asp | Thr | Leu | Val | Lys | Ala | Phe | Leu | Asp | Gln | Val | Phe | Gln | Leu |  |
|  |  |  | 375 |  |  |  |  | 380 |  |  |  |  | 385 |  |  |  |
| aaa | cct | ggc | tta | tct | ctc | aga | agt | act | ttc | ctt | gca | cag | ttt | cta | ctt | 1316 |
| Lys | Pro | Gly | Leu | Ser | Leu | Arg | Ser | Thr | Phe | Leu | Ala | Gln | Phe | Leu | Leu |  |
|  |  | 390 |  |  |  |  | 395 |  |  |  |  | 400 |  |  |  |  |
| gtc | ctt | cac | aga | aaa | gcc | ttg | aca | cta | ata | aaa | tat | ata | gaa | gac | gat | 1364 |
| Val | Leu | His | Arg | Lys | Ala | Leu | Thr | Leu | Ile | Lys | Tyr | Ile | Glu | Asp | Asp |  |
|  | 405 |  |  |  |  | 410 |  |  |  |  | 415 |  |  |  |  |  |
| acg | cag | aag | gga | aaa | aag | ccc | ttt | aaa | tct | ctt | cgg | aac | ctg | aag | ata | 1412 |
| Thr | Gln | Lys | Gly | Lys | Lys | Pro | Phe | Lys | Ser | Leu | Arg | Asn | Leu | Lys | Ile |  |
| 420 |  |  |  |  | 425 |  |  |  |  | 430 |  |  |  |  | 435 |  |
| gac | ctt | gat | tta | aca | gca | gag | ggc | gat | ctt | aac | ata | ata | atg | gct | ctg | 1460 |
| Asp | Leu | Asp | Leu | Thr | Ala | Glu | Gly | Asp | Leu | Asn | Ile | Ile | Met | Ala | Leu |  |
|  |  |  | 440 |  |  |  |  | 445 |  |  |  |  | 450 |  |  |  |
| gct | gag | aaa | att | aaa | cca | ggc | cta | cac | tct | ttt | atc | ttt | gga | aga | cct | 1508 |
| Ala | Glu | Lys | Ile | Lys | Pro | Gly | Leu | His | Ser | Phe | Ile | Phe | Gly | Arg | Pro |  |
|  |  | 455 |  |  |  |  | 460 |  |  |  |  | 465 |  |  |  |  |
| ttc | tac | act | agt | gtg | caa | gaa | cga | gat | gtt | cta | atg | act | ttt | taa |  | 1553 |
| Phe | Tyr | Thr | Ser | Val | Gln | Glu | Arg | Asp | Val | Leu | Met | Thr | Phe |  |  |  |
| 470 |  |  |  |  | 475 |  |  |  |  | 480 |  |  |  |  |  |  | atgtgtaact taataagcct attccatcac aatcatgatc gctggtaaag tagctcagtg     1613 gtgtggggaa acgttcccct ggatcatact ccagaattct gctctcagca attgcagtta     1673 agtaagttac actacagttc tcacaagagc ctgtgagggg atgtcaggtg catcattaca     1733 ttgggtgtct cttttcctag atttatgctt ttgggataca gacctatgtt tacaatataa     1793 taaatattat tgctatcttt taaagatata ataataggat gtaaacttga ccacaactac     1853 tgttttttg aaatacatga ttcatggttt acatgtgtca aggtgaaatc tgagttggct     1913 tttacagata gttgactttc tatctttttgg cattctttgg tgtgtagaat tactgtaata     1973

```
cttctgcaat caactgaaaa ctagagcctt taaatgattt caattccaca gaaagaaagt    2033
gagcttgaac ataggatgag ctttagaaag aaaattgatc aagcagatgt ttaattggaa    2093
ttgattatta gatcctactt tgtggatttta gtccctggga ttcagtctgt agaaatgtct    2153
aatagttctc tatagtcctt gttcctggtg aaccacagtt agggtgtttt gtttatttta    2213
ttgttcttgc tattgttgat attctatgta gttgagctct gtaaaaggaa attgtatttt    2273
atgttttagt aattgttgcc aactttttaa attaattttc attattttg agccaaattg     2333 aaatgtgcac ctcctgtgcc ttttttctcc ttagaaaatc taattacttg gaacaagttc    2393
agatttcact ggtcagtcat tttcatcttg ttttcttctt gctaagtctt accatgtacc    2453
tgctttggca atcattgcaa ctctgagatt ataaaatgcc ttagagaata tactaactaa    2513
taagatcttt ttttcagaaa cagaaaatag ttccttgagt acttccttct tgcatttctg    2573
cctatgtttt tgaagttgtt gctgtttgcc tgcaataggc tataaggaat agcaggagaa    2633
attttactga agtgctgttt tcctaggtgc tactttggca gagctaagtt atcttttgtt    2693
ttcttaatgc gtttggacca ttttgctggc tataaaataa ctgattaata taattctaac    2753
acaatgttga cattgtagtt acacaaacac aaataaatat tttatttaaa attctggaag    2813
taatataaaa gggaaaatat atttataaga aagggataaa ggtaatagag cccttctgcc    2873
ccccacccac caaatttaca caacaaaatg acatgttcga atgtgaaagg tcataatagc    2933
tttcccatca tgaatcagaa agatgtggac agcttgatgt tttagacaac cactgaacta    2993
gatgactgtt gtactgtagc tcagtcattt aaaaaatata taaatactac cttgtagtgt    3053
cccatactgt gtttttttaca tggtagattc ttatttaagt gctaactggt tattttcttt    3113
ggctggttta ttgtactgtt atacagaatg taagttgtac agtgaaataa gttattaaag    3173
catgtgtaaa cattgttata tatcttttct cctaaatgga gaattttgaa taaaatatat    3233
ttgaaatttt g                                                         3244
```

<210> SEQ ID NO 5
<211> LENGTH: 761
<212> TYPE: DNA
<213> ORGANISM: Homo sapiens
<220> FEATURE:
<221> NAME/KEY: misc_feature
<222> LOCATION: (693)..(693)
<223> OTHER INFORMATION: n is a, c, g, or t
<220> FEATURE:
<221> NAME/KEY: misc_feature
<222> LOCATION: (722)..(722)
<223> OTHER INFORMATION: n is a, c, g, or t

<400> SEQUENCE: 5

```
cacgaggctt tgatatttct tacaacgaat ttcatgtgta gacccactaa acagaagcta     60
taaaagttgc atggtcaaat aagtctgaga agtctgcag atgatataat tcacctgaag     120
agtcacagta tgtagccaaa tgttaaaggt tttgagatgc catacagtaa atttaccaag    180
cattttctaa atttatttga ccacagaatc cctattttaa gcaacaactg ttacatccca    240
tggattccag gtgactaaag aatacttatt tcttaggata tgttttattg ataataacaa    300
ttaaaatttc agatatcttt cataagcaaa tcagtggtct ttttacttca tgttttaatg    360
ctaaaatatt ttctttata gatagtcaga acattatgcc tttttctgac tccagcagag    420
agaaaatgct ccaggttatg tgaagcagaa tcatcattta aatatgagtc agggctcttt    480
gtacaaggcc tgctaaagga ttcaactgga agctttgtgc tgcctttccg gcaagtcatg    540
```

```
tatgctccat atcccaccac acacatagat gtggatgtca atactgtgaa gcagatgcca      600
ccctgtcatg aacatattta taatcagcgt agatacatga gatccgagct gacagccttc      660
tggagagcca cttcagaaga agacatggct cangatacga tcatctacac tgacgaaagc      720
tntactcctg atttgaatat ttttcaagat gtcttacaca g                          761
```

```
<210> SEQ ID NO 6
<211> LENGTH: 1901
<212> TYPE: DNA
<213> ORGANISM: Homo sapiens
<220> FEATURE:
<221> NAME/KEY: CDS
<222> LOCATION: (125)..(793)

<400> SEQUENCE: 6
acgtaaccta cggtgtcccg ctaggaaaga gaggtgcgtc aaacagcgac aagttccgcc      60
cacgtaaaag atgacgcttg atatctccgg agcatttgga taatgtgaca gttggaatgc     120 agtg atg tcg act ctt tgc cca ccg cca tct cca gct gtt gcc aag aca      169
     Met Ser Thr Leu Cys Pro Pro Pro Ser Pro Ala Val Ala Lys Thr
     1               5                   10                  15 gag att gct tta agt ggc aaa tca cct tta tta gca gct act ttt gct      217
Glu Ile Ala Leu Ser Gly Lys Ser Pro Leu Leu Ala Ala Thr Phe Ala
                20                  25                  30 tac tgg gac aat att ctt ggt cct aga gta agg cac att tgg gct cca      265
Tyr Trp Asp Asn Ile Leu Gly Pro Arg Val Arg His Ile Trp Ala Pro
            35                  40                  45 aag aca gaa cag gta ctt ctc agt gat gga gaa ata act ttt ctt gcc      313
Lys Thr Glu Gln Val Leu Leu Ser Asp Gly Glu Ile Thr Phe Leu Ala
        50                  55                  60 aac cac act cta aat gga gaa atc ctt cga aat gca gag agt ggt gct      361
Asn His Thr Leu Asn Gly Glu Ile Leu Arg Asn Ala Glu Ser Gly Ala
    65                  70                  75 ata gat gta aag ttt ttt gtc ttg tct gaa aag gga gtg att att gtt      409
Ile Asp Val Lys Phe Phe Val Leu Ser Glu Lys Gly Val Ile Ile Val
80                  85                  90                  95 tca tta atc ttt gat gga aac tgg aat ggg gat cgc agc aca tat gga      457
Ser Leu Ile Phe Asp Gly Asn Trp Asn Gly Asp Arg Ser Thr Tyr Gly
                100                 105                 110 cta tca att ata ctt cca cag aca gaa ctt agt ttc tac ctc cca ctt      505
Leu Ser Ile Ile Leu Pro Gln Thr Glu Leu Ser Phe Tyr Leu Pro Leu
            115                 120                 125 cat aga gtg tgt gtt gat aga tta aca cat ata atc cgg aaa gga aga      553
His Arg Val Cys Val Asp Arg Leu Thr His Ile Ile Arg Lys Gly Arg
        130                 135                 140 ata tgg atg cat aag gaa aga caa gaa aat gtc cag aag att atc tta      601
Ile Trp Met His Lys Glu Arg Gln Glu Asn Val Gln Lys Ile Ile Leu
    145                 150                 155 gaa ggc aca gag aga atg gaa gat cag ggt cag agt att att cca atg      649
Glu Gly Thr Glu Arg Met Glu Asp Gln Gly Gln Ser Ile Ile Pro Met
160                 165                 170                 175 ctt act gga gaa gtg att cct gta atg gaa ctg ctt tca tct atg aaa      697
Leu Thr Gly Glu Val Ile Pro Val Met Glu Leu Leu Ser Ser Met Lys
                180                 185                 190 tca cac agt gtt cct gaa gaa ata gat ata gct gat aca gta ctc aat      745
Ser His Ser Val Pro Glu Glu Ile Asp Ile Ala Asp Thr Val Leu Asn
            195                 200                 205 gat gat gat att ggt gac agc tgt cat gaa ggc ttt ctt ctc aag taa      793
Asp Asp Asp Ile Gly Asp Ser Cys His Glu Gly Phe Leu Leu Lys
        210                 215                 220
```

| | |
|---|---|
| gaatttttct tttcataaaa gctggatgaa gcagatacca tcttatgctc acctatgaca | 853 |
| agatttggaa gaaagaaaat aacagactgt ctacttagat tgttctaggg acattacgta | 913 |
| tttgaactgt tgcttaaatt tgtgttattt ttcactcatt atatttctat atatatttgg | 973 |
| tgttattcca tttgctattt aaagaaaccg agtttccatc ccagacaaga aatcatggcc | 1033 |
| ccttgcttga ttctggtttc ttgttttact tctcattaaa gctaacagaa tcctttcata | 1093 |
| ttaagttgta ctgtagatga acttaagtta tttaggcgta gaacaaaatt attcatattt | 1153 |
| atactgatct ttttccatcc agcagtggag tttagtactt aagagtttgt gcccttaaac | 1213 |
| cagactccct ggattaatgc tgtgtacccg tgggcaaggt gcctgaattc tctatacacc | 1273 |
| tatttcctca tctgtaaaat ggcaataata gtaatagtac ctaatgtgta gggttgttat | 1333 |
| aagcattgag taagataaat aatataaagc acttagaaca gtgcctggaa cataaaaaca | 1393 |
| cttaataata gctcatagct aacatttcct atttacattt cttctagaaa tagccagtat | 1453 |
| ttgttgagtg cctacatgtt agttccttta ctagttgctt tacatgtatt atcttatatt | 1513 |
| ctgttttaaa gtttcttcac agttacagat tttcatgaaa ttttactttt aataaaagag | 1573 |
| aagtaaaagt ataaagtatt cacttttatg ttcacagtct tttcctttag gctcatgatg | 1633 |
| gagtatcaga ggcatgagtg tgtttaacct aagagcctta atggcttgaa tcagaagcac | 1693 |
| tttagtcctg tatctgttca gtgtcagcct ttcatacatc attttaaatc ccatttgact | 1753 |
| ttaagtaagt cacttaatct ctctacatgt caatttcttc agctataaaa tgatggtatt | 1813 |
| tcaataaata aatacattaa ttaaatgata ttatactgac taattgggct gttttaaggc | 1873 |
| aaaaaaaaaa aaaaaaaaa aaaaaaaa | 1901 |

<210> SEQ ID NO 7
<211> LENGTH: 562
<212> TYPE: DNA
<213> ORGANISM: Homo sapiens
<220> FEATURE:
<221> NAME/KEY: misc_feature
<222> LOCATION: (166)..(166)
<223> OTHER INFORMATION: n is a, c, g, or t

<400> SEQUENCE: 7

| | |
|---|---|
| agacgtaacc tacggtgtcc cgctaggaaa gagagatatc tccggagcat ttggataatg | 60 |
| tgacagttgg aatgcagtga tgtcgactct ttgcccaccg ccatctccag ctgttgccaa | 120 |
| gacagagatt gctttaagtg gcaaatcacc tttattagca gctacntttt gcttactggg | 180 |
| acaatattct tggtcctaga gtaaggcaca tttgggctcc aaagacagaa caggtacttc | 240 |
| tcagtgatgg agaaataact tttcttgcca accacactct aaatggagaa atccttcgaa | 300 |
| atgcagagag tggtgctata gatgtaaagt tttttgtctt gtctgaaaag ggagtgatta | 360 |
| ttgtttcatt aatctttgat ggaaactgga atggggatcg cagcacatat ggactatcaa | 420 |
| ttatacttcc acagacagaa cttagtttct acctcccact tcatagagtg tgtgttgata | 480 |
| gattaacaca tataatccgg aaaggaagaa tatggatgca taaggaaaga caagaaaatg | 540 |
| tccagaagat tatcttagaa gg | 562 |

<210> SEQ ID NO 8
<211> LENGTH: 798
<212> TYPE: DNA
<213> ORGANISM: Homo sapiens
<220> FEATURE:
<221> NAME/KEY: CDS
<222> LOCATION: (81)..(590)

<400> SEQUENCE: 8

```
gggctctctt tgggggcgg ggtctagcaa gagcagatat ctccggagca tttggataat        60
gtgacagttg gaatgcagtg atg tcg act ctt tgc cca ccg cca tct cca gct      113
                     Met Ser Thr Leu Cys Pro Pro Pro Ser Pro Ala
                      1               5                  10 gtt gcc aag aca gag att gct tta agt ggc aaa tca cct tta tta gca        161
Val Ala Lys Thr Glu Ile Ala Leu Ser Gly Lys Ser Pro Leu Leu Ala
         15                  20                  25 gct act ttt gct tac tgg gac aat att ctt ggt cct aga gta agg cac        209
Ala Thr Phe Ala Tyr Trp Asp Asn Ile Leu Gly Pro Arg Val Arg His
     30                  35                  40 att tgg gct cca aag aca gaa cag gta ctt ctc agt gat gga gaa ata        257
Ile Trp Ala Pro Lys Thr Glu Gln Val Leu Leu Ser Asp Gly Glu Ile
 45                  50                  55 act ttt ctt gcc aac cac act cta aat gga gaa atc ctt cga aat gca        305
Thr Phe Leu Ala Asn His Thr Leu Asn Gly Glu Ile Leu Arg Asn Ala
 60                  65                  70                  75 gag agt ggt gct ata gat gta aag ttt ttt gtc ttg tct gaa aag gga        353
Glu Ser Gly Ala Ile Asp Val Lys Phe Phe Val Leu Ser Glu Lys Gly
             80                  85                  90 gtg att att gtt tca tta atc ttt gat gga aac tgg aat ggg gat cgc        401
Val Ile Ile Val Ser Leu Ile Phe Asp Gly Asn Trp Asn Gly Asp Arg
         95                 100                 105 agc aca tat gga cta tca att ata ctt cca cag aca gaa ctt agt ttc        449
Ser Thr Tyr Gly Leu Ser Ile Ile Leu Pro Gln Thr Glu Leu Ser Phe
    110                 115                 120 tac ctc cca ctt cat aga gtg tgt gtt gat aga tta aca cat ata atc        497
Tyr Leu Pro Leu His Arg Val Cys Val Asp Arg Leu Thr His Ile Ile
125                 130                 135 cgg aaa gga aga ata tgg atg cat aag gaa aga caa gaa aat gtc cag        545
Arg Lys Gly Arg Ile Trp Met His Lys Glu Arg Gln Glu Asn Val Gln
140                 145                 150                 155 aag att atc tta gaa ggc aca gag aga atg gaa gat cag ggt cag            590
Lys Ile Ile Leu Glu Gly Thr Glu Arg Met Glu Asp Gln Gly Gln
                160                 165                 170 agtattattc caatgcttac tggagaagtg attcctgtaa tgggactgct ttcatctatg      650
aaatcacaca gtgttcctga gaaatagat ataagctgata cagtactcca tgatgatgat      710
atttggtgac agctgtcatg aaaggctttc ttctcaagta ggatttttt cttttcataa       770 aagctgggat gaagccagat tcccatct                                          798

<210> SEQ ID NO 9
<211> LENGTH: 169
<212> TYPE: DNA
<213> ORGANISM: Homo sapiens

<400> SEQUENCE: 9
aaacagcgac aagttccgcc cacgtaaaag atgatgcttg gtgtgtcagc cgtccctgct       60
gcccggttgc ttctcttttg ggggcggggt ctagcaagag cagatatctc cggagcattt      120
ggataatgtg acagttggaa tgcggtgatg tcgactcttt gcccaccgc                  169

<210> SEQ ID NO 10
<211> LENGTH: 176
<212> TYPE: DNA
<213> ORGANISM: Homo sapiens

<400> SEQUENCE: 10
aaaacgtcat cgcacataga aaacagacag acgtaaccta cggtgtcccg ctaggaaaga      60
```
gaggtgcgtc aaacagcgac aagttccgcc cacgtaaaag atgacgcttg atatctccgg    120
agcatttgga taatgtgaca gttggaatgc agtgatgtcg actctttgcc caccgc        176

<210> SEQ ID NO 11
<211> LENGTH: 38001
<212> TYPE: DNA
<213> ORGANISM: Mus musculus

<400> SEQUENCE: 11
caaacacaca cacacacaca cacacacaca cacacacaca cacacacaca cacacactgg    60
catatcaagt ctctgttagg ctaggcgcat cctctcccac tgaggtcaga caagactgcc   120
cagctagaag aacatatccc acggacaggc aacagctttt gggacagcca cgctccagtt   180
gtttgggact cataaaagac taaactcaca cctgctacaa aagtgcaggg aggcctaggt   240
ccagcctgtg tgtgctcttt gcttagtggt gtctctgaga gccctaagga tcaaagtttg   300
ttgactctgt tggtcttcct gtggagttcc tatcccttc gtcccctcc ccaccctgca     360 atctttccct caactcttct ttaggcctgg tggtggtggt gtggtggcat ggaggaggtg    420
gtggaggggg tgggggtctt taatcccggt tcttgtgaga ccgaagcagg gacgatttcg   480
gagctctgtg agtttgaggc cagcctggtc tatagatcta gttccaggac agtcagagct   540
acatagagaa accctgcccc gaggggggggg gggcgcgggg aatggttaaa gattattgca   600
ggacccagct gatctgtgga agaggtaacg ggtgtttatg ttttcgaaa ctcattgaac    660 aatgcacttc aattgtgcgc actttagaaa tataaagcca ccacgcgaaa agctgcgccc   720
caacttaaag gcaatttcca aggtacttct gggtccttgc ggttcagtgg ctgtctaggt   780
tcagaaacga aactggatcc ccgcccgcc ccccgcccc ccccctcccc agcgccctga     840
ggcagtttcg atttcctatg gccagccggc taggcagctt tttcatcggg actccttgga   900
aagtccccac ttcgttcatc tctggcggat ttgcggagc cagggcgctc atcgatcgcc    960
tggagccaca gaatgacagc ggagcagcgg cagaatctgc aagcattcag agactatatc  1020
aagaagattc tggaccccac ctacatcctc agctacatga gttcctggct cgaggatggt  1080
gagtggtccc caactggggc tctcaggctc tccaccttag cgaggggaaa acatcactca  1140
gatcagaaac aattgaaggc tctgcccccc cccctccccc gcgctgtcct taagttaatt  1200
tgtgtaaccc ggtgtatgtg agactcccag gccatattag agtagacagc ataggatttt  1260
gatggtcagg aacaaaattc ctgcaagctg tagtaacttg cataaggatg ccactctttt  1320
ctttctttca atgctgggga aatagtttgt ttctcttatt tacaccttct agactgctgt  1380
gtgcctccct ttgtcctgtc atgagaaact gagaaatcag aatgcgcccg cccctcctta  1440
gattcctgta cagagcaaag agcaaggctt tgggctcggg ccaaaggtgg aggtgggggc  1500
cgcaggaagc aagaggactg actgacacgc acatttctgt caaaggatgt tgctcacagg  1560
aagtccgtgg aagaaaactt tctccagact ccgtgtgttc agagtttaac acagttgttc  1620
atatctagct ttggggattt gattggtgga taatagactc tttgtaaatt gcactgggtg  1680
tttccacctg agcaaacaga cctccccacc tcacccccac cccagggag aagggagagg    1740 gcgtttgaag gggtgaccga gggcgtgcgg cagctacttt tcattttgcc agttaaagcc  1800
tagatgtctt tcctggcgtt ggacgacggt ggcaactgca ggttaattct gactctcttg  1860
agttccgaag cctaacaggc tatgcagaga ggagtaaaag agcactaccc agggctaccc  1920
acatcccggt tgtgttagag agaagcagca aaaagccct aatgattggg ggcggggtct    1980

| | | | | |
|---|---|---|---|---|
| gaggagagga | aacccaccca | agaggtttct | taacaccagg | gtcacttgcc | tttcaatcct | 2040 |
| ttaatctgat | ctttagtcat | ttacattagc | atacaaagta | actagtttca | atactgaaac | 2100 |
| aaagtaacta | gtttgttcag | ccattcctgc | cattgctctt | tgttcttatt | taattgcctc | 2160 |
| ttctgtggct | cttccacccc | ctttacctgt | ccctctctgg | atgccctccc | ccccaaatgg | 2220 |
| taccccgttc | tgctttctta | taacatgagg | ttcatcacac | tccctccctc | cctccctccc | 2280 |
| ccatttaaag | tatcatcctt | tcctctcagg | gtgcctgttt | tagtttcatg | aattttaggg | 2340 |
| ttttggtttt | ttgtctgttt | agttatgaga | ttttttttaaa | aatgtggatt | atgttgaatt | 2400 |
| tgtagattgt | tcttggtgct | agaggccttt | ttatagtatt | atttccaccc | atcttgggag | 2460 |
| atctttctga | aatcttccag | tgtcttcaag | aattttttt | tcccactgcc | ttagaagttt | 2520 |
| gcattgtagc | tatcgttcac | ctcttttggtt | agggtttgtt | gttatttgtt | tgtttgaggc | 2580 |
| tattgtgaat | agaactccct | ccttccccca | tatctttctg | ggccaggttg | ttcttagtat | 2640 |
| gtaagtaagc | tactggtttc | tgtatgttta | tttagaaccc | tgcctcttgg | ttgactttt | 2700 |
| atgagggctg | agagtttgtg | gtagtctttg | ggggtctttt | ataggattat | ataagaatca | 2760 |
| tttgactcat | tccttcccta | tttgtctaac | tttgtttgt | ttgtttgttt | gttttttga | 2820 |
| gacagggttt | ctctgtatag | ccctggcagt | cctggaactc | actttgtaga | ccaggctggc | 2880 |
| ctcgaactca | gaaatctgcc | tgcctctgcc | tcccgagtgc | tgggattaaa | ggcgtgcacc | 2940 |
| accacacccg | gccatcattt | ccaagttaaa | gatttgatct | acattagacg | ccgccacgca | 3000 |
| gaaaaccttg | agacttggtg | gaaaggccaa | aggccattaa | aataaattt | cttttttctt | 3060 |
| tcttccattc | tttcctttat | tccttccttc | ctttcttttt | gttttcttc | ttttctttt | 3120 |
| cctttttcct | gagacagggt | ttctctgtat | agccctggca | tcctggaact | cactctgtag | 3180 |
| accaggctgg | cctcgaactc | agaaatccac | cagcctttgc | ctcccaagtg | ttgggattaa | 3240 |
| aggcattcgc | caccactgcc | caaatatttt | atttatttat | ttatttattt | atttttatat | 3300 |
| atgtgatgag | tacactggaa | attccatcaa | aaagagcagg | tttgactggt | gtcactagat | 3360 |
| ttactattga | tagggatccc | taaaggagag | ctaaggtaaa | gggctctccc | tctcctaggt | 3420 |
| cttctgcata | ccttccttga | gtgttctggg | ccagatctcc | taagctctaa | gaatgtgctg | 3480 |
| aaaacacact | gggaactggc | tccctccttg | ggaatttgta | ctccctctgc | tgtgggaaac | 3540 |
| ttggatataa | gaggctacag | gaggacagtg | agttataccc | caggcacaga | gttagcgtgt | 3600 |
| acattcaaaa | cgcataccat | tttgaaagta | gcagctgcta | gcatttcctg | tcacctggtc | 3660 |
| aacctggtct | ctttagctgc | cccaccccctt | ccacttttct | gctgtgtttc | ttttactctc | 3720 |
| ttagcaaaaa | ttggaatgaa | agaccacaaa | tgtatttgta | attcaaaatg | cttgctgcat | 3780 |
| cagctatact | cgttactgtt | gccatagggc | gttcattccc | acccaccccc | aacccccttag | 3840 |
| tccagcagtt | gcttcagagt | tttgaagaag | aggaggaagc | ctttcttctt | ccatgtgaca | 3900 |
| ccctccactg | cgacttctgc | ttactgtggg | gaacttgagt | ggaggacggg | agtgtgcata | 3960 |
| gatgaaagag | tggaggacgg | gagtgtgcat | agatgaagga | gtggaggacg | ggagtgtgca | 4020 |
| tacatgaagg | agtggaggac | gggagtgtgc | atacatgaag | gagtggagga | cgggagtgtg | 4080 |
| catacatgaa | ggagtggagg | acgggagtgt | gcatacatga | aggagtggag | gatgggagtg | 4140 |
| tgcatacatg | aaggagtgga | ggacgggagt | gtgcatacat | gaaggagtgg | aggacgggag | 4200 |
| tgtgcataca | tgaaggagag | gaggacggga | gtgtgcatag | atgaaggaga | ggaggacggg | 4260 |
| agtgtgcata | gatgaaggag | aggaggacgg | gagtgtgcat | agatgaagga | gaggaggacg | 4320 |
| ggagtgtgca | tagatgaagg | agaggaggac | gggagtgtgc | atagatgaag | gagtggagga | 4380 |

```
cgggagtgtg catacatgaa ggagtggagg acgggagtgt gcatacatga aggagtggag   4440
gacgggagtg tgcatacatg aaggagtgga ggacgggagt gtgcatacat gaaggagtgg   4500
aggacgggag tgtgcataca tgaaggagag gaggacggga gtgtgcatag atgaaggaga   4560
ggaggacggg agtgtgcata gatgaaggag aggaggacgg gagtgtgcat agatgaagga   4620
gaggaggacg ggagtgtgca tacatgaagg aaaggaggac gggagtgtgc atagatgaag   4680
gagtggagga cgggagtgtg catacatgaa ggagtggagg acgggagtgt gcatacatga   4740
aggagtggag gacgggagtg tgcatatgaa ggagtggagg acgggagtgt gcatacatga   4800
aggagtggag gacgggagtg tgcatagatg aaggagagga ggacgggagt gtgcatagat   4860
gaaggagagg aggacgggag agtgcataga tgaaggagtg gaggacggga gtgtgcatac   4920
atgaaggagt ggaggacggg agtgtgcata catgaaggag tggaggacgg gagtgtgcat   4980
agatgaagga gaggaggacg ggagtgtgca tagatgaagg agaggaggac gggagagtgc   5040
atagatgaag gagtggagga cgggagtgtg catagatgaa ggagtggagg acagagtgt   5100 gcatacatga aggagtggag gacgggagtg tgcgaggatg gatgagtgga gtctgctgcc   5160
tctcaaaggt cttctggttc catgagttgt tatgactccc agaccacat gggaaggtct   5220 ggtctgttat cttccagtga ctagtgcttc tgcaggctac tcacttgccc ttgcttctgt   5280
ttgcagagga ggtgcagtac attcaggctg agaagaacaa caagggccca atggaagctg   5340
cctcactctt cctccagtac ctgttgaagc tgcagtcaga gggctggttc caggcctttt   5400
tggatgccct gtaccatgca ggttggttcc ttcttcttcc tcacagttca gagtacttca   5460
ctctgctgcc tcagaaggct gagggagaa aagtgactcg ttctgtgaca tctgtgtgtg   5520
gcttctgcct caggcgggaa atgtaaagac tattttgaat cagataagag aatggtttat   5580
accagaaata tccaaagcaa tctacagagt tgtaactact aggagaggtg acaatattag   5640
tagcatgccg gtatctttca agaggagaac gagtaaataa atcggtttta taatgtttac   5700
agtgctccat tatactgcaa tgaagcgtgt ggacatgtct gtaaatgaca acccagctga   5760
actgtaggca cgcagcattt aaatttgaat atcataaact ataatagcta taagttccaa   5820
catgagtcaa actaaacata tagggaagga aactggatct tgggcgaccc tggctgacca   5880
gtcctgggga gtaagcttaa taaactctcc ctgtctgact gagatcggtg tcctgtggtt   5940
tgtgaggcaa ttcctggact ctaacactta ggcaattaca tttcttgccc ctctgccact   6000
ctagcttatt cactggtgaa agaaggagaa tactttagtg ttaccaacaa tggggggggg   6060
ggggcggggg atgggaaatg ggaaaagca ggcccggccc agtgtagtaa gaaagaaaca   6120
ccaaagaaag ccaagggctc ctgttgcttt cattgtattg gagtgtttgt cagtcggctg   6180
ggggatgggg tggggggtgg ggaagcacac ctttaatccc agctctgggg aggcagaggc   6240
aggcagatcc ctgtgagctc caccagtcat ggctggcctc agcaagaact gtatccatca   6300
catcctaaca caggtgtgtt gaattaacat ggtactgtta aagcaaacac gctgccttcc   6360
tcgggtgctg cggtccctag gaagccacac attggcagca tgttggcagc agttgtataa   6420
aaactaatgc ttttttttcc ttttctttt aattcggtaa aagggtttaa atgtcatttg   6480
ttataaaact tggtttcctg ctatttccag gattaacaat tgacttattc tttctatttc   6540
ctgctttata gaccatcatt ttgatacatt atctatttgc atctcagtga tacatgctta   6600
tcttaccctt ttatttcgtt ttaagaattg tgtgtgtgtg tgtgtgtgtg tgtgtgtgtg   6660
tgtgtgtgtg tgtgtgtgtg tgtctgagag tgggcatgca tttatgagtg cattgcctag   6720
```

```
aggtcagaca ttcccctgga gctggagtta atggcagttg tgagggactg acgtgggtgc    6780
tgggatctga ccccagtccc ctgcaagaac acgatgaacc ttacttgcta agccatctcc    6840 ccagcccttag ctgttgcag ttactctcca ttccaaataa gccctggcaa tgaaaacaag    6900
acttaattca tatgaataca tgctgtgcac ctagattggg cagatctacc gctacactac    6960
catcttctcc atctatgaga ctccccctttt tttttttctt ttttctttt ttgtggtttt    7020 ggttttttga acagggtttt ctctgtatag ccctggctgt cctggaactc actttgtaga    7080
ccaggctggc ctcgaactca gaaatccgcc tgcctctgcc tcccaagtgc tgggaattaa    7140
ggcgtgcgcc accaggcggt ttctccaggc tgtgtgcttc tgctccactt ttcttcctcc    7200
tcctctgtgg tatcctctcc ctcttcctct ttctccttct ctcttcccac cttcctctcc    7260 aacttcccctt tatcagccca atcaccagct ctcctttatt ttactaattg aggtgggaag    7320
caggtttaca ggaaatcacc ggagtgctga ctcattcctt gttcgcagcc actcaatgca    7380
gaatggaatt accatcaaat ataattagcc ccagggctat ccacaacact tacctagcac    7440
atcaaatggc ccagcagggg atcaagagaa aaggaaactc aacttctgct tattttcctc    7500
atctcttatg tagccccatc agagaagctg ttgttttcct tttgtgggct ctaactaatt    7560
tgaatattat atttaagatc tattctctta agtaaaaatg gcacagctaa ctttaactgt    7620
aaaattatat gaggtttact aggaaaagtc ttgagtttaa gcaagaaagg gaattttaaa    7680
acatttgtat tggaacataa gtgctggaac atctctcttt gcaagtgagg tgctttgtgt    7740
gtacaaccct aagagtttct tttttttttt ttttttaattt atttacttca tatttcagac    7800
agatctcatt tcaggtggtt gtgagccacc atgtggttgc tgggatttga actcaggacc    7860
tctggaagag cagtcagtgc tcctctgcgc tgagccatct ctccagcccc cctaagagtt    7920
tcataaagga atagtctgca ttaataaatt cagaaaaggc tcagaatata aagccaatat    7980
catcaagtag gtttccagtt tatgtattaa caaataatgc aaaaaagatt ttaagcaagc    8040
gattcctttt ataacagcac caagaacaat aaagttagga atgccagtgc tcctaactgc    8100
tgaaccacct cagcaatgca aacttttaca tcttagcact aagtccagct cctaattcgt    8160
gaatgtaaga tgtcattcat gtccgtgtcc ctatggttcg tttcagaagt ggtttatggt    8220
cttcgggtca taggtctttc ccctgctcag cttttgcttat tcctaacttt atttaaagtt    8280
ctcactgttg ttataaaagg aatcacttgg ggctggcgag atggctcagt gggtaagagc    8340
acccgactgc tcttccgaag gtcctgagtt caaatcccag caaccacatg gtggctcaca    8400
accatccgta acgagatctg actccctctt ctggagtgtc ggaagacagc tacagtgtat    8460
ttacatataa taaataaata aataaataaa tcttcaaaaa aattctaaaa aaatatggaa    8520 aaaaaggaa tcacttagtt aaaaatctca ttcctagccg gttgtggtgg cataccttt    8580 taatcccagc acttgggtgg cagaggcagg cggatttcta gtttgaggt ctacaaagtg    8640 agttccaggt ctctgaaaac cacaaaaaaa aaaaaaaaa atagcactgg ctgctcttcc    8700
gaaggttctg agttcaaatc cctccaacca catagtggct cacaaccata tgtaatggga    8760
tctgatgccc tcttctggtg tgtctgaaga cagtaacagt gtacttacat ataataaata    8820
aataaatctt tgggtgggag tgagcggggc tggagagaga aggaaaagta tctgaagaca    8880
actacagtgt acttacatat aatagataaa taaatctta aaaaaatcaa taaatgaaag    8940
atgccaatat tacccagagt tggcacagtg ataccttttca taatgccaaa ttttggtggc    9000
aggattgttt gtttattaaa caggaataga aaaatttact ctcaaatttg tatgaaatct    9060
taaatggtca aaatattgga aagagaaact cacttggaaa ccttggggga cttatacttc    9120
```

```
ctggtgtcaa aacagtacag aacctccata aagccagata attagaccat tagcccagaa    9180
gtaaactctg aaggatatgg ccaaaggttc ttcaacaagg gtaccatgac cacccaaaag    9240
ggggaaaaaa aacccagtcc ctttaatatg aaaatacatt ggggtaagtg ggtatacata    9300
tgggaatgag aggtatcagg cataatcttg tgctatgatg tgaatttgaa atgttctcat    9360
cacattcatg ttttgagtgc ttggtcccca gcttgtgggg ttttaggagg tagagcctag    9420
ctagccaaag taacacgtgt atacgttcat gcatgtgtgc acacaggtat gagggtactt    9480
gtgtgtagcc cagaggctga cattcagtgt cttccttagg agctctccac cgtatgtttt    9540
tgggaatgga tctctcatta gacccagaat ttaccctctc gggctcgact ggctgggatt    9600
atagggtcat gctgctacac ttggcttttt acatgatagc tggggacagg aactcaggtc    9660
ccagccttgt gtggtgagca cttttctact aagcaccttc ttggtcctgg agctattttg    9720
attgttttag tttttgggt ctatagggg gagaaaaaaa aaaaaccac attgtcttcc    9780 cagggccttg aatgaagtaa atgagggtct gagaggcagg cacgcctggt ggatctgtcc    9840
aaaaacccca gagtacggca ttcttggatt cttttagtca gaagtcattt tccttctcca    9900
tttgcccatt gacttaatct tttcttggaa tggtgtggaa ggaaacactt ttcaagggca    9960
ggatgtaaga tttgtatttc ctctggtctt ctttactgtt tcctcttgag aagataaaca   10020
tgatgaattt gactaattta aaagtaaatt gagatgacaa agagatggct ctgtgattaa   10080
gagcacttgc tgatcttgca gaggacccag gtttggttcc tagacttaca tggtagctca   10140
caaccatctg taacttcagt tccaggaatc tgaccctctc ttctgctctc caaagatacc   10200
agacacactc acgatacaca gacacatgca aagtaaaata gaaataaata ttaaaaaaaa   10260
atatattgtg ggttgttgtt aaagtgcgtg aggggcattt tgaagatttt attctaaggt   10320
caaatacaag gcctcatatc tgtccttagg acttgaccct gaaagataat gaatttagg    10380 agacctaaac tgttgggtac caaaaatgag tattactccc attttggaaa atcatgaata   10440
gctgtattag ttgactttaa ctactgtgag taaatgcccg aggaaataaa aagcagaaaa   10500
atgagagcca agaggatctg tagcttctgc acccgtgcgt ggtgaggcag ggcaccatgg   10560
cgggagcatg tgggaaaagc cgcactttct ggtagacagg tggcaaaggg tgccgggcag   10620
gggccctgga caagatgcat tcttcaaagc acatctccag tgactcactt ctcccagaga   10680
gggtacagtt ctcagttgct ccttctgtat gaactcaatg tgctgccagt ggtgacgcca   10740
ggactcgaag gatgtggtca ccaggtcccg cagggtgtgg tcacctctaa agactgtcac   10800
cagctggtgt ccaagcctgc aacctgtcag cctcatggtc tggctcccca gactgtccag   10860
tgactgaggc catttgcaga tggttttcag ttcccttgcc actgatttga acaggattcc   10920
catgattttg acttcaaagc attttatgt tggatttgct taagaaatcc ccatttctct   10980 tttcttttc aggttactgt ggactttgtg aagccatcga agttgggac tttcaaaaaa    11040 ttgaaaagtt agaggaacac agattacttt taagacgttt agaaccagaa tttaaggcca   11100
cagttgatcc aaatgatatc ctttctgaac tatccgaatg tttgattaat caggaatgtg   11160
aagaaatcag acaggtaaac caatgccagg tactaaattt gaagaaaaat gcagagacat   11220
tggaaatgcc cattttctg tcttgtttta ggcccaagga taattgaaac ccataaaagc   11280
tctcatctag cagatataat gactagaata gaatttttaa agtgaatggg gtaattttg    11340 tgctagacta ttagaaaatt attaaccta tttgcagtta aagttgcccc cttactttaa    11400
aaaaaatagt ggtttatgca taatgcaaat cacaccaaac agtgcaacaa ttaaaaggaa   11460
```

```
aaatatgtca ggctcttggg catagataca tttattacag tctcgcagtc acttaactag    11520
tgatgtgatg ccaggcagtt ctctaagcat ctgtggggtt tttgttgttg ttgttgttgt    11580
tgtttgtttg tttgtttttc atgtctaaag taagaaaatt tatcttttgt tttttgtttt    11640 tttgttttt tagatttctt tattttattt tattatatgt gagtacactg tagctgtctt    11700
cagacactcc agaagagggc gtcagatctt gttacggatg gttgtgagcc actatgtggt    11760
tgctgggatt tgaactcagg accttcggaa gaacagtcgg tgctctcaac ccctgagcca    11820
tctctccagc ccccttttgt ttttgttttt gttttgttt ttgttttttt gtttgtttgg    11880
tttttttgtc gttgttgttg tttgtttgtt tgttttttc gagatagggt ttctctgtgt    11940
agccctggct gtcctggaac tcactctgta gaccaggctg gccttgaact cagaaatccg    12000
cctgcctctg cctcccgagt actgggatta aaggcatgca ccaccacgcc cgacgaaaat    12060
gtaccttatt agcactcttt tagggctaaa tgagaggtca tgcacaaaat gtgtatgtca    12120
gcttgatgca tagcagtcta tgcacaatgc atttcagtta tcattagaaa gaaaagtcat    12180
agaacatctg cttagaaaag agacctgctg ctgtgctgtt aggcatttcc aaatggctct    12240
gtgtgccgat acatccttag ggtgaatggt tagcgtctgg gttaacgctt ttaccccagg    12300
attgctcttg gtcagggata taaggattca gaagatgaga catttgcct tggcatattg    12360 ataacacatt ataaggaca aaggtgaaga aggaatatc ttaaaagcta gtgctggaca    12420
gggcaaaaag atgatgctaa ctaagcccta ctcaactata cttcacagtg atttcaatca    12480
gataccgctt ccacaaaagc ttgccagagg aaaggctgag ctgcctgatc agtgtgctgc    12540
atttgtctcc cccagatccg agacactaaa gggagaatgg caggtgcgga gaagatggcc    12600
gaatgtctta tcagatccga caaggaaaac tggccaaagg tcttgcaact tgctttggag    12660
aaagacaaca gcaagtttag tgaattgtgg attgttgata aggtggggt gctccaagaa    12720 agaaccctgg accctgctgc gctcctccca gttctcccca cttactttc catcagaggc    12780 gctgttcact tcagatacca aaggctatat ccctaggata caagcagtgg aaagctgaat    12840
tctgggagga agggaactac atggcatgga attaacccga ccaggtcaaa gaatctaggg    12900
aaggcttcca gccccaattt gttatcagag aaatagcttg agaattctag acctaaaggt    12960
tcaaactgca agacttacct ccctatcaga gcagaggctg agtgttgggg gtgatagcta    13020
tggactggtg ctcttgcccg gaagccatct ggactccgac agagcaagag taaacgaaga    13080
ttttctgtgt ttaagccaac ctcatttggc ttccggaaac tcacttcttg ctttaaacag    13140
accttgataa atacctgagt ttctagtttc cttctcacc tagatttcct tagaacataa    13200
attattccag aaactctcta catcgttggt cagagatgga atcctgtctc tttagtgtgc    13260
tcaggaatga cgcccctgcg ttattggcgt gagttccgga gtggggaggg gctccggatg    13320
caaactgctg agagccccgg gttccacact tggagtcgcg tagttccaga tgaaactgga    13380
attcaattgc caagttgagc ttcaaactca gaataatcct tgcagttgtt ttaagccgtc    13440
aaagtggggc tctctagatg gctcagtgga taaggttcct gccactgatc ctgaagaccc    13500
aaattcaacg tccagggcct acatgataga accaatcccc aaacagtgtc ctcatccctc    13560
ggcacactca ctgtgtcgtg tgtgacacac acagtaaaca aatccatttc aaaaataaat    13620
aaaatgttaa gaaagtgcaa gaccgtgatt gtaagagctc aacggaaatt tagatgttta    13680
gtgttagtgt taggactttt tgggacttcc ccaaccaaaa ccataatcac attgcgcatg    13740
cttttaatcc cagcactcag gaggcagagg caggtggatt tctgagttcg aggccagcct    13800
ggtctacaga gtgagttcca ggacagccag ggctatacag agaaaccctg cctcgaccac    13860
```

-continued

```
caccccctcc caaaaaaaaa aaaaaaagat tctaagctgt aagctgttat tgtgtttat    13920
gattgtttgc ttgcctgttt atcacaaagg tttcaaaagg gctgaaagca aggctgatga    13980
ggatgatgga gcggaggcgt ccagcatcca gattttcatt caggaagagc cagagtgtca    14040
gaatctcagt cagaatcccg ggcctccttc aggtaccaag catcgtttgc tctcatccat    14100
gatggtgtcc cccagcactt tgatgcccct tgaaaaaaag tcttttttaaa ggatgattaa    14160
gaaaagaaag aatttgtggg gcaataggga cttcataatt agaatccctg ctcctgtctt    14220
ccatggcctc tgcatggcct tcaaccctcc ccctcctctc ccctccctc ccctccctc    14280
cagtatgtat gccttcatct gtaccgtgtt cccagaactt cagtgtccat gacttctcaa    14340
agcagccttg ctctctaaag aacacttctg ctcactaagc aatggctttg agaatctggg    14400
ctgacagctg gttttcctcg gctgtttttg atgatctgtt cttactttgt tccaagtggc    14460
tttgttttga attaggccat tcttgctgtc cttttttcttg ataaagtttc cacgattaag    14520
aaagaattca tggggctgga gagatagatg gttcagcgtt taagagcacc gactgttctt    14580
tcagagatcc cgagttcaat tcctagcaac cacatagtga ctccagcgtc tgggttaatg    14640
ttttaccccc atctgtaatg ggctctggtg tactcttctg gtgtgtcaga ggacagcgac    14700
aatgtgtata ttcatataca ttaaataata aataaatctt caaagagaaa agaaggaagg    14760
aagaagtaac agagagagag agagagagag agagagagag agagagagag agagagagag    14820
agagaacaca ctttggccaa gatcccaaac ctcaaacagg ggcattgttg ctagagtcag    14880
aactcatgtc cactgaatgg cagttgcacc atgattcctt gtagcatgaa cccttcgata    14940
actttgtccc ctctatatta cagaagcgtc ttctaataat ttacacagcc cattgaaacc    15000
aagaaattac caactggagc ttgccctgcc tgccaagaaa gggaaaaata caataatatg    15060
tgcccctact ggtaagtcag ttgctgtcac tcacagaact ctctggcttc gcttttcttt    15120
ccccctttgg gggctgtaaa aggaggagtt ttccccgtgg cccatgctgc ccatgggaga    15180
gctggtctag cagcttaagg aacctggaca gcgataagga gggagataag tgtcttcttt    15240
agtttgcttt tggttcttgc tacctgagtg cacgttactt aggaagtagc ttggcacttt    15300
tcagccattg tttaaactgt cattgttagt gcggaggagg gattattagt ttatttgtat    15360
cccagtggtc atagagaagc caaataagt accattctgg aaaaacagct aacacaggtt    15420
atctgttggt ttttttttct tttctttttt tttcttttttt cttccctact aaaaggttgt    15480
ggaaaaacct ttgtgtcgct tcttatatgt gaacaccatc ttaaaaaatt cccatgtgga    15540
caaaaaggga aagtggtctt cttcgctaac caaattcctg tctatgagca gcaggcaact    15600
gtgttctcac gatattttga aagacttggg tatgtactac tacaatcaat ctaactgctt    15660
tgattttggg ttttttgttt gttttatgttt gtattttaaa ttctagcccc tttggctggt    15720
tttgggggct tgttgtgtc tggttttggg ggctttgttg tgtctggttt tgggggcttt    15780
gttgtgtctg gttttggggg ctttgttgtg tgttttctga cagtgtatat cacgtagcct    15840
tgagttgtct ccaacccact gtgtagctga ggttggccta agagagatga tcttcttgct    15900
tctacaagtg ctgagattac agtgtgcact ggcatgcctg gctgttctct gattttcttt    15960
cttttttttt tttttaagat ttatttattt attatatgta agtacactgt agctgtcttc    16020
agacactcca gaagagggca tcagatctca ttatgggtgg ttgtgagcca ccatgtggtt    16080
gctgggattt gaacttcgga ccttcggaag agcagtcagg tgctcttacc cactgagcca    16140
tctcaccagc cctctctgat tttcaaagct atgattaaag gaaaatcgcc atggacttaa    16200
```

```
cttttagagg tagttccttt gtgcaataac attttttggtt taactttacc agaaatgcta   16260
agccctcatg tcatgctctg acagttaatg aacttggtgg ccaaatttaa catgtaggcg   16320
atacacaggt catccttaat gatgttatac ttgattggct attactcttt tcaaaatcat   16380
ttctctctta atgacttgaa agaataaata cactgtgatc agctataacc tcttgcattt   16440
cctgactccc cggctttgtg tcaggcctgt gagaaagttc aaggtactac ccagttgtac   16500
tcttttgggc ttgggctgac ttctttaatt gctgctctga cctagacttc tactttgtct   16560
ccttgttcat tcacatcaag gttgatgata agggatttct gtcattcccc aggtacaaca   16620
ttgcgagcat ttctggggca acatctgata gcgtctcagt gcagcacatc attgaagaca   16680
atgatatcat catcctgaca ccccagattc ttgtgaacaa tctcaacaac ggagccatcc   16740
cctcgttgtc tgtcttcact ctgatgatat ttgatgagtg tcataacact agcaaaaacc   16800
acccatacaa tcagatcatg ttcagatacc tagaccacaa acttggagag tcacgggacc   16860
cactgcctca ggtatttcca atcttctaag aagaaccaca gttttcaga gtcccactta   16920 gttgctcttt tgtagccaca tttgagcttg ccctcctcgg ggtctcagtc catcggtaca   16980
actcagtggt caatgttggt tcattcattt gaccaacagt tgtcccttgg tgtccagggt   17040
agatgcccct cacaaaaaac aaaatctagg ctgcttaagt ctcttgtatg agatgacatt   17100
gcatttatat ataatctaca cactttcctc ttgcatactt taaatcttct ctagattact   17160
gatattgtac agtatgatga aaattttata taaatagttc tagtactgta atttttaggg   17220
aataaaggtg ggaaattcat acatgtttag tacttatgaa gttttaaaaa atattttga   17280 tccatggttg tatgaattca catttatata acctctggat ttggagggcc agctgtataa   17340
accatgggct tccatggacc ttgtgcattg ttctaggctc tgggacacca atacagaaga   17400
tatagtcctg gctctcatac agttaagttt gcagggagcc aggaacatag tagtcacagc   17460
ttatcatgag gtatgctgca gagacaggta aagggtgttg tcagaacata aggggtaata   17520
aggcatagaa atgaagggaa ctgacagggg cttgccaggt agatagcttc tggtttctag   17580
taagagggtg ctgtgtgtcc aggggctcag ggaaatggaa gggcctgaca tgccccagaa   17640
ccttaaaact ctacagtatc acttgagggt agagtgtgaa gcagggaaca acagtcaagc   17700
tgattgttat gacagatgac ccagagacac caggagggca gagcgtcagt gggcaagtgg   17760
atggcttagc acagggaaca agcagcagcc ttctgatgtc atatgagaag agtcacttca   17820
gagtcattct tacatgtgac aagaggagta caaattctcc ttctgtctat cataggagag   17880 gggggtgcttt gctgaaagtc aacgatatag aaacaggagg gggctagaga ggatgaggac   17940
ggtttgactc aggcactgat agatgcaata aagaatgacg gtagtgtatc tatcagggc   18000 cccaagaagc tgtaaaccat gaattatata caattctttt gctccaacaa taaccttttt   18060
aggacgtgca ggttaaagga catttagtac aggacccaca gtttgttatt ctcgagtatc   18120
gttgctagga agcagatttc ttaccgtcca gctaatcatt taggtgaatg cttactgaag   18180
ggtgttatca tactgaatct acacagctct cttgtacacg actcactgat tgttgaaggt   18240
atttgtccag gcgcacaaaa tgcatgtgat atgaatgagc ctggaatgga cttttttcttc   18300 ccattgtgat gtttagtaag agactggggg ataaaaaaaa cagggtagcc ctgcctggaa   18360
aggtttcctc tctgttctgg atgacacgct agatttattt ccgagctttg ctccagggg   18420 gtctttgtgc tggagaatgt cagagagcca gtggtggggt gctccttaca ggtcgttggg   18480
ctgactgcct ccgtcggcgt tggagatgct aagaccgcgg aggaagccat gcaacatatc   18540
tgtaaactct gtgccgccct ggatgcctcc gtgattgcca cagtcagaga caacgttgca   18600
```

-continued

```
gaactggaac aggtcgttta taagcccag aaaagtaagt ggaggtcagc agcccacacc    18660
tcgcgacttt gtaaccttct gtcccctctg cgtcagagac agtggatgaa gtttgatgct    18720
gtatttgttt ggtaaaagca tagtggttac attgcctatc tttctcccta gtcaacctct    18780
tctccctagc gacgcatgag tctcaaaggt agccagaaag gacaaacat ccctactctt    18840 taccagcagc tgagtgaagg aggcagtggg aagattcaag cattttgaaa gcctcaatag    18900
ctagtggcgg aatcaggtct ctgtgctccg ggccctaggc aggggctatg tggccatctt    18960
gttcttgtat gtatctgatc attgtagtgg catgacccga atcatgacag ttcaaaaggc    19020
cagaacatgt ttttaaaatg agcttcatta gaagatggtt attacttatt aactacctgt    19080
gtaagcaggg aggtaccgta gttacccacg gctggatctt ggcctgagca ctcgttctgt    19140
gagttgacag caggatcaat ggcagggtca atggcaggat gagcaatggg ggggtgggg    19200 ttgggatggc acaaccctgg ttcttctga gagtcccccg tggagagtgt gaagaaggtg    19260
cctccccacc cacgcccacc ccttagcaac actcaagggt ttttctacag tttgagccct    19320
tggagcttag tctacttcaa agtcattttg tgtcactttc tccgtctatg caaaccctct    19380
acgagctatt ctgagggtgt gtcccagctc ctgcgcgcct tccttttcc cttattattc    19440 atcttgcggc agcttccccg gagagaatga ggtttcctcc cctctttgag agatgccttc    19500
ctggcctgca cctgcttccc agggctctga tgggcgggtt taggagcaca cctttgtttc    19560
ctttaaggag tgggtgggtt ggggagcagg gggaggggg agggagggga taggggttt    19620 ttggagggaa aaccaggaaa gggaataaca tttgaaatgt aaataacgaa aatatcttta    19680
aagaaaagaa aagaaaagga aagaaagaaa gaacctgcct tctgtgcagc atagggtagc    19740
tcttgtcagc tctctgtcac tgaaacagga catgtgacag gcagttctttt ttctgccaaa    19800 agtacacaaa tgtgaacgat aagctcaatg ggggcactct tgggggctcg gaggtgcgca    19860
ggagaatagg aaatcaggaa aacggggctg gagtatggta tttgccgaaa ccagaaggct    19920
gccagacctg ccacagtaga ggcaccagga aagctgactg agacgctggc ttagactaga    19980
ccaggagaga cactagaatc agaagcagtt ccgaggtcag aggcttctga ccgcctgctg    20040
tgatttgggc cacgtgagct tggagcctgt ggctttaaag gacttaccca ggatggagca    20100
gcttcgggaa atggctgcat aggacctggg tttccttcag cttactcaca tgcctttgac    20160
cccagtttcc aggaaagtgg catcccggac ttcaacacg tttaaatgca tcatctctca    20220
gctgatgaag gagacagaga agctagccaa ggatgtctcc gaggaacttg gtaagcctgt    20280
gccaagtcct ggagagagaa atctcatgtt tcctgtccct tccatttaga ggtactcatg    20340
gattgctcgt tagtgtcttc agttttgggt gagattatac tcagaggtgg actgacttat    20400
ttattcacac atatttcttt ctgtctctgt atcttcttta tctcttcatt cttttttgcc    20460 atcattttt tctccattcc ttttttaaaa gatttattttt tatttgatat gtgtagatgt    20520
ttttgtctgc atgtatgtat gtatatcaca tgtatcagat acccgggaac tggagttaca    20580
gacagttgtg agctaccaca tctgctggga atcgaaccca tgtcctctag aagggtagct    20640
ggtgcgcata accactgagg agcccccatt tctctagctg tttttaagac aaggtttttt    20700
tccctgtgtc cctggttggc ctgaaacttg ctatgaagac aaggctggct ttgaacttgc    20760
aggggtcccc ttgcttcagc ttctgagtcc tggggtctct ggcaagcgcc accatacctg    20820
gctcagatat agactttctt aatcctaggt tgtttaggaa ccttatagga gttcttaat    20880 tctctcttgc cttttttcttt ttaaatacaa aacacatcca cctggacata catacctgag    20940
```

-continued

```
aaatactgtc tttaaatcat cttctaaatt tcctttcttc ctttttttcc cctcttgaga    21000
tagaatctct gtgttcagtg taggctggcc ttgaactggg aactctgccc ctcctcctcc    21060
tcctcctcct cccaagatgt gcatcatcac tgagctgcca ttagagtgcc attgtccctt    21120
ccaagagcag ttcccccagt gacctaacac tctctcactg tcctcagctc ttgaaagtgt    21180
caccacctcc taacctcaca cactgaggac caaccagcct tttgccacat gagcatccag    21240
aaggcactta gacagtagct aaggcacagc actgggggag gagtttgaat aatgaatcca    21300
ctatgggtcc taaagtagta gggtagcaag catgctctct cctctagagt tttggaaact    21360
ctctgtaagg taaagagtaa agagaccagg tagtcagtac atggctcacc taggaacaag    21420
ataacatggt ctgactaaag tggtggatgg acagacggac aggaatagag ttgtatgact    21480
tacttttttg ttttgttttt gttttttaaaa cagtctgtct gtatagctct gactgtcctg    21540
gaactctctt tgctggcctc aaactcacag agatctgcct gcctctgcct ccggaggcat    21600
tcacacttta gaatcttttc ccacctcctc acattgagta tctgtcaata gctgcctcac    21660
ttcttctgga acttggacgt ttttcattgt gaactgggtg tggtggcacc atctctactc    21720
ccagcagctg ggagcctgag tctgaggcca gcttaggcta catactgagc tcctgtcctt    21780
ggggcggagg ctgggaagaa cttgtcactg tttcttgttg gtacccgtcc tgtgttctgt    21840
tattgcaaat gtgagggaag ccatttaaca cacaaatgca tttcacttct ttgaactgta    21900
ctgtgcttgt ctcaagaagc ccaggacaca aaacaataga gcaagcatct ggggctgttc    21960
ccacttcgcc tttccccccc tacccacacc aatcttcccc tgagtctgaa tcgctgtgaa    22020
tcccacagta gaaccaagca gtcaagacat gcacatgcgc acacagatgc ttccgggata    22080
actgtgtttg actccgcctt gtggttggtg ctgcaagtgc tgctctgaga tcaggtgttt    22140
gggcttcata gcaacataga gcatgctggg aagggtcctg gtgctcccat ttttatataa    22200
ctgtctccga tgaagctctt gagacgtgct actctaatgg tatcttcatt ttgaaaggca    22260
aagtgtgtcc ctccttctct tcctcctcct ccttcttcct tacccctctt cttcgttctc    22320
tgttatttct gaactacttt ggctgtcagc cccttaagcc tgcagagcat agacaccaca    22380
gagctaggct tgaattcttg cctcacccac acaatatgag ctttatgaca ttgggggtaa    22440
attagttttc cttttataga agatttattt acttaaaaaa aaattatgtg catgtgcatg    22500
tgcgggatgg tgttgttgcc tccaggggtc agaagagggc gctgaatgcc ctggaactgg    22560
atttacaggt cgttggaagc cacccaatgt gagtgcaggg aactgaactt gggtcctcta    22620
caagggccta actattgagc caccacttct gctccttact caatcttct gaatctgttt    22680
cctcttttttt tttttaaag atttatttat ttattatatg taagtacact gtagctaagc    22740
tatcttcaga cactccagaa gagggagtcg gatcttgtta cggatggttg tgaaccacca    22800
tgtggttgct gggacttgaa ctcaggacct ttggaagaac agtcggtgtt cttatccact    22860
gagccatctc tccagcctgt ttcctcttta aaaaaaaaa ttaaataatg acctcatgaa    22920
attagaaaat ttcaatgcaa ttatgaagct tgattttggg tcatttagta aatagttatt    22980
ttacacactc ctcccccccca ccccccgcgc acgcacacag gcacacacac acacacacac    23040
acacacacac acacacacac acatagctta agacccagtc tacttcagga taaacatctt    23100
tcttataatg aataagaaag aaaatcagag gaccggtgct tgcaaatctt ttatttatct    23160
atttatgttc ttaccctgta ggaaagcttt tcaaattca aaacagagaa ttcggcaccc    23220
agaaatatga acagtggatt gtcggcgtcc acaaagcgtg ctcagtgttt cagatggcag    23280
acaaagagga ggagagccgg gtctgcaaag cgctcttcct gtacacatca catttgcggg    23340
```

```
tacattgctg ctctccaggg cttattctca tcaccgcgcc tcctgggatc tgtactgagg    23400
cagctgagag aacatcagcg tctcaagtct aagagcttag tgaggaactt ttcccgaaag    23460
tcatcactaa ccttatttgt tttctgaaac ttatcatcaa gtctccaaaa actggattaa    23520
aggctcagag tctatgccac acctccctcc agcttgtgac tggtgaccac catctaactg    23580
agctcaaaaa agtggctcct gtggccatat cctgaagctt tcgtggtctt aattttgtta    23640
taaagtcata tattagaatc tcaggggctc tggttaacac agagggaagg agtaactgta    23700
agagccctca gctctgtttg ctatgctctg gaactatttt aaagacttac tccacaccat    23760
gggattgtgg gatctaacgc ttaatggact ttcagcatag gtggtaaggg ccatcgttat    23820
gcaaggccca tgtacacttt aagtatgact tggaatttaa ggggaatgtc aaagctaact    23880
tgcttttgtt attgtttctc aagatatgct gtttctcctc tcccaaggtg gagttttata    23940
atccaaagtg aatctacttt taattttcta gctgagccaa aaatagaagc cagcttttgg    24000
ttcagaggtt tttattgtag acccactaag ggccattcgc cattaaaccc tcagctgtac    24060
tgtatgagaa agattttctg caaaccagtt ttgtgctaaa tacagcgagt tgaacttgag    24120
tgtagtgacc atatgcgacc tcagaaatgt attgagaatc acttttcatt tcaaacagaa    24180
atacaacgat gcactcatca tcagtgagga tgcacagatg acagacgctc taaattacct    24240
caaagccttc ttccacgatg tccgagaagc agcattcgat gagaccgagc gagagcttac    24300
tcggaggttt gaaggtgagg gagatttctg aagtcaggag tccctggggt ctggtggctt    24360
ttgtggcagt gtgcacatcg tagttagcat acgtagccat catgttgggt ttaaggtgag    24420
atttgtaggg gctgtgacgg agcatgacct tagcatggct gaaatcccca gcactaaaaa    24480
acgaacctat gctgaaactt tagagccaac caaccgacaa caggagggtt tggcttcaga    24540
gaaatctaat gcctgtggat ggatctgatg cttgccccac ttttcacttg ggaaaatggg    24600
aaacagtggg atttggaaag ggtgcttcct ctaggtggta ggtagtgcta ttctgattaa    24660
ctcagtaatt cagaaggttt aataacaaca gctcgtgtct gatggtgtca agattgtgct    24720
gtatgtatgt ccttccttcc ttccttcctt ccttccttcc ttccttcctt ccttccttcc    24780
ttccttcctt cctccctccc tccctccctc cctcccccct ttctcttctc ttctcttctc    24840
ttctcttctc ttctcttctc ttctcttctc ttctcttctc ttctcttctc ttctcttctc    24900
cttctcttct tcctcctcct tcatcttctt cttttcttcct cctcttcctt ctccttcttc    24960
ttcaaaacac agtctgtata gccccggctg tcctgaaact cactttgtac accaggctgg    25020
cctcgaactc agaaatctgc ctgcctctgc ctcctgagtg ctgggattaa aggcgtgtgc    25080
caccatgccc agtttgtgca catatatgtg catatgttta ttataaattt tactgataca    25140
ggagatggca tagcacaaaa cacacaaata ataaacacgg agttcatgtt ccacagaatg    25200
cctttggagg tcttttcagt acccttgtgt ccagagccaa ccagagacag caattcccca    25260
atatggagtt ctgaaatgaa agtcagtttt atttcctgtt aatggcagaa ataagaacaa    25320
aacgaaacag cagaagcatt ttggaagctt gcttgtttct cagtgatggg agcaacattt    25380
ttctgagcca gataatagtt tttcaaacac gggtgggaca tttctgcatt tttacgtgat    25440
gcataaacag tagctaaatt taatccccat tatatactta gcactttaca aagtctagcc    25500
agacaataaa ggatgaagca agtgctatct tcatttccat ggtatgggta cttctaggat    25560
caccaatctc caaccatcac catgttgctg aacttgtgta aaattgagca gtaacacaca    25620
ctgacatttc taccattcat acactacagg taagtacaca ctcaagagcg tagataatag    25680
```

```
taaactgtaa taaaatgagt taggaaatta ataagcgtgg ctatttgtta catttgtttt    25740
tagtcattga gctgcaagca taaagagttg aaattttaat aatagttata tttaaaacca    25800
ggtccacaag tctgaagaac ttaataactg accataatct ggtttgatct ggttctatct    25860
agtacaccac cagtgtgtgt gtgcgtgtgt gctcctatgc atacttatac attaaaaaaa    25920
aaaagatat cctatgcttc aattttaac ataaataac cttctgacag ctgggtggtg       25980
gtggtggtgc atgtctttaa ttgcagcact caggaggcag gggcaggtgg gtctctgggt    26040
tcaaggccag tctggtttac agagccagtt ctaggacagc cagggctaca cagagaaacc    26100
ttgtttcaag acaaaacgaa acaaaacaac cacaaataaa aaatatatct ttttgatgtt    26160
tccaaatcag caggtgtata taactctta actttaatag taacagtgta tttacctcag     26220
tttggtagcc tgggatccat tgagctgttt ctcactaagc agtgttttgg ttgttggttt    26280
tttttttttt tttttttttt ttttgtattt agttcatagt ttcaacactg attgtccttg    26340
gaatcttctt cagagttttt tttttttttt tttttaaag atttatttat ttattatttt     26400
atttaagtac actttagctg acttcagaca caccagaaga gggtgtcaga tctcattacg    26460
gatgttagtg agccaccatg tggttgctgg gatttgaact ctggaccttc ggaagaacag    26520
tcggtgctct taaccactga gccatctctc cagccccaga gttttctaaa tagaactatg    26580
agtcaattcc tatctgtgga ttgctgtatc aaagaacatg tgagttttgt attgctgcgc    26640
tgcttttcta aaggggattc ctgatgaaac gagtgtttac tgctctgatc tctggtgaac    26700
agtggaaagg ttaaccgaaa tagaaggcca ctgtttgttc taaagcttta acatttgtaa    26760
gccttttgca aaatgctctc tatttgcaga aaaactagag gaattagaaa aagtttccag    26820
ggatcccagc aatgagaatc ctaaactaag agacctctac ttggtcttac aagaagagta    26880
ccacttaaag ccagagacca agaccattct cttcgtgaag accagagcac tcgtggatgt    26940
aagtgtgtgt gtttacagat tagctctagt ttattgaaaa ggttgcccgt tcttcactgc    27000
cttataatca agtatccata catgtgtgga cctgttctga tgatttgttc ttacaccaat    27060
tgtcattgtt tgtattgacc cacagttata agtcttggtc ctatagagga agccctgcat    27120
ccttttaaa aatttaaaat ttccactttcc agtcatcctg taggttttga ttaatgacta   27180
atgtgtctta tatacctcac agttatcttc atatcatctt ttaaaaataa tttactcaga    27240
ttttaaaaac cagtttttaaa aattgggcaat gggctggaga tacagctcaa tggtcaaatg   27300
cttgttcagc atgcatgact ttaatcccca gttctggaaa aagatagata tctctctgtt    27360
tatgtagaat gccttgagtc tggccacagc gcctccctct gtttatgtag aatgcctgca    27420
ttgtttctgc tgagtagtag attacccata gagccagagg cagaaaaagt caagctttat    27480
tattttatga gatccgtgga tcaggatctg gaaaggactg gatacttatg cctcaaggtc    27540
tcctgaggcc acagtcagct cggcactcaa ggctgacctc tcggctcctt ttgcaggttg    27600
ttggcaggct tgtgaagatg agcctccaac atggcagctg cccctgccta cagtgagatg    27660
agagactgag gagaagaggg cctagtagac agacactgcc attttataaa gtccatcttg    27720
gacctgatgt cccaccacat ctcccatatt tcagagataa actacagatt atttttagaa    27780
tataggatgt agaagtcatt aagggtcgct tgtcatgtga tctttgctgt cttcttttgt    27840
taatgaatgt gggtgtttac catgtgcgtg tcgtgcccac agagtccagg aaggggcat     27900
gacatgccct ggaactggag ttaacagaca gttgtaagtt gccatgtagg tgctgggaat    27960
tgaactcagg tcctctggaa gaacaaccag tgctcttaac caccgagcca tctctccagc    28020
ccccttgct gtgttttatt agcatttgt cattttagt atagaggtcc tgcatacatt       28080
```

```
ttgttagatt catacctagg tattaatttt agtgttgtca ttccgaaatt gtactttcaa    28140
atatttctca ctgtgggcta ggaagacatc tcagtaaagt gtctaaagta caggcatcag    28200
gacctggctt ccagcaacct ggtaaaaaag ccgagtacag tagagtactc ttgtaatccc    28260
agccctgggg acagagataa gcacaaccct aactggcaat gcccaggtcc cagggagtta    28320
ctcattactc agtcttaggc agaacgaagg tgggtggctg ttaagaaatg atacctaggg    28380
ctggtgagat ggctcagtgg gtaagagcac ctgactgctc ttccgaaggt ccagagttca    28440
aatcccagca accacatggt ggctcacaac catccgtaac gagatctgac tccctcttct    28500
ggtgtgtctg aagacagcta cagtgtactt acatataata aataaataaa tctttaaaaa    28560
aaaaaaaaaa aaaaagaaa tgatacctga ggttgacctc cacatgcatg tacacacaca    28620
cacacacaca cacatgcgtg cgtggacata ctcccctcca acacagtcag ccatgtacac    28680
ctccacacaa cacacagttc ttccaattgc agctgtctgc tgatatttac tgtgtaatta    28740
atttacatgg attgatcttt caccttaaag ccttgctaaa tttcacttac tctatgtctg    28800
aagcttgtct ttttaatcac ttaaaatatc tcctacatta agccataatg aggcagagtt    28860
ctatatcact agcatcaatt gttgtttgga atttaggatt tgccagtctg aaatccattt    28920
ttatctttag ttgtattctc tttttgcata tacatccatt atatcaaatt gatgtgaggt    28980
ttaaagttta caagtggtgt ctaactggcc gttgcttttc acttttaggc tctgaagaaa    29040
tggattgaag aaaatcctgc actaagcttt ctaaagcctg gcatactgac tgggcgtggc    29100
agaacaaacc gggcaacagg tatttatgtc tattgaatta gatttagtat actatgtata    29160
taaaatgtat aaacactaca ttgttttagt gtttctatca gtcagagctc aaccagagaa    29220
ataaagctac tagattatgc atatgtatgt ggtatatatg taagtatgta tgcttatttg    29280
tttgtttgtt tatttatgta cttagagata gggtttctct gtgtaaccct tgctctcctg    29340
gaactcactc tgtggaccag gctggccttg aattcagaaa tccgcctgcc tctgcctccc    29400
gagtgctggg attaaaggtg tgcgccacca ctgcctggcc tatactgtta ttctttaccc    29460
agtagatttt ttttcccat ctactgcctc tttaatagtt ttaaaaaaac agtccaggca    29520
atcctgaact ctagctagtg tggtctaggg aggaaggtta tcatttccca taagaacccct   29580 atgtggctag ctctcatcac agctacgtcc caagtcatat ctcacgactg tatgacctgc    29640
cctcgctgtt cttcctgcca gtgttgttta cactaaacaa gtctccaccc cttctctctc    29700
cgtcctcagg cattgctctt gtacttttcc attgtggaat ttcccgatct cataaacata    29760
gaatggactc aagtgttgaa tgtgtggttt cgagtctaac actaccctaa tgtggctgga    29820
ttttcaaagt tctttgccat ctctccaaca tgaatccaac ttgattttca agctttgcta    29880
ctgacatata aatcgagcct tgaataatat tttgtgtgct catccatgca tgcatggatc    29940
catggatcca atcatgtgtc caaccactca tccacccatc cgtgcatgca tccatctttc    30000
cgtcatgcat ttagacctta ctcagctcct gcttctgtga agaagcagcc atccctgtca    30060
tctaacaccc gaggtgcccc tcccccgcc acgttcccat cttacagatc tcaccccact    30120
tcctccacaa tggcttcctg ctcatcatcc ttatagataa agatggaatc tttaagcgtc    30180
atatttctac ctgctcagcc ataacccata attgctgacc gagtgttgga tggatgaatg    30240
aattggttag gatgattctg ctattgttgt tttctggatg attctttctt gttttatagc    30300
taacctggga aaaaggtgg acttttacaa aaagccacag gttgcttggt gtttggacat    30360
tttcagattc ccttatctgt agcatttta cttcctactt tgagacacat gttgtaatgt    30420
```

```
ttatgcctta ctatcttcat ctgtcaaatg gaacaataaa tagttgtccc cagctcatag    30480
gttaacgaga atggtgaaac ctgagctttt tttttttttt tttttttttt tgtgaaaatg    30540
actttggcac ttttagatgg ttcaaaatta gtagccagtt tatgagtgag ttgtacagtg    30600
acctctttat ccaacacagg aatgacgctc ccggcacaga agtgtgtgct ggaggcattc    30660
agagccagcg gagataacaa tattctgatt gctacctcgg tcgctgatga aggcattgac    30720
attgctgagt gcaatctcgt cattctctat gagtacgtgg gcaacgtcat caagatgatc    30780
caaaccagag gtgagagcgg ctgatgtcat tcccgccccg cacccgcttt tctcctttcc    30840
tcagctgtac catgtgattg acagcacagc tgactctggt actcgaaatc taaaagctga    30900
ctgccttggt caggattggg tggttatagg tttacccata atactccatt gcaactctcc    30960
acaatggtac tgcaatttta cccagcgttc aatggcatag tcgtgaaaat atcatatcca    31020
ctaggccaga ggctttgcca gtcggcaagt agacctttga tgggtgtggt gagtagctct    31080
ctgtactcca gagtctggtc ccacctgaac cagagtctga cttcctttcc ctttcttgtt    31140
tccccaagaa cagcccccac attccctttc cggaataacg tctctgtgcc tgtcactcat    31200
cagtcacatc cattttttcgt cctcctccac cgcttactgt gcggttcagc cagccagact    31260
ccgcttcctg ctcgtccagt ttctcagata ctgtcgctct acatgttagg tcctatctct    31320
gtctctgcca cacacaacct aattcttcta cctagaacaa gcactccttt aaatgcccac    31380
taccgtttat atctgtctct gcaagagcat gacaattgca ttcctttctc cgcattgcag    31440
aagggtcagg tgcgcgtgca cggtgccact gctgcgggct catgccagat tatctgtaaa    31500
ttagtgttgc tggcagtgca gagcaatcag actatgccat ggagacccc atgaaaactg    31560 ccagagatgg cttatctgtg tgctgagcac actggctaga acctgcattt gagtctactc    31620
ttcggttcag cttccctaga aagtaggatg cagtgaatca aagttgaact cgagaaatac    31680
tcctcacatc tctttccagt aacctcagag tttgacatta acacacaaag aaaacgtttt    31740
ctgcaggccg aggaagagca cgagatagca agtgcttcct cctgaccagc agcgctgacg    31800
tgattgaaaa agaaaaggcg aacatgatca aggaaaaaat aatgaatgaa tccatcttaa    31860
gactgcagac atgggatgaa atgaaatttg gaaagacggt aagtctcttt ttctgtgcta    31920
ctcttatgga atctgactag aaataacaaa tgaccatggt tggtcctgag tgtgtgtgtg    31980
tgtgtgtgtg tggtatgtgt ttgtggccat gtgcatttat ttatctttgt gtgctagttt    32040
tggccattca aataaccttt ctgttcgcat gtaggttcac cgcatacagg tgaatgaaaa    32100
actcctcaga gacagtcagc acaaaccaca acctgttcct gacaaagaaa acaagaaact    32160
gctgtgtgga aagtgcaaga attttgcgtg ctacacagct gacattcgag tggttgaggt    32220
gagtggccct ggtgatttag caccggttaa atcttaccat cttccggaga aatggttgta    32280
gcaagaacac tatgttgtgg ggtttcgagt gttgaccatg gtcctgtatt aagaaataaa    32340
atcctgctag gtggtggtgg cacacgcctt taatcccagt acttgggagg cagaggcagg    32400
cggatttctg agttcgaggc cagcctggtc tacagggtga gttccaggac agccagggct    32460
acacagagaa accctgtctt ggaaaaacca aaaaaaaaaa aaaaaaaag aaataaaatc    32520 ctgcttctat gtgggaacca gaaaggctga tgttatttaa gtccaaaaca gaaaatggtg    32580
cttaacggcg agaagaggag gggggtctaa ttgtagctgc cccagacagt caggcaggat    32640
ggataaggtt tcccgttcca ctgcacagca gggtgaatac tgcttatagt ttctgattca    32700
ttacaactct tacaaagaat tagacgagag gaattcatag cttcagacat aaagagatga    32760
aaactgtcca ggcagaaggg aatgctaatt actctggcga gatcattaga tacttagaaa    32820
```

```
ttatcacact gcacacccta agtgaggaca actgtgtgct ttgaaagaca gtctcactca   32880
gaccaggctg gcttcaactt gagattcttc tgtgactcag cctccccagt gcagggactc   32940
taggcatgca ccaccactct ctccaaagag atagtttttc ccagtgcagg gatagaaaat   33000
gaaggctctg ctagatacag tgttatgtcc ttggttagtt ccagggagga ggaagggcta   33060
ggcataaaaa tctgtcattg atttcttagt tttaacaaat gtgcaactgc attcaaaatg   33120
gaactgggct aaaggcattt gcaaatcttc tgaggcatct ctgtaacttt actgtatgtc   33180
aaagattatg ccaaagaaat gttaaggctc tgattttgaa gtgtacatgg ttctagtata   33240
aacctgccag caaatgaatg gtaaagtggg aaaatactat gaatatgaaa ttataaagat   33300
gcttttgtta tggctacata caacatgagc agtgatatct ttgtcatgac caatgtgggt   33360
ccacctttcc taaagggaa aaaaggctaa tatataaaaa tgacatattc tgctagtgaa   33420
ttctctcttc ctgttttgtt ttctaaactt ccttattgga acagagaatg cttttataat   33480
gaaaacaaaa cacctcattt taaaaatat aacacttgta ggttagcttt ctactttttc    33540
accccttaaa cttttttttt tttttttga dacaggatct ctctctatag cactgggtat   33600
cttgaaactc attatatgga gattcccttg tccctgcctc ccaaacgctg ggacgtaaag   33660
gcatgtacca ttacacaagg tcttcttaaa acttttaact aaggcaaaaa acctccagag   33720
acgaatcttg cagtcatcat tcctgctacc gatggcgggg gcagatggct gtgctagcta   33780
ggggaggggt acagtcctta ttatgagtga catccacttt ctgagtctga ttctttagat   33840
gcagaaggtc ctttcagctc caaattcaag gcttctcctt cccagtggcc tggagaacga   33900
gatgcttggt ctgcgcttgc gtctgtaggg tacactcttt tttttttaat tggatatttt   33960
ctttatttac ataaagaaca ccttcagttc ccctacactg gggcatctaa gccttcatag   34020
gaccaaggac ctctcttccc attgatgcat gacaaggcca tcctctgcaa cgcacgcagc   34080
tggagccatg tgtactcctt tgtggatggc ttagtcgctg ggagctcttg ggggactggt   34140
tggttgatat tgtttttctc cctgtggggt tccttcagtt gtagggtact ctcttaagtc   34200
aagtctaagt ggggtctgtg gacagcatgg ctcctgagcc tgttcacaca cataccctgt   34260
gacccctggg tgtcaccagc cctgtgcttt ggtgccttcc tggcctctgg tgaacttgaa   34320
ctttgtatgt gaactcctct ttgcttctga gttggaaagc tgggtttcct cctttctcag   34380
gtgccagacg cccaggaaat gggtcctaat cggcctgggg aagactgtct atatagtttt   34440
tttttcttcc aacttgtaaa ataaatggga tcccactcat tcctgacttt tagctactga   34500
gtggcttcta agtcattttc agacccgttt ctaacattgt gcgctccatc tcttcctcct   34560
agacgtccca ctacactgtc cttggagacg cttttaagga gcgctttgtg tgtaagccac   34620
accctaaacc aaagatctat gacaattttg agaagaaagc aaagatattc tgcgccaaac   34680
agaactgtag ccacgactgg ggaattttg tgagatacaa gacgttcgag attccagtca    34740
taaaaattga agtttcgtc gtggaagata ttgtgagcgg agttcagaac cggcactcaa     34800
agtggaagga ctttcatttt gaaaggatac agttcgatcc tgcagaaatg tccgtatgac   34860
ctcaggcttc tccgtctcgt gccgcaggga gccgtgcctt aagcatggag ttgatgagcc   34920
aatgctttct tacccaagct tgcacaatcc tttcttacac aagcctgcac tgtgttgaat   34980
gccagataac ctgactggtt ggtttcaagc tggtgctgtc cacacaaagc acacacgcct   35040
gaactgcggc gccgaatagt ttcttcacca ataactcata gcgtagccct tggccatggt   35100
ggggaggggt taaacttgtc ccttttacac ttttcagaac tgcccgacag ggaacgtgca   35160
```

```
gccactcggt acaccgagac gcatgatggc tggcgtgctg gaagggttcc cgttctctgt   35220
ctgctcgatc tgctgtaagc tgcctttgcc cttaatgaca gtgcccttaa gaacagtgac   35280
ttagttcttt ttcaggccac cagactgact gccagatccc ttctgtccct tctgtccctt   35340
gcactgattc cttccggat ttgaccctgc caccctgtca ccctctgcag agtctcctgg   35400
tttctgtctc ttccttggtt tctttgctga ctcaaatttg gtagttgcaa ggttcagtat   35460
gcacacatat atatttaaaa tgacatataa tttaaaatgt aaaagactat agttgacagc   35520
tatgcttact gagatggtat ttctgttctg ttcattacta tacatcttac ccttgctctc   35580
atctgttctt ttaacttggg ccatttcccg tctttgaata gacatctcaa accctgtctg   35640
tatgtctgtc tgtttcccac ctgtttgaga cagggtctct ctgtagacca gaaactccat   35700
atgtagacta tgctggcctt gaactcacag atccccctgc ctctcaagtg ttgaaattaa   35760
aatctttcac catgcctggc tctagctatt ttcaataaag gctcatgttt aaagtttgaa   35820
ctacttccaa ttcattccct gacgtggctt gttgttgttg tttacttttg gagacactgt   35880
tcctctctgt agccctggct gtgtagacca ggctgccctt ggtcacagag atctgccagc   35940
ttctgcctcc ggagcactga gattgaaggc ctgcatcacc atgcctggct gccctttct   36000
tcttaaacat tatatattca aatggcattt ccgtgtttct tctcaaggtg tgccagtgct   36060
tcagagagct tagtttgggg ttcttcagat caagagacaa gtgtctgagc gctgttactg   36120
ccaacagagc aaagtactct tcagttcagg gaaggaacag tgctggtttt gtaggcagta   36180
cagtggtttt aacaccttcc tagaacttac ttgtaattca tcagttgtag accatcaatg   36240
gcctaaacca aactgcagag atcatctgac cacataactc cccttccagg acatttacat   36300
ttgaagacta tcccaagccc acccagagca cagtgggtta cccaaactcc ccaggtcaac   36360
cctggaggtc aacagtatga catgggatag cacaccactt ctcacagatg cctagagaaa   36420
ttacccagca acataactct ttggggaaaa aacacctata gggattaggc ttttaattga   36480
tagaataggt agaaaaaaag atatgtagta gttcttgata gtggttactg gtaaaattct   36540
tagtgcaata aaatgaattt gccgagagct gactttcttt ttttttcttgt ttttttgaga   36600
cagggtttct ctgtatagct ttggctgtcc tggaatgcac tctgtagtcc aggctggcct   36660
tcgaactcag aaatccgcct tcctctgcct cccaagtgtt gggattaaag gcgtgcgcca   36720
ccacgcctgg ctgagagctg actttcattt atgtcttta gtctatgttg cctttctttg   36780
ctgctacagt ttaagaactc tacagcttgt ataagatacc tactggaaat tatttgagaa   36840
aaaaaacttg taaacattac aataatttaa ttaattaaaa atttatgtat tttatgtata   36900
tgggtgtttt tttctgcaag tctgtgtgca cattagaaga gggcattgga tcctctctat   36960
tgttatagtt ttatgctgct gctgttgttg ctgtgtgtgt gtgtgtgt gtgtgctatg   37020
aattgaactc aggacctctg gaagagcagt cagtgctctt aactgctgag ctatctctcc   37080
agtcctggca atgataaatc agttgaagtg aaatagtcct ccccccctt tttttttttt   37140
gccaatgggg aaaagcagac taaatctgag accaaatgaa gttttgagtt gtacactgac   37200
ttaagccact gccaagcata ccctggaatg gagcaaaccc tgggttacta agtactgaat   37260
gaatacaaca ggaaggtttt gagagatggg aaaatgcttg tctttggact tccctgatgg   37320
aagttgcatc tggactctcc catgagcaca tcaccagtcc ccactagagt cctcacaggt   37380
tgccatccat gtgtcctttt tgaggctgag atacaacttg ttctgcaacc acagaccttg   37440
ctgttttgtg gtcagtattg gtatcatagc attttcatcc tgacctggag ccttcagtca   37500
aaggcctcat tgtgcagtaa ggacgctgga ctcctgactc ctatacttaa aacagacttg   37560
```

```
gtaatttcaa acaagtcaac cagatgccag tatttctgca tgcatgtctt gtgggatggt    37620
gttgtgaggt cccctgacag atgcactgag tggccaggga gacttttgta cccttttcca    37680
ttttaacagc ccacgggtca ctgtgttgct tccatcatat taacatcaac ttgaaccagt    37740
ggttcctgaa acacttcagt tcattggacc ttgctaatta gcatcctgta aaacccacc     37800 aacaaatatc aactagacag gtagaatcca agtgaactgt acactcctgg atcatgccag    37860
taactgtttt aataatacac cataaaatat aactacgact tcattttaca aatctgtgtt    37920
taataaacag gtacaggctt gttgggtgcg aacttttaaa actcctaata aaaatgccag    37980
ctatgattat ctttgtttat g                                              38001
```

<210> SEQ ID NO 12
<211> LENGTH: 3435
<212> TYPE: DNA
<213> ORGANISM: Rattus norvegicus
<220> FEATURE:
<221> NAME/KEY: CDS
<222> LOCATION: (370)..(1815)

<400> SEQUENCE: 12

```
cgtttgtagt gtcagccatc ccaattgcct gttccttctc tgtgggagtg gtgtctagac     60
agtccaggca gggtatgcta ggcaggtgcg ttttggttgc ctcagatcgc aacttgactc    120
cataacggtg accaaagaca aagaaggaa accagattaa aaagaaccgg acacagaccc     180
ctgcagaatc tggagcggcc gtggttgggg gcggggctac gacggggcgg actcgggggc    240
gtgggagggc ggggccgggg cggggcccgg agccggctgc ggttgcggtc cctgcgccgg    300
cggtgaaggc gcagcggcgg cgagtggcta ttgcaagcgt ttggataatg tgagacctgg    360 gatgcaggg  atg tcg act atc tgc ccc cca cca tct cct gct gtt gcc aag    411
           Met Ser Thr Ile Cys Pro Pro Pro Ser Pro Ala Val Ala Lys
             1               5                  10 aca gag att gct tta agt ggt gaa tca ccc ttg ttg gcg gct acc ttt       459
Thr Glu Ile Ala Leu Ser Gly Glu Ser Pro Leu Leu Ala Ala Thr Phe
 15              20                  25                  30 gct tac tgg gat aat att ctt ggt cct aga gta agg cac att tgg gct       507
Ala Tyr Trp Asp Asn Ile Leu Gly Pro Arg Val Arg His Ile Trp Ala
                 35                  40                  45 cca aag aca gac caa gta ctc ctc agt gat gga gaa atc act ttt ctt       555
Pro Lys Thr Asp Gln Val Leu Leu Ser Asp Gly Glu Ile Thr Phe Leu
             50                  55                  60 gcc aac cac act ctg aat gga gaa att ctt cgg aat gcg gag agt ggg       603
Ala Asn His Thr Leu Asn Gly Glu Ile Leu Arg Asn Ala Glu Ser Gly
         65                  70                  75 gca ata gat gta aag ttt ttt gtc tta tct gaa aag ggc gtc att att       651
Ala Ile Asp Val Lys Phe Phe Val Leu Ser Glu Lys Gly Val Ile Ile
     80                  85                  90 gtt tca tta atc ttc gac ggg aac tgg aac gga gat cgg agc act tac       699
Val Ser Leu Ile Phe Asp Gly Asn Trp Asn Gly Asp Arg Ser Thr Tyr
 95                 100                 105                 110 gga cta tca att ata ctg ccg cag acg gag ctg agt ttc tac ctc cca       747
Gly Leu Ser Ile Ile Leu Pro Gln Thr Glu Leu Ser Phe Tyr Leu Pro
                115                 120                 125 ctg cac aga gtg tgt gtt gac agg cta acg cac atc att cga aaa gga       795
Leu His Arg Val Cys Val Asp Arg Leu Thr His Ile Ile Arg Lys Gly
            130                 135                 140 agg ata tgg atg cac aag gaa aga caa gaa aat gtc cag aaa att gtc       843
Arg Ile Trp Met His Lys Glu Arg Gln Glu Asn Val Gln Lys Ile Val
        145                 150                 155
```

```
ttg gaa ggc acc gag agg atg gaa gat cag ggt cag agt atc atc cct       891
Leu Glu Gly Thr Glu Arg Met Glu Asp Gln Gly Gln Ser Ile Ile Pro
    160                 165                 170 atg ctt act ggg gag gtc atc cct gtg atg gag ctt gcg tct atg           939
Met Leu Thr Gly Glu Val Ile Pro Val Met Glu Leu Leu Ala Ser Met
175                 180                 185                 190 aga tca cac agt gtt cct gaa gac ctc gat ata gct gat aca gta ctc       987
Arg Ser His Ser Val Pro Glu Asp Leu Asp Ile Ala Asp Thr Val Leu
                195                 200                 205 aat gat gat gac att ggt gac agc tgt cat gaa ggc ttt ctt ctc aat       1035
Asn Asp Asp Asp Ile Gly Asp Ser Cys His Glu Gly Phe Leu Leu Asn
                210                 215                 220 gcc atc agc tca cat ctg cag acc tgc ggc tgt tct gtg gtg gta ggc       1083
Ala Ile Ser Ser His Leu Gln Thr Cys Gly Cys Ser Val Val Val Gly
            225                 230                 235 agc agt gca gag aaa gta aat aag ata gta aga aca ctg tgc ctt ttt       1131
Ser Ser Ala Glu Lys Val Asn Lys Ile Val Arg Thr Leu Cys Leu Phe
        240                 245                 250 ctg aca cca gca gag agg aag tgc tcc agg ctg tgt gaa gcc gaa tcg       1179
Leu Thr Pro Ala Glu Arg Lys Cys Ser Arg Leu Cys Glu Ala Glu Ser
255                 260                 265                 270 tcc ttt aaa tac gaa tct gga ctc ttt gta caa ggc ttg cta aag gat       1227
Ser Phe Lys Tyr Glu Ser Gly Leu Phe Val Gln Gly Leu Leu Lys Asp
                275                 280                 285 gcg act ggc agt ttt gta cta cct ttc cgg caa gtt atg tat gcc cct       1275
Ala Thr Gly Ser Phe Val Leu Pro Phe Arg Gln Val Met Tyr Ala Pro
                290                 295                 300 tat ccc acc aca cac atc gat gtg gat gtc aac act gtc aag cag atg       1323
Tyr Pro Thr Thr His Ile Asp Val Asp Val Asn Thr Val Lys Gln Met
                305                 310                 315 cca ccg tgt cat gaa cat att tat aat caa cgc aga tac atg agg tca       1371
Pro Pro Cys His Glu His Ile Tyr Asn Gln Arg Arg Tyr Met Arg Ser
            320                 325                 330 gag ctg aca gcc ttc tgg agg gca act tca gaa gag gac atg gct cag       1419
Glu Leu Thr Ala Phe Trp Arg Ala Thr Ser Glu Glu Asp Met Ala Gln
335                 340                 345                 350 gac acc atc atc tac aca gat gag agc ttc act cct gat ttg aat att       1467
Asp Thr Ile Ile Tyr Thr Asp Glu Ser Phe Thr Pro Asp Leu Asn Ile
                355                 360                 365 ttc caa gat gtc tta cac aga gac act cta gtg aaa gcc ttt ctg gat       1515
Phe Gln Asp Val Leu His Arg Asp Thr Leu Val Lys Ala Phe Leu Asp
                370                 375                 380 cag gtc ttc cat ttg aag cct ggc ctg tct ctc agg agt act ttc ctt       1563
Gln Val Phe His Leu Lys Pro Gly Leu Ser Leu Arg Ser Thr Phe Leu
            385                 390                 395 gca cag ttc ctc ctc att ctt cac aga aaa gcc ttg aca cta atc aag       1611
Ala Gln Phe Leu Leu Ile Leu His Arg Lys Ala Leu Thr Leu Ile Lys
        400                 405                 410 tac ata gag gat gac acg cag aag ggg aaa aag ccc ttt aag tct ctt       1659
Tyr Ile Glu Asp Asp Thr Gln Lys Gly Lys Lys Pro Phe Lys Ser Leu
415                 420                 425                 430 cgg aac ctg aag ata gat ctt gat tta aca gca gag ggc gac ctt aac       1707
Arg Asn Leu Lys Ile Asp Leu Asp Leu Thr Ala Glu Gly Asp Leu Asn
                435                 440                 445 ata ata atg gct cta gct gag aaa att aag cca ggc cta cac tct ttc       1755
Ile Ile Met Ala Leu Ala Glu Lys Ile Lys Pro Gly Leu His Ser Phe
            450                 455                 460 atc ttc ggg aga cct ttc tac act agt gtc caa gaa cgt gat gtt cta       1803
Ile Phe Gly Arg Pro Phe Tyr Thr Ser Val Gln Glu Arg Asp Val Leu
```

```
              465                 470                 475
atg act ttt taa acatgtggtt tgctccgtgt gtctcatgac agtcacactt           1855
Met Thr Phe
    480 gctgttacag tgtctcagcg ctttggacac atccttcctc cagggtcctg ccgcaggaca    1915 cgttacacta cacttgtcag tagaggtctg taccagatgt caggtacatc gttgtagtga    1975 atgtctcttt tcctagacta gatgtaccct cgtagggact tatgtttaca accctcctaa    2035 gtactagtgc tgtcttgtaa ggatacgaat gaagggatgt aaacttcacc acaactgctg    2095 gttggttttg ttgttttttgt tttttgaaac ttataattca tggtttacat gcatcacact   2155 gaaaccctag ttagcttttt acaggtaagc tgtgagttga ctgcctgtcc ctgtgttctc    2215 tggcctgtac gatctgtggc gtgtaggatc acttttgcaa caactaaaaa ctaaagcact    2275 ttgtttgcag ttctacagaa agcaacttag tctgtctgca gattcgtttt tgaaagaaga    2335 catgagaaag cggagtttta ggtgaagtca gttgttggat cttcctttat agacttagtc    2395 ctttagatgt ggtctgtata gacatgccca accatcatgc atgggcactg aatatcgtga    2455 actgtggtat gcttttttgtt ggtttattgt acttctgtca agaaagtgg cattggtttt    2515 tataattgtt gccaagtttt aaggttaatt ttcattattt ttgagccaaa ttaaaatgtg    2575 cacctcctgt gcctttccca atcttggaaa atataatttc ttggcagaag gtcagatttc    2635 agggcccagt cactttcgtc tgacttccct ttgcacagtc cgccatgggc ctggcttaga    2695 agttcttgta aactatgcca gagagtacat tcgctgataa aatcttcttt gcagagcagg    2755 agagcttctt gcctctttcc tttcatttct gcctggactt tggtgttctc cacgttccct    2815 gcatcctaag gacagcagga gaactctgac cccagtgcta tttctctagg tgctattgtg    2875 gcaaactcaa gcggtccgtc tctgtccctg taacgttcgt accttgctgg ctgtgaagta    2935 ctgactggta aagctccgtg ctacagcagt gtagggtata cacaaacaca gtaagtgtt    2995 ttatttaaaa ctgtggactt agcataaaaa gggagactat atttattttt tacaaaaggg    3055 ataaaaatgg aacccttttcc tcacccacca gatttagtca gaaaaaaaca ttctattctg    3115 aaaggtcaca gtggttttga catgacacat cagaacaacg cacactgtcc atgatggctt    3175 atgaactcca agtcactcca tcatggtaaa tgggtagatc cctccttcta gtgtgccaca    3235 ccattgcttc ccacagtaga atcttattta agtgctaagt gttgtctctg ctggtttact    3295 ctgttgtttt agagaatgta agttgtatag tgaataagtt attgaagcat gtgtaaacac    3355 tgttatacat cttttctcct agatggggaa tttggaataa aatacctttta aaattcaaaa    3415 aaaaaaaaaa aaaaaaaaa                                                 3435

<210> SEQ ID NO 13

<400> SEQUENCE: 13

000

<210> SEQ ID NO 14

<400> SEQUENCE: 14

000

<210> SEQ ID NO 15
<211> LENGTH: 22
<212> TYPE: DNA
<213> ORGANISM: Artificial sequence
```

```
<220> FEATURE:
<223> OTHER INFORMATION: Synthetic oligonucleotide

<400> SEQUENCE: 15
tgtgacagtt ggaatgcagt ga                                              22

<210> SEQ ID NO 16
<211> LENGTH: 25
<212> TYPE: DNA
<213> ORGANISM: Artificial sequence
<220> FEATURE:
<223> OTHER INFORMATION: Synthetic oligonucleotide

<400> SEQUENCE: 16
gccacttaaa gcaatctctg tcttg                                           25

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 17
tcgactcttt gcccaccgcc a                                               21

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
gggtctagca agagcaggtg                                                 20

<210> SEQ ID NO 19
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 19
gtcttggcaa cagctggaga t                                               21

<210> SEQ ID NO 20
<211> LENGTH: 24
<212> TYPE: DNA
<213> ORGANISM: Artificial sequence
<220> FEATURE:
<223> OTHER INFORMATION: Synthetic oligonucleotide

<400> SEQUENCE: 20
tgatgtcgac tctttgccca ccgc                                            24

<210> SEQ ID NO 21
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 21
tcctgtaatg gaactgcttt ca                                              22
```

```
<210> SEQ ID NO 22
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 22
ggtatctgct tcatccagct tt                                                22

<210> SEQ ID NO 23
<211> LENGTH: 16
<212> TYPE: DNA
<213> ORGANISM: Artificial sequence
<220> FEATURE:
<223> OTHER INFORMATION: Synthetic oligonucleotide

<400> SEQUENCE: 23
ccccggcccc ggcccc                                                       16
```

METHODS FOR MODULATING C9ORF72 EXPRESSION

SEQUENCE LISTING

The present application is being filed along with a Sequence Listing in electronic format. The Sequence Listing is provided as a file entitled BIOL0214USASEQ_ST25.txt created Apr. 15, 2015, which is 132 Kb in size. The information in the electronic format of the sequence listing is incorporated herein by reference in its entirety.

FIELD

Provided are methods for reducing expression of C9ORF72 mRNA and protein in an animal. Such methods are useful to treat, prevent, or ameliorate neurodegenerative diseases, including amyotrophic lateral sclerosis (ALS), frontotemporal dementia (FTD), corticalbasal degeneration syndrome (CBD), atypical Parkinsonian syndrome, and olivopontocerellar degeneration (OPCD).

BACKGROUND

Amyotrophic lateral sclerosis (ALS) is a fatal neurodegenerative disease characterized clinically by progressive paralysis leading to death from respiratory failure, typically within two to three years of symptom onset (Rowland and Shneider, N. Engl. J. Med., 2001, 344, 1688-1700). ALS is the third most common neurodegenerative disease in the Western world (Hirtz et al., Neurology, 2007, 68, 326-337), and there are currently no effective therapies. Approximately 10% of cases are familial in nature, whereas the bulk of patients diagnosed with the disease are classified as sporadic as they appear to occur randomly throughout the population (Chio et al., Neurology, 2008, 70, 533-537). There is growing recognition, based on clinical, genetic, and epidemiological data, that ALS and frontotemporal dementia (FTD) represent an overlapping continuum of disease, characterized pathologically by the presence of TDP-43 positive inclusions throughout the central nervous system (Lillo and Hodges, J. Clin. Neurosci., 2009, 16, 1131-1135; Neumann et al., Science, 2006, 314, 130-133).

To date, a number of genes have been discovered as causative for classical familial ALS, for example, SOD1, TARDBP, FUS, OPTN, and VCP (Johnson et al., Neuron, 2010, 68, 857-864; Kwiatkowski et al., Science, 2009, 323, 1205-1208; Maruyama et al., Nature, 2010, 465, 223-226; Rosen et al., Nature, 1993, 362, 59-62; Sreedharan et al., Science, 2008, 319, 1668-1672; Vance et al., Brain, 2009, 129, 868-876). Recently, linkage analysis of kindreds involving multiple cases of ALS, FTD, and ALS-FTD had suggested that there was an important locus for the disease on the short arm of chromosome 9 (Boxer et al., J. Neurol. Neurosurg. Psychiatry, 2011, 82, 196-203; Morita et al., Neurology, 2006, 66, 839-844; Pearson et al. J. Nerol., 2011, 258, 647-655; Vance et al., Brain, 2006, 129, 868-876). The chromosome 9p21ALS-FTD locus in the last major autosomal-dominant gene whose mutation is causative of ALS. The ALS-FTD causing mutation is a large hexanucleotide (GGGGCC) repeat expansion in the first intron of the C9ORF72 gene (Renton et al., Neuron, 2011, 72, 257-268; DeJesus-Hernandez et al., Neuron, 2011, 72, 245-256). A founder haplotype, covering the C9ORF72 gene, is present in the majority of cases linked to this region (Renton et al., Neuron, 2011, 72, 257-268). This locus on chromosome 9p21 accounts for nearly half of familial ALS and nearly one-quarter of all ALS cases in a cohort of 405 Finnish patients (Laaksovirta et al, Lancet Neurol., 2010, 9, 978-985).

A founder haplotype, covering the C9ORF72 gene, is present in the majority of cases linked to this region.

There are currently no effective therapies to treat such neurodegenerative diseases. Therefore, it is an object to provide compositions and methods for the treatment of such neurodegenerative diseases.

SUMMARY

Provided herein are methods for modulating levels of C9ORF72 mRNA and protein in cells, tissues, and animals. In certain embodiments, C9ORF72 specific inhibitors modulate expression of C9ORF72 mRNA and protein. In certain embodiments, C9ORF72 specific inhibitors are nucleic acids, proteins, or small molecules.

In certain embodiments, modulation can occur in a cell or tissue. In certain embodiments, the cell or tissue is in an animal. In certain embodiments, the animal is a human. In certain embodiments, C9ORF72 mRNA levels are reduced. In certain embodiments, C9ORF72 protein levels are reduced. In certain embodiments, certain C9ORF72 mRNA variants are preferentially reduced. In certain embodiments, the C9ORF72 mRNA variants preferentially reduced are variants containing intron 1. In certain embodiments, intron 1 contains a hexanucleotide repeat expansion. In certain embodiments, the hexanucleotide repeat expansion is associated with a C9ORF72 associated disease. In certain embodiments, the hexanucleotide repeat expansion is associated with a C9ORF72 hexanucleotide repeat expansion associated disease. In certain embodiments, the hexanucleotide repeat expansion comprises at least 30 GGGGCC repeats. In certain embodiments, the hexanucleotide repeat expansion is associated with nuclear foci. In certain embodiments, the methods described herein are useful for reducing C9ORF72 mRNA, C9ORF72 protein levels, and nuclear foci. Such reduction can occur in a time-dependent manner or in a dose-dependent manner.

Also provided are methods useful for preventing, treating, and ameliorating diseases, disorders, and conditions associated with C9ORF72. In certain embodiments, such diseases, disorders, and conditions associated with C9ORF72 are neurodegenerative diseases. In certain embodiments, the neurodegenerative disease is ALS, FTD, corticalbasal degeneration syndrome (CBD), atypical Parkinsonian syndrome, and olivopontocerellar degeneration (OPCD).

Such diseases, disorders, and conditions can have one or more risk factors, causes, or outcomes in common. Certain risk factors and causes for development of a neurodegenerative disease, and, in particular, ALS and FTD, include genetic predisposition and older age.

In certain embodiments, methods of treatment include administering a C9ORF72 specific inhibitor to an individual in need thereof. In certain embodiments, the C9ORF72 specific inhibitor is a nucleic acid. In certain embodiments, the nucleic acid is an antisense compound. In certain embodiments, the antisense compound is a single-stranded antisense oligonucleotide. In certain embodiments, the single-stranded antisense oligonucleotide is complementary to a C9ORF72 nucleic acid.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl group" (also 2'-MOE and 2'-OCH$_2$CH$_2$—OCH$_3$ and MOE) refers to an O-methoxyethyl modification of the 2' position of a furanosyl ring. A 2'-O-methoxyethyl modified sugar is a modified sugar.

"2'-MOE nucleoside" (also 2'-O-methoxyethyl nucleoside) means a nucleoside comprising a 2'-O-methoxyethyl group.

"5-methylcytosine" means a cytosine modified with a methyl group attached to the 5' position. A 5-methylcytosine is a modified nucleobase.

"About" means within ±7% of a value. For example, if it is stated, "the compounds affected at least about 70% inhibition of C9ORF72", it is implied that the C9ORF72 levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" or "ameliorate" or "ameliorating" refers to a lessening of at least one indicator, sign, or symptom of a disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds. Antisense mechanisms include, without limitation, RNase H mediated antisense; RNAi mechanisms, which utilize the RISC pathway and include, without limitation, siRNA, ssRNA and microRNA mechanisms; and occupancy based mechanisms, including, without limitation uniform modified oligonucleotides. Certain antisense compounds may act through more than one such mechanisms and/or through additional mechanisms.

"Antisense inhibition" means reduction of target nucleic acid levels or target protein levels in the presence of an antisense compound complementary to a target nucleic acid compared to target nucleic acid levels or target protein levels in the absence of the antisense compound Inhibition may by any means including RNase H degradation, such as with a gapmer, and steric blockage/occupancy based mechanisms, such as with a uniformly modified oligonucleotide.

"Antisense oligonucleotide" means a single-stranded oligonucleotide having a nucleobase sequence that permits hybridization to a corresponding segment of a target nucleic acid.

"Bicyclic sugar" means a furanosyl ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"C9ORF72 associated disease" means any disease associated with any C9ORF72 nucleic acid or expression product thereof. Such diseases may include a neurodegenerative disease. Such neurodegenerative diseases may include ALS and FTD.

"C9ORF72 hexanucleotide repeat expansion associated disease" means any disease associated with a C9ORF72 nucleic acid containing a hexanucleotide repeat expansion. In certain embodiments, the hexanucleotide repeat expansion may comprise GGGGCC, GGGGGG, GGGGGC, or GGGGCG repeated at least 30 times. Such diseases may include a neurodegenerative disease. Such neurodegenerative diseases may include ALS and FTD.

"C9ORF72 nucleic acid" means any nucleic acid encoding C9ORF72. For example, in certain embodiments, a C9ORF72 nucleic acid includes a DNA sequence encoding C9ORF72, an RNA sequence transcribed from DNA encoding C9ORF72 (including genomic DNA comprising introns and exons), and an mRNA sequence encoding C9ORF72. "C9ORF72 mRNA" means an mRNA encoding a C9ORF72 protein.

"C9ORF72 specific inhibitor" refers to any agent capable of specifically inhibiting the expression of C9ORF72 mRNA and/or C9ORF72 protein at the molecular level. For example, C9ORF72 specific inhibitors include nucleic acids (including antisense compounds), siRNAs, aptamers, antibodies, peptides, small molecules, and other agents capable of inhibiting the expression of C9ORF72 mRNA and/or C9ORF72 protein. Similarly, in certain embodiments, C9ORF72 specific inhibitors may affect other molecular processes in an animal.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of pharmaceutical agent sufficient to effectuate a desired physiological outcome in an individual in need of the pharmaceutical agent. The effective amount may vary among individuals depending on the health and physical condition of the individual to be treated, the taxonomic group of the individuals to be treated, the formulation of the composition, assessment of the individual's medical condition, and other relevant factors.

"Expression" means conversion of the information from a C9ORF72 gene into mRNA via transcription and then to protein via translation. Expression may result in a phenotypic manifestation of the C9ORF72 gene.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hexanucleotide repeat expansion" means a series of six bases (for example, GGGGCC, GGGGGG, GGGGCG, or GGGGGC) repeated at least twice. In certain embodiments, the hexanucleotide repeat expansion may be located in intron 1 of a C9ORF72 nucleic acid. In certain embodiments, a pathogenic hexanucleotide repeat expansion includes at least 30 repeats of GGGGCC, GGGGGG, GGGGCG, or GGGGGC in a C9ORF72 nucleic acid and is associated with disease. In certain embodiments, the repeats are consecutive. In certain embodiments, the repeats are interrupted by 1 or more nucleobases. In certain embodiments, a wild-type hexanucleotide repeat expansion includes 23 or fewer repeats of GGGGCC, GGGGGG, GGGGCG, or GGGGGC in a C9ORF72 nucleic acid. In certain embodiments, the repeats are consecutive. In certain embodiments, the repeats are interrupted by 1 or more nucleobases.

"Hybridization" means the annealing of complementary nucleic acid molecules. In certain embodiments, complementary nucleic acid molecules include an antisense compound and a target nucleic acid.

"Identifying an animal having a C9ORF72 associated disease" means identifying an animal having been diagnosed with a C9ORF72 associated disease or predisposed to develop a C9ORF72 associated disease. Individuals predisposed to develop a C9ORF72 associated disease include those having one or more risk factors for developing a C9ORF72 associated disease, including, having a personal or family history or genetic predisposition of one or more C9ORF72 associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting C9ORF72" means reducing expression of C9ORF72 mRNA and/or protein levels in the presence of a C9ORF72 specific inhibitor, including a C9ORF72 antisense oligonucleotide, as compared to expression of C9ORF72 mRNA and/or protein levels in the absence of a C9ORF72 specific inhibitor, such as a C9ORF72 antisense oligonucleotide.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising a modified internucleoside linkage, a modified sugar, or a modified nucleobase.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Peptide refers to polypeptides and proteins.

"Pharmaceutical agent" means the substance or substances in a pharmaceutical composition that provide a therapeutic benefit when administered to an individual. For example, in certain embodiments an antisense oligonucleotide targeted to C9ORF72 is a pharmaceutical agent.

"Pharmaceutical composition" means a mixture of substances suitable for administering to an individual. For example, a pharmaceutical composition may comprise one or more pharmaceutical agents and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage (P=S) is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" or "treating" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods for decreasing C9ORF72 mRNA and protein expression.

Certain embodiments provide methods for the treatment, prevention, or amelioration of diseases, disorders, and conditions associated with C9ORF72 in an individual in need thereof. Also contemplated are methods for the preparation of a medicament for the treatment, prevention, or amelioration of a disease, disorder, or condition associated with C9ORF72. C9ORF72 associated diseases, disorders, and conditions include neurodegenerative diseases. In certain embodiments, the neurodegenerative disease may be ALS or FTD. In certain embodiments, the neurodegenerative disease may be familial or sporadic.

Certain embodiments provide for the use of a C9ORF72 specific inhibitor for treating, preventing, or ameliorating a C9ORF72 associated disease. Certain embodiments provide for the use of a C9ORF72 specific inhibitor for treating, preventing, or ameliorating a C9ORF72 hexanucleotide repeat expansion associated disease. In certain embodiments, the hexanucleotide repeat expansion may comprise GGGGCC, GGGGGG, GGGGGC, or GGGGCG. In certain embodiments, C9ORF72 specific inhibitors are nucleic acids (including antisense compounds), peptides, antibodies, small molecules, and other agents capable of inhibiting the expression of C9ORF72 mRNA and/or C9ORF72 protein.

Described herein are methods comprising administering a C9ORF72 or C9ORF72 homolog specific inhibitor to an animal.

Described herein are methods comprising:
identifying an animal having a C9ORF72 associated disease; and
administering a C9ORF72 specific inhibitor.

In certain embodiments, the animal is a human.

In certain embodiments, the C9ORF72 specific inhibitor is any of an antisense compound, an aptamer, an antibody, a peptide, or a small molecule.

In certain embodiments, the antisense compound comprises a single-stranded antisense oligonucleotide complementary to a C9ORF72 nucleic acid.

In certain embodiments, the C9ORF72 nucleic acid is a human C9ORF72 nucleic acid.

In certain embodiments, the animal has a C9ORF72 associated disease.

In certain embodiments, the C9ORF72 associated disease is a C9ORF72 hexanucleotide repeat expansion associated disease.

In certain embodiments, the C9ORF72 associated disease is amyotrophic lateral sclerosis (ALS) or frontotemporal dementia (FTD).

In certain embodiments, the C9ORF72 hexanucleotide repeat expansion associated disease is amyotrophic lateral sclerosis (ALS) or frontotemporal dementia (FTD).

In certain embodiments, the amyotrophic lateral sclerosis (ALS) is familial ALS or sporadic ALS.

In certain embodiments, the single-stranded antisense oligonucleotide comprises at least one modification.

In certain embodiments, the single-stranded antisense oligonucleotide is specifically hybridizable to a human C9ORF72 nucleic acid.

In certain embodiments, the single-stranded antisense oligonucleotide is at least 75%, at least 80%, at least 85%, at least 90%, or at least 95% complementary to an equal length portion of a human C9ORF72 nucleic acid.

In certain embodiments, the single-stranded antisense oligonucleotide is 100% complementary to an equal length portion of a human C9ORF72 nucleic acid.

In certain embodiments, the single-stranded antisense oligonucleotide comprises at least one modified internucleoside linkage.

In certain embodiments, each internucleoside linkage of the single-stranded antisense oligonucleotide is a modified internucleoside linkage.

In certain embodiments, the modified internucleoside linkage is a phosphorothioate internucleoside linkage.

In certain embodiments, the single-stranded antisense oligonucleotide comprises at least one modified nucleoside.

In certain embodiments, the single-stranded antisense oligonucleotide comprises at least one modified nucleoside having a modified sugar.

In certain embodiments, the single-stranded antisense oligonucleotide comprises at least one modified nucleoside comprising a bicyclic sugar.

In certain embodiments, the bicyclic sugar comprises a 4' to 2' bridge selected from among: 4'-$(CH_2)_n$—O-2' bridge, wherein n is 1 or 2; and 4'-$CH_2$—O—$CH_2$-2'.

In certain embodiments, the bicyclic sugar comprises a 4'-$CH(CH_3)$—O-2' bridge.

In certain embodiments, at least one modified nucleoside having a modified sugar comprises a non-bicyclic 2'-modified modified sugar moiety.

In certain embodiments, the 2'-modified sugar moiety comprises a 2'-O-methoxyethyl group.

In certain embodiments, the 2'-modified sugar moiety comprises a 2'-O-methyl group.

In certain embodiments, the at least one modified nucleoside having a modified sugar comprises a sugar surrogate.

In certain embodiments, the sugar surrogate is a morpholino.

In certain embodiments, the sugar surrogate is a peptide nucleic acid.

In certain embodiments, each nucleoside is modified.

In certain embodiments, the single-stranded antisense oligonucleotide comprises at least one modified nucleobase.

In certain embodiments, the modified nucleobase is a 5'-methylcytosine.

In certain embodiments, the single-stranded antisense oligonucleotide comprises:
a gap segment consisting of linked deoxynucleosides;
a 5' wing segment consisting of linked nucleosides;
a 3' wing segment consisting of linked nucleosides;
wherein the gap segment is positioned immediately adjacent to and between the 5' wing segment and the 3' wing segment and wherein each nucleoside of each wing segment comprises a modified sugar.

In certain embodiments the single-stranded antisense oligonucleotide comprises:
a gap segment consisting of ten linked deoxynucleosides;
a 5' wing segment consisting of five linked nucleosides;
a 3' wing segment consisting of five linked nucleosides;
wherein the gap segment is positioned immediately adjacent and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the single-stranded antisense oligonucleotide consists of 15 linked nucleosides.

In certain embodiments, the single-stranded antisense oligonucleotide consists of 16 linked nucleosides.

In certain embodiments, the single-stranded antisense oligonucleotide consists of 17 linked nucleosides.

In certain embodiments, the single-stranded antisense oligonucleotide consists of 18 linked nucleosides.

In certain embodiments, the single-stranded antisense oligonucleotide consists of 19 linked nucleosides.

In certain embodiments, the single-stranded antisense oligonucleotide consists of 20 linked nucleosides.

In certain embodiments, the single-stranded antisense oligonucleotide consists of 21 linked nucleosides.

In certain embodiments, the single-stranded antisense oligonucleotide consists of 22 linked nucleosides.

In certain embodiments, the single-stranded antisense oligonucleotide consists of 23 linked nucleosides.

In certain embodiments, the single-stranded antisense oligonucleotide consists of 24 linked nucleosides.

In certain embodiments, the single-stranded antisense oligonucleotide consists of 25 linked nucleosides.

In certain embodiments, the single-stranded antisense oligonucleotide complementary to a C9ORF72 nucleic acid is complementary to any of an intron, an exon, a splice junction, an exon:exon junction, a repeat, the 3' UTR, or the 5' UTR of the C9ORF72 nucleic acid.

In certain embodiments, the intron is any of introns 1, intron 2, intron 3, intron 4, intron 5, intron 6, intron 7, intron 8, intron 9, or intron 10.

In certain embodiments, the exon is any of exon 1a, exon 1b, exon 1c, exon 1d, exon 1d, exon 2, exon 3, exon 4, exon 5, exon 6, exon 7, exon 8, exon 9, exon 10, or exon 11.

In certain embodiments, the repeat is a hexanucleotide repeat.

In certain embodiments, the hexanucleotide repeat is any of GGGGCC, GGGGGG, GGGGCG, or GGGGGC.

In certain embodiments, expression of C9ORF72 RNA is reduced.

In certain embodiments, expression of C9ORF72 RNA is reduced in a nucleus.

In certain embodiments, expression of C9ORF72 protein is reduced.

In certain embodiments, expression of C9ORF72 protein is reduced in a nucleus.

In certain embodiments, expression is reduced in any of fibroblasts, immortalized lymphoblasts, spinal motor neurons, purkinje and granular cells in the cerebellum, cortical neurons, astrocytes, or microglia.

In certain embodiments, expression of C9ORF72 isoform V1 RNA is reduced.

In certain embodiments, expression of C9ORF72 isoform V1 protein is reduced.

In certain embodiments, expression of C9ORF72 isoform V2 RNA is reduced.

In certain embodiments, expression of C9ORF72 isoform V2 protein is reduced.

In certain embodiments, expression of C9ORF72 isoform V3 RNA is reduced.

In certain embodiments, expression of C9ORF72 isoform V3 protein is reduced.

In certain embodiments, expression of C9ORF72 isoform V2 RNA and expression of C9ORF72 isoform V3 RNA is reduced and C9ORF72 isoform V1 RNA is not reduced.

In certain embodiments, expression of C9ORF72 isoform V2 protein and expression of C9ORF72 isoform V3 protein is reduced and C9ORF72 isoform V1 protein is not reduced.

In certain embodiments, C9ORF72 RNA foci are reduced.

In certain embodiments, C9ORF72 RNA foci are reduced in a nucleus.

In certain embodiments, compositions described herein are administered by parenteral administration.

In certain embodiments, the parenteral administration is any of injection or infusion. In certain embodiments, the parenteral administration is any of intrathecal administration or intracerebroventricular administration.

In certain embodiments, at least one symptom of a C9ORF72 associated disease is ameliorated or prevented.

In certain embodiments, at least one symptom of a C9ORF72 hexanucleotide repeat expansion associated disease is ameliorated or prevented.

In certain embodiments, progression of at least one symptom of a C9ORF72 associated disease is slowed.

In certain embodiments, progression of at least one symptom of a C9ORF72 hexanucleotide repeat expansion associated disease is slowed.

In certain embodiments, the at least one symptom is any of motor function, respiration, muscle weakness, fasciculation and cramping of muscles, difficulty in projecting the voice, shortness of breath, difficulty in breathing and swallowing, inappropriate social behavior, lack of empathy, distractibility, changes in food preferences, agitation, blunted emotions, neglect of personal hygiene, repetitive or compulsive behavior, and decreased energy and motivation.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a C9ORF72 nucleic acid is 12 to 30 subunits in length. In other words, such antisense compounds are from 12 to 30 linked subunits. In certain embodiments, the antisense compound is 8 to 80, 12 to 50, 15 to 30, 18 to 24, 19 to 22, or 20 linked subunits. In certain embodiments, the antisense compounds are 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In some embodiments the antisense compound is an antisense oligonucleotide, and the linked subunits are nucleosides.

In certain embodiments antisense oligonucleotides targeted to a C9ORF72 nucleic acid may be shortened or truncated. For example, a single subunit may be deleted from the 5' end (5' truncation), or alternatively from the 3' end (3' truncation). A shortened or truncated antisense compound targeted to a C9ORF72 nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a C9ORF72 nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH_2)_n$-O-2' bridge, where n=1 or n=2 and 4'-$CH_2$—O—$CH_2$-2'). Preferably, each distinct region comprises uniform sugar moieties. The wing-gap-wing motif is frequently described as "X—Y—Z", where "X" represents the length of the 5' wing region, "Y" represents the length of the gap region, and "Z" represents the length of the 3' wing region. As used herein, a gapmer described as "X—Y—Z" has a configuration such that the gap segment is positioned immediately adjacent to each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers described herein include, but are not limited to, for example 5-10-5, 5-10-4, 4-10-4, 4-10-3, 3-10-3, 2-10-2, 5-9-5, 5-9-4, 4-9-5, 5-8-5, 5-8-4, 4-8-5, 5-7-5, 4-7-5, 5-7-4, or 4-7-4.

In certain embodiments, the antisense compound has a "wingmer" motif, having a wing-gap or gap-wing configuration, i.e. an X—Y or Y—Z configuration as described above for the gapmer configuration. Thus, wingmer configurations described herein include, but are not limited to, for example 5-10, 8-4, 4-12, 12-4, 3-14, 16-2, 18-1, 10-3, 2-10, 1-10, 8-2, 2-13, 5-13, 5-8, or 6-8.

In certain embodiments, antisense compounds targeted to a C9ORF72 nucleic acid possess a 5-10-5 gapmer motif.

In certain embodiments, antisense compounds targeted to a C9ORF72 nucleic acid possess a 5-10-4 gapmer motif.

In certain embodiments, antisense compounds targeted to a C9ORF72 nucleic acid possess a 4-10-4 gapmer motif.

In certain embodiments, antisense compounds targeted to a C9ORF72 nucleic acid possess a 4-10-3 gapmer motif.

In certain embodiments, antisense compounds targeted to a C9ORF72 nucleic acid possess a 5-9-5 gapmer motif.

In certain embodiments, an antisense compound targeted to a C9ORF72 nucleic acid has a gap-narrowed motif. In certain embodiments, a gap-narrowed antisense oligonucleotide targeted to a C9ORF72 nucleic acid has a gap segment of 9, 8, 7, or 6 2'-deoxynucleotides positioned immediately adjacent to and between wing segments of 5, 4, 3, 2, or 1 chemically modified nucleosides. In certain embodiments, the chemical modification comprises a bicyclic sugar. In certain embodiments, the bicyclic sugar comprises a 4' to 2' bridge selected from among: 4'-(CH$_2$)$_n$—O-2' bridge, wherein n is 1 or 2; and 4'-CH$_2$—O—CH$_2$-2'. In certain embodiments, the bicyclic sugar is comprises a 4'-CH(CH$_3$)—O-2' bridge. In certain embodiments, the chemical modification comprises a non-bicyclic 2'-modified sugar moiety. In certain embodiments, the non-bicyclic 2'-modified sugar moiety comprises a 2'-O-methylethyl group or a 2'-O-methyl group.

In certain embodiments, an antisense compound targeted to a C9ORF72 nucleic acid is uniformly modified. In certain embodiments, the antisense compound comprises 12, 13, 14, 15, 16, 17, 18, 19, 20, 21, 22, 23, 24, or 25 nucleosides. In certain embodiments, each nucleoside is chemically modified. In certain embodiments, the chemical modification comprises a non-bicyclic 2'-modified sugar moiety. In certain embodiments, the 2'-modified sugar moiety comprises a 2'-O-methoxyethyl group. In certain embodiments, the 2'-modified sugar moiety comprises a 2'-O-methyl group. In certain embodiments, uniformly modified antisense compound may target C9ORF72, or any portion thereof, such as a hexanucleotide repeat expansion. In certain embodiments, targeting the hexanucleotide repeat expansion with a uniformly modified antisense compound reduced the repeat RNA by blocking the interaction with RNA binding proteins. In certain embodiments, this results in the toxic RNA being absent from foci and being degraded instead.

Target Nucleic Acids, Target Regions and Nucleotide Sequences

Nucleotide sequences that encode C9ORF72 include, without limitation, the following: the complement of GENBANK Accession No. NM_001256054.1 (incorporated herein as SEQ ID NO: 1), GENBANK Accession No. NT_008413.18 truncated from nucleobase 27535000 to 27565000 (incorporated herein as SEQ ID NO: 2), GENBANK Accession No. BQ068108.1 (incorporated herein as SEQ ID NO: 3), GENBANK Accession No. NM_018325.3 (incorporated herein as SEQ ID NO: 4), GENBANK Accession No. DN993522.1 (incorporated herein as SEQ ID NO: 5), GENBANK Accession No. NM_145005.5 (incorporated herein as SEQ ID NO: 6), GENBANK Accession No. DB079375.1 (incorporated herein as SEQ ID NO: 7), GENBANK Accession No. BU194591.1 (incorporated herein as SEQ ID NO: 8), Sequence Identifier 4141_014_A (incorporated herein as SEQ ID NO: 9), and Sequence Identifier 4008_73_A (incorporated herein as SEQ ID NO: 10).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for C9ORF72 can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within a target region. In certain embodiments, reductions in C9ORF72 mRNA levels are indicative of inhibition of C9ORF72 expression. Reductions in levels of a C9ORF72 protein are also indicative of inhibition of target mRNA expression. Reduction in the presence of expanded C9ORF72 RNA foci are indicative of inhibition of C9ORF72 expression. Further, phenotypic changes are indicative of inhibition of C9ORF72 expression. For example, improved motor function and respiration may be indicative of inhibition of C9ORF72 expression.

Hybridization

In some embodiments, hybridization occurs between an antisense compound disclosed herein and a C9ORF72 nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a C9ORF72 nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a C9ORF72 nucleic acid).

Non-complementary nucleobases between an antisense compound and a C9ORF72 nucleic acid may be tolerated provided that the antisense compound remains able to specifically hybridize to a target nucleic acid. Moreover, an antisense compound may hybridize over one or more segments of a C9ORF72 nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a C9ORF72 nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a C9ORF72 nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a C9ORF72 nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a C9ORF72 nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a C9ORF72 nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—$N(R_l)$—$(CH_2)_2$—$N(R_m)(R_n)$, where each $R_l$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-($CH_2$)—O-2' (LNA); 4'-($CH_2$)—S-2'; 4'-($CH_2$)$_2$—O-2' (ENA); 4'-CH($CH_3$)—O-2' and 4'-CH($CH_2OCH_3$)—O-2' (and analogs thereof see U.S. Pat. No. 7,399,845, issued on Jul. 15, 2008); 4'-C($CH_3$)($CH_3$)—O-2' (and analogs thereof see published International Application WO/2009/006478, published Jan. 8, 2009); 4'-$CH_2$—N($OCH_3$)-2' (and analogs thereof see published International Application WO/2008/150729, published Dec. 11, 2008); 4'-$CH_2$—O—N($CH_3$)-2' (see published U.S. Patent Application US2004-0171570, published Sep. 2, 2004); 4'-$CH_2$—N(R)—O-2', wherein R is H, $C_1$-$C_{12}$ alkyl, or a protecting group (see U.S. Pat. No. 7,427,672, issued on Sep. 23, 2008); 4'-$CH_2$—C(H)($CH_3$)-2' (see Chattopadhyaya et al., J. Org. Chem., 2009, 74, 118-134); and 4'-$CH_2$—C(=$CH_2$)-2' (and analogs thereof see published International Application WO 2008/154401, published on Dec. 8, 2008).

Further reports related to bicyclic nucleosides can also be found in published literature (see for example: Singh et al., Chem. Commun., 1998, 4, 455-456; Koshkin et al., Tetrahedron, 1998, 54, 3607-3630; Wahlestedt et al., Proc. Natl. Acad. Sci. U.S.A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 2007, 129(26) 8362-8379; Elayadi et al., Curr. Opinion Invest. Drugs, 2001, 2, 558-561; Braasch et al., Chem. Biol., 2001, 8, 1-7; and Orum et al., Curr. Opinion Mol. Ther., 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C($R_a$)($R_b$)]$_n$—, —C($R_a$)=C($R_b$)—, —C($R_a$)=N—, —C(=O)—, —C(=N$R_a$)—, —C(=S)—, —O—, —Si($R_a$)$_2$—, —S(=O)$_x$—, and —N($R_a$)—;
wherein:
x is 0, 1, or 2;
n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(=O)—H), substituted acyl, CN, sulfonyl (S(=O)$_2$-$J_1$), or sulfoxyl (S(=O)-$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(=O)—H), substituted acyl, a heterocycle radical, a substituted heterocycle radical, $C_1$-$C_{12}$ aminoalkyl, substituted $C_1$-$C_{12}$ aminoalkyl or a protecting group.

In certain embodiments, the bridge of a bicyclic sugar moiety is —[C($R_a$)($R_b$)]$_n$—, —[C($R_a$)($R_b$)]$_n$—O—, —C($R_aR_b$)—N(R)—O— or —C($R_aR_b$)—O—N(R)—. In certain embodiments, the bridge is 4'-$CH_2$-2', 4'-($CH_2$)$_2$-2', 4'-($CH_2$)$_3$-2', 4'-$CH_2$—O-2', 4'-($CH_2$)$_2$—O-2', 4'-$CH_2$—O—N(R)-2' and 4'-$CH_2$—N(R)—O-2'- wherein each R is, independently, H, a protecting group or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., Nucleic Acids Research, 2003, 21, 6365-6372).

In certain embodiments, bicyclic nucleosides include, but are not limited to, (A) α-L-methyleneoxy (4'-$CH_2$—O-2') BNA, (B) β-D-methyleneoxy (4'-$CH_2$—O-2') BNA, (C) ethyleneoxy (4'-($CH_2$)$_2$—O-2') BNA, (D) aminooxy (4'-$CH_2$—O—N(R)-2') BNA, (E) oxyamino (4'-$CH_2$—N(R)—O-2') BNA, and (F) methyl(methyleneoxy) (4'-CH($CH_3$)—O-2') BNA, (G) methylene-thio (4'-$CH_2$—S-2') BNA, (H) methylene-amino (4'-$CH_2$—N(R)-2') BNA, (I) methyl carbocyclic (4'-$CH_2$—CH($CH_3$)-2') BNA, and (J) propylene carbocyclic (4'-($CH_2$)$_3$-2') BNA as depicted below.

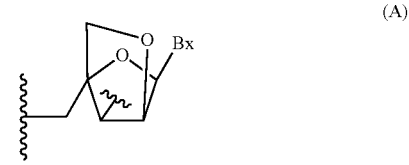

(A)

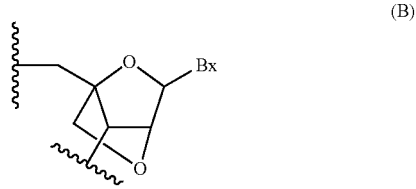

(B)

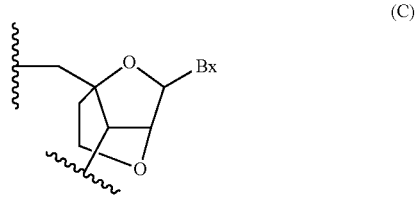

(C)

(D) 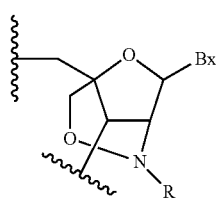

(E) 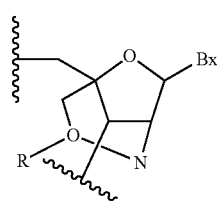

(F) 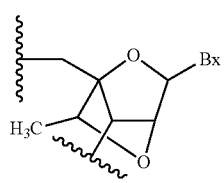

(G) 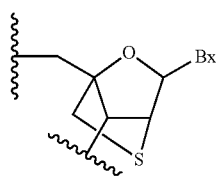

(H) 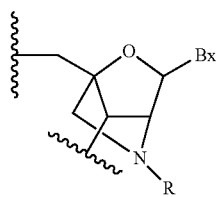

(I) 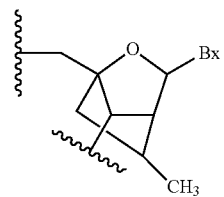

(J) 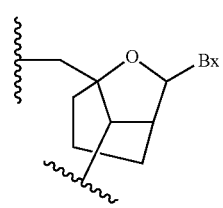

wherein Bx is the base moiety and R is independently H, a protecting group or $C_1$-$C_{12}$ alkyl.

In certain embodiments, bicyclic nucleosides are provided having Formula I:

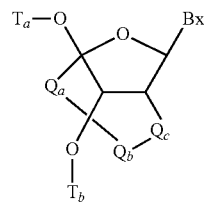

wherein:
Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

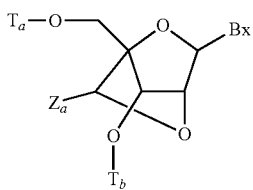

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC$(=X)$NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

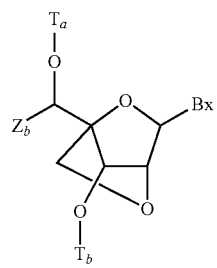

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

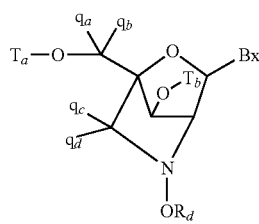

IV wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

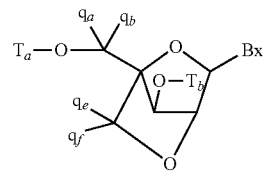

V wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);
$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

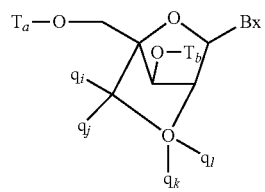

VI wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-($CH_2$)$_3$-2' bridge and the alkenyl analog bridge 4'-CH=CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nF$, $O(CH_2)_nONH_2$, $OCH_2C(=O)N(H)CH_3$, and $O(CH_2)_nON[(CH_2)_nCH_3]_2$, where n and m are from 1 to about 10. Other 2'- substituent groups can also be selected from: $C_1$-$C_{12}$ alkyl, substituted alkyl, alkenyl, alkynyl, alkaryl, aralkyl, O-alkaryl or O-aralkyl, SH, $SCH_3$, OCN, Cl, Br, CN, F, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

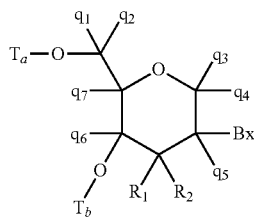

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and (p is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2' substituents, such as allyl, amino, azido, thio, 0-allyl, O—$C_1$-$C_{10}$ alkyl, —$OCF_3$, O—$(CH_2)_2$—O—$CH_3$, 2'-$O(CH_2)_2SCH_3$, O—$(CH_2)_2$—O—N($R_m$)($R_n$), or O—$CH_2$—C(=O)—N($R_m$)($R_n$), where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-$OCH_3$" or "2'-O-methyl" each refers to a nucleoside comprising a sugar comprising an —$OCH_3$ group at the 2' position of the sugar ring.

As used herein, "MOE" or "2'-MOE" or "2'-$OCH_2CH_2OCH_3$" or "2'-O-methoxyethyl" each refers to a nucleoside comprising a sugar comprising a —$OCH_2CH_2OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH$_3$)—O-2') bridging group. In certain embodiments, the (4'-CH(CH$_3$)—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a C9ORF72 nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a C9ORF72 nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of C9ORF72 nucleic acids can be tested in vitro in a variety of cell types. Cell types used for such analyses are available from commercial vendors (e.g. American Type Culture Collection, Manassas, Va.; Zen-Bio, Inc., Research Triangle Park, NC; Clonetics Corporation, Walkersville, Md.) and are cultured according to the vendor's instructions using commercially available reagents (e.g. Invitrogen Life Technologies, Carlsbad, Calif.). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, Calif.). Antisense oligonucleotides are mixed with LIPOFECTIN in OPTI-MEM 1 (Invitrogen, Carlsbad, Calif.) to achieve the desired final concentration of antisense oligonucleotide and a LIPOFECTIN concentration that typically ranges 2 to 12 ug/mL per 100 nM antisense oligonucleotide.

Another reagent used to introduce antisense oligonucleotides into cultured cells includes LIPOFECTAMINE (Invitrogen, Carlsbad, Calif.). Antisense oligonucleotide is mixed with LIPOFECTAMINE in OPTI-MEM 1 reduced serum medium (Invitrogen, Carlsbad, Calif.) to achieve the desired concentration of antisense oligonucleotide and a LIPOFECTAMINE concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL Reagent (Invitrogen, Carlsbad, Calif.) according to the manufacturer's recommended protocols.

Analysis of Inhibition of Target Levels or Expression

Inhibition of levels or expression of a C9ORF72 nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art.

Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, Calif.). Cyclophilin A expression is quantified by real time PCR, by being run simultaneously with the target, multiplexing, or separately. Total RNA is quantified using RIBOGREEN RNA quantification reagent (Invetrogen, Inc. Eugene, Oreg.). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a C9ORF72 nucleic acid. Methods for designing real-time PCR probes and primers are well known in the art, and may include the use of software such as PRIMER EXPRESS Software (Applied Biosystems, Foster City, Calif.).

Analysis of Protein Levels

Antisense inhibition of C9ORF72 nucleic acids can be assessed by measuring C9ORF72 protein levels. Protein levels of C9ORF72 can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of mouse, rat, monkey, and human C9ORF72 are commercially available.

In Vivo Testing of Antisense Compounds

Antisense compounds, for example, antisense oligonucleotides, are tested in animals to assess their ability to inhibit expression of C9ORF72 and produce phenotypic changes, such as, improved motor function and respiration. In certain embodiments, motor function is measured by rotarod, grip strength, pole climb, open field performance, balance beam, hindpaw footprint testing in the animal. In certain embodiments, respiration is measured by whole body plethysmograph, invasive resistance, and compliance measurements in the animal. Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in C9ORF72 nucleic acid expression are measured.

Targeting C9ORF72

Antisense oligonucleotides described herein may hybridize to a C9ORF72 nucleic acid in any stage of RNA processing. For example, described herein are antisense oligonucleotides that are complementary to a pre-mRNA or a mature mRNA. Additionally, antisense oligonucleotides described herein may hybridize to any element of a C9ORF72 nucleic acid. For example, described herein are antisense oligonucleotides that are complementary to an exon, an intron, the 5' UTR, the 3' UTR, a repeat region, a hexanucleotide repeat expansion, a splice junction, an exon: exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10 of a C9ORF72 nucleic acid.

In certain embodiments, antisense oligonucleotides described herein hybridize to all variants of C9ORF72. In certain embodiments, the antisense oligonucleotides described herein selectively hybridize to certain variants of C9ORF72. In certain embodiments, the antisense oligonucleotides described herein selectively hybridize to variants of C9ORF72 containing a hexanucleotide repeat expansion. In certain embodiments, such variants of C9ORF72 containing a hexanucleotide repeat expansion include SEQ ID NO: 1-3 and 6-10. In certain embodiments, such hexanucleotide repeat expansion comprises at least 30 repeats of any of GGGGCC, GGGGGG, GGGGGC, or GGGGCG.

In certain embodiments, the antisense oligonucleotides described herein inhibit expression of all variants of C9ORF72. In certain embodiments, the antisense oligonucleotides described herein inhibit expression of all variants of C9ORF72 equally. In certain embodiments, the antisense oligonucleotides described herein preferentially inhibit expression of certain variants of C9ORF72. In certain embodiments, the antisense oligonucleotides described herein preferentially inhibit expression of variants of C9ORF72 containing a hexanucleotide repeat expansion. In certain embodiments, such variants of C9ORF72 containing a hexanucleotide repeat expansion include SEQ ID NO: 1-3 and 6-10. In certain embodiments, such hexanucleotide repeat expansion comprises at least 30 repeats of any of GGGGCC, GGGGGG, GGGGGC, or GGGGCG. In certain embodiments, the hexanucleotide repeat expansion forms nuclear foci. In certain embodiments, antisense oligonucleotides described herein are useful for reducing nuclear foci. Nuclear foci may be reduced in terms of percent of cells with foci as well as number of foci per cell.

Based on earlier studies directed to repeat expansions, it is not possible to predict if antisense oligonucleotides targeting C9ORF72 outside of the hexanucleotide repeat expansion would successfully inhibit expression of C9ORF72 for two reasons. First, the C9ORF72 repeat expansion is located in an intron and it is not known if the RNA in the foci contains only the repeats or also the flanking intronic sequence. For example, an earlier study on myotonic dystrophy type 2 (DM2), which is a disease caused by a CCTG expansion mutation in intron 1 of the ZNF9 gene, determined that large DM2 expansions did not prevent allele-specific pre-mRNA splicing, nuclear export of the transcripts, or steady-state mRNA or protein levels. The study further demonstrated that the ribonuclear inclusions found associated with the disease are enriched for the CCUG expansion, but not the flanking intronic sequences. These data suggest that the downstream molecular effects of the DM2 mutation may be triggered by the accumulation of CCUG repeat tract alone. Therefore, this study implies that targeting the CCUG repeat expansion alone would lead to amelioration of the disease, since targeting the flanking sequences, especially the region downstream of the repeat expansion, would not affect the formation of ribonuclear inclusions (Margolis et al. Hum. Mol. Genet., 2006, 15:1808-1815). Second, it is not known how fast intron 1 of C9ORF72, which contains the repeats, is excised and accumulates in foci. Thus, it is not possible to predict if targeting the pre-mRNA would result in elimination of the repeat RNA and foci.

C9ORF72 Features

Antisense oligonucleotides described herein may hybridize to any C9ORF72 variant at any state of processing within any element of the C9ORF72 gene. For example, antisense oligonucleotides described herein may hybridize to an exon, an intron, the 5' UTR, the 3' UTR, a repeat region, a hexanucleotide repeat expansion, a splice junction, an exon: exon splice junction, an exonic splicing silencer (ESS), an exonic splicing enhancer (ESE), exon 1a, exon 1b, exon 1c, exon 1d, exon 1e, exon 2, exon 3, exon 4, exon 5, exon 6, exon 7, exon 8, exon 9, exon 10, exon 11, intron 1, intron 2, intron 3, intron 4, intron 5, intron 6, intron 7, intron 8, intron 9, or intron 10. For example, antisense oligonucleotides may target any of the exons characterized below in Tables 1-5 for the various C9ORF72 variants described below. Antisense oligonucleotides described herein may also target variants not characterized below and such variants are characterized in GENBANK. Moreover, antisense oligonucleotides described herein may also target elements other than exons and such elements are characterized in GENBANK.

TABLE 1

Functional Segments for NM_001256054.1 (SEQ ID NO: 1)

| Exon Number | mRNA start site | mRNA stop site | Start site in reference to SEQ ID NO: 2 | Stop site in reference to SEQ ID NO: 2 |
|---|---|---|---|---|
| exon 1C | 1 | 158 | 1137 | 1294 |
| exon 2 | 159 | 646 | 7839 | 8326 |
| exon 3 | 647 | 706 | 9413 | 9472 |
| exon 4 | 707 | 802 | 12527 | 12622 |
| exon 5 | 803 | 867 | 13354 | 13418 |
| exon 6 | 868 | 940 | 14704 | 14776 |
| exon 7 | 941 | 1057 | 16396 | 16512 |
| exon 8 | 1058 | 1293 | 18207 | 18442 |
| exon 9 | 1294 | 1351 | 24296 | 24353 |
| exon 10 | 1352 | 1461 | 26337 | 26446 |
| exon 11 | 1462 | 3339 | 26581 | 28458 |

TABLE 2

Functional Segments for NM_018325.3 (SEQ ID NO: 4)

| Exon Number | mRNA start site | mRNA stop site | Start site in reference to SEQ ID NO: 2 | Stop site in reference to SEQ ID NO: 2 |
|---|---|---|---|---|
| exon 1B | 1 | 63 | 1510 | 1572 |
| exon 2 | 64 | 551 | 7839 | 8326 |
| exon 3 | 552 | 611 | 9413 | 9472 |
| exon 4 | 612 | 707 | 12527 | 12622 |
| exon 5 | 708 | 772 | 13354 | 13418 |
| exon 6 | 773 | 845 | 14704 | 14776 |
| exon 7 | 846 | 962 | 16396 | 16512 |
| exon 8 | 963 | 1198 | 18207 | 18442 |
| exon 9 | 1199 | 1256 | 24296 | 24353 |
| exon 10 | 1257 | 1366 | 26337 | 26446 |
| exon 11 | 1367 | 3244 | 26581 | 28458 |

TABLE 3

Functional Segments for NM_145005.5 (SEQ ID NO: 6)

| Exon Number | mRNA start site | mRNA stop site | Start site in reference to SEQ ID NO: 2 | Stop site in reference to SEQ ID NO: 2 |
|---|---|---|---|---|
| exon 1A | 1 | 80 | 1137 | 1216 |
| exon 2 | 81 | 568 | 7839 | 8326 |
| exon 3 | 569 | 628 | 9413 | 9472 |
| exon 4 | 629 | 724 | 12527 | 12622 |
| exon 5B (exon 5 into intron 5) | 725 | 1871 | 13354 | 14500 |

TABLE 4

Functional Segments for DB079375.1 (SEQ ID NO: 7)

| Exon Number | mRNA start site | mRNA stop site | Start site in reference to SEQ ID NO: 2 | Stop site in reference to SEQ ID NO: 2 |
|---|---|---|---|---|
| exon 1E | 1 | 35 | 1135 | 1169 |
| exon 2 | 36 | 524 | 7839 | 8326 |
| exon 3 (EST ends before end of full exon) | 525 | 562 | 9413 | 9450 |

TABLE 5

Functional Segments for BU194591.1 (SEQ ID NO: 8)

| Exon Number | mRNA start site | mRNA stop site | Start site in reference to SEQ ID NO: 2 | Stop site in reference to SEQ ID NO: 2 |
|---|---|---|---|---|
| exon 1D | 1 | 36 | 1241 | 1279 |
| exon 2 | 37 | 524 | 7839 | 8326 |
| exon 3 | 525 | 584 | 9413 | 9472 |
| exon 4 | 585 | 680 | 12527 | 12622 |
| exon 5B (exon 5 into intron 5) | 681 | 798 | 13354 | 13465 |

Certain Indications

In certain embodiments, provided herein are methods of treating an individual comprising administering one or more pharmaceutical compositions described herein. In certain embodiments, the individual has a neurodegenerative disease. In certain embodiments, the individual is at risk for developing a neurodegenerative disease, including, but not limited to, ALS or FTD. In certain embodiments, the individual has been identified as having a C9ORF72 associated disease. In certain embodiments, the individual has been identified as having a C9ORF72 hexanucleotide repeat expansion associated disease. In certain embodiments, provided herein are methods for prophylactically reducing C9ORF72 expression in an individual. Certain embodiments include treating an individual in need thereof by administering to an individual a therapeutically effective amount of an antisense compound targeted to a C9ORF72 nucleic acid.

In one embodiment, administration of a therapeutically effective amount of an antisense compound targeted to a C9ORF72 nucleic acid is accompanied by monitoring of C9ORF72 levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a C9ORF72 nucleic acid results in reduction of C9ORF72 expression by at least 15, 20, 25, 30, 35, 40, 45, 50, 55, 60, 65, 70, 75, 80, 85, 90, 95 or 99%, or a range defined by any two of these values. In certain embodiments, administration of an antisense compound targeted to a C9ORF72 nucleic acid results in improved motor function and respiration in an animal. In certain embodiments, administration of a C9ORF72 antisense compound improves motor function and respiration by at least 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to C9ORF72 are used for the preparation of a medicament for treating a patient suffering or susceptible to a neurodegenerative disease including ALS and FTD.

Certain Combination Therapies

In certain embodiments, one or more pharmaceutical compositions described herein are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions described herein. In certain embodiments, one or more pharmaceutical compositions described herein are co-administered with another pharmaceutical agent to treat an undesired effect of that other pharmaceutical agent. In certain embodiments, one or more pharmaceutical compositions described herein are co-administered with another pharmaceutical agent to produce a combinational effect. In certain embodiments, one or more pharmaceutical compositions described herein are co-administered with another pharmaceutical agent to produce a synergistic effect.

In certain embodiments, one or more pharmaceutical compositions described herein and one or more other pharmaceutical agents are administered at the same time. In certain embodiments, one or more pharmaceutical compositions described herein and one or more other pharmaceutical agents are administered at different times. In certain embodiments, one or more pharmaceutical compositions described herein and one or more other pharmaceutical agents are prepared together in a single formulation. In certain embodiments, one or more pharmaceutical compositions described herein and one or more other pharmaceutical agents are prepared separately.

In certain embodiments, pharmaceutical agents that may be co-administered with a pharmaceutical composition described herein include Riluzole (Rilutek), Lioresal (Lioresal), and Dexpramipexole.

In certain embodiments, pharmaceutical agents that may be co-administered with a C9ORF72 specific inhibitor described herein include, but are not limited to, an additional C9ORF72 inhibitor. In certain embodiments, the co-administered pharmaceutical agent is administered prior to administration of a pharmaceutical composition described herein. In certain embodiments, the co-administered pharmaceutical agent is administered following administration of a pharmaceutical composition described herein. In certain embodiments the co-administered pharmaceutical agent is administered at the same time as a pharmaceutical composition described herein. In certain embodiments the dose of a co-administered pharmaceutical agent is the same as the dose that would be administered if the co-administered pharmaceutical agent was administered alone. In certain embodiments the dose of a co-administered pharmaceutical agent is lower than the dose that would be administered if the co-administered pharmaceutical agent was administered alone. In certain embodiments the dose of a co-administered pharmaceutical agent is greater than the dose that would be administered if the co-administered pharmaceutical agent was administered alone.

In certain embodiments, the co-administration of a second compound enhances the effect of a first compound, such that co-administration of the compounds results in an effect that is greater than the effect of administering the first compound alone. In other embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human C9ORF72 in HepG2 Cells

Antisense oligonucleotides were designed targeting a C9ORF72 nucleic acid and were tested for their effects on C9ORF72 mRNA in vitro. The antisense oligonucleotides were tested in a series of experiments that had similar culture conditions. The results for each experiment are presented in separate tables shown below. Cultured HepG2 cells at a density of 20,000 cells per well were transfected using electroporation with 7,000 nM antisense oligonucleotide. After a treatment period of approximately 24 hours, RNA was isolated from the cells and C9ORF72 mRNA levels were measured by quantitative real-time PCR. Human primer probe set RTS3750 (forward sequence TGTGACA-GTTGGAATGCAGTGA, designated herein as SEQ ID NO: 15; reverse sequence GCCACTTAAAGCAATCTCT-GTCTTG, designated herein as SEQ ID NO: 16; probe sequence TCGACTCTTTGCCCACCGCCA, designated herein as SEQ ID NO: 17) was used to measure mRNA levels. C9ORF72 mRNA levels were adjusted according to total RNA content, as measured by RIBOGREEN®. Results are presented as percent inhibition of C9ORF72, relative to untreated control cells.

The antisense oligonucleotides in Tables 6-8 were designed as 5-10-5 MOE gapmers. The gapmers are 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages throughout each gapmer are phosphorothioate linkages. All cytosine residues throughout each gapmer are 5-methylcytosines. "Start site" indicates the 5'-most nucleoside to which the antisense oligonucleotide is targeted in the human gene sequence. "Stop site" indicates the 3'-most nucleoside to which the antisense oligonucleotide is targeted human gene sequence. Each antisense oligonucleotide listed in Tables 6-7 is targeted to the either human C9ORF72 mRNA sequence, designated herein as SEQ ID NO: 1 (GENBANK Accession No. NM_001256054.1) or the human C9ORF72 genomic sequence, designated herein as SEQ ID NO: 2 (the complement of GENBANK Accession No. NT_008413.18 truncated from nucleosides 27535000 to 27565000), or both. 'n/a' indicates that the antisense oligonucleotide did not target that particular gene sequence. The antisense oligonucleotides of Table 8 are targeted to either SEQ ID NO: 3 (GENBANK Accession No. BQ068108.1) or SEQ ID NO: 4 (GENBANK Accession No. NM_018325.3).

TABLE 6

| ISIS No | % inhibition |
|---|---|
| 576816 | 78 |
| 576860 | 79 |

TABLE 7

| ISIS No | % inhibition |
|---|---|
| 576974 | 56 |

TABLE 8

| ISIS No | % inhibition |
|---|---|
| 576816 | 90 |
| 577061 | 28 |
| 577065 | 0 |
| 577083 | 70 |

Example 2: Dose-Dependent Antisense Inhibition of Human C9ORF72 in HepG2 Cells

Antisense oligonucleotides from the study described above exhibiting significant in vitro inhibition of C9ORF72 mRNA were selected and tested at various doses in HepG2 cells. The antisense oligonucleotides were tested in a series of experiments that had similar culture conditions. The results for each experiment are presented in separate tables shown below. Cells were plated at a density of 20,000 cells per well and transfected using electroporation with 82.3 nM, 246.9 nM, 740.7 nM, 2,222.2 nM, 6,666.7 nM, or 20,000 nM concentrations of antisense oligonucleotide. After a treatment period of approximately 16 hours, RNA was isolated from the cells and C9ORF72 mRNA levels were measured by quantitative real-time PCR. Human C9ORF72 primer probe set RTS3750 was used to measure mRNA levels. C9ORF72 mRNA levels were adjusted according to total RNA content, as measured by RIBOGREEN®. Results are presented as percent inhibition of C9ORF72, relative to untreated control cells.

The half maximal inhibitory concentration ($IC_{50}$) of each oligonucleotide is also presented in Tables 9-10. As illustrated, C9ORF72 mRNA levels were reduced in a dose-dependent manner in the antisense oligonucleotide treated cells.

TABLE 9

| ISIS No | 82.3 nM | 246.9 nM | 740.7 nM | 2222.2 nM | 6666.7 nM | 20000.0 nM | $IC_{50}$ (µM) |
|---|---|---|---|---|---|---|---|
| 576816 | 5 | 23 | 49 | 76 | 91 | 96 | 0.9 |
| 576860 | 9 | 24 | 54 | 70 | 83 | 87 | 1.0 |

TABLE 10

| ISIS No | 82.3 nM | 246.9 nM | 740.7 nM | 2222.2 nM | 6666.7 nM | 20000.0 nM | $IC_{50}$ (µM) |
|---|---|---|---|---|---|---|---|
| 576974 | 25 | 45 | 65 | 70 | 65 | 78 | 0.5 |
| 576816 | 18 | 36 | 53 | 82 | 91 | 95 | 0.6 |
| 577083 | 0 | 0 | 24 | 50 | 73 | 74 | 3.0 |

Example 3: Dose-Dependent Antisense Inhibition of Human C9ORF72 in HepG2 Cells

Antisense oligonucleotides from the study described above exhibiting significant in vitro inhibition of C9ORF72 mRNA were selected and tested at various doses in HepG2 cells. The antisense oligonucleotides were tested in a series of experiments that had similar culture conditions. The results for each experiment are presented in separate tables shown below. Cells were plated at a density of 20,000 cells per well and transfected using electroporation with 246.9 nM, 740.7 nM, 2,222.2 nM, 6,666.7 nM, or 20,000 nM concentrations of antisense oligonucleotide. After a treatment period of approximately 16 hours, RNA was isolated from the cells and C9ORF72 total mRNA levels, as well as mRNA levels of the exon 1 transcript, were measured by quantitative real-time PCR. Human C9ORF72 primer probe set RTS3750 was used to measure total C9ORF72 mRNA levels. Primer probe set RTS3905 (forward sequence GGGTCTAGCAAGAGCAGGTG, designated herein as SEQ ID NO: 18; reverse sequence GTCTTGGCAACA-GCTGGAGAT, designated herein as SEQ ID NO: 19; probe sequence TGATGTCGACTCTTTGCCCACCGC, designated herein as SEQ ID NO: 20) was used to measure exon 1 message transcript. C9ORF72 mRNA levels were adjusted according to total RNA content, as measured by RIBOGREEN®. Results are presented as percent inhibition of C9ORF72, relative to untreated control cells.

The half maximal inhibitory concentration ($IC_{50}$) of each oligonucleotide is also presented in Tables 11 and 12. As illustrated, C9ORF72 mRNA levels were reduced in a dose-dependent manner in the antisense oligonucleotide treated cells. 'n.d.' indicates that there is no data for that particular dose.

TABLE 11

% inhibition of total C9ORF72 mRNA levels

| ISIS No | 246.9 nM | 740.7 nM | 2222.2 nM | 6666.7 nM | 20000.0 nM | $IC_{50}$ (µM) |
|---|---|---|---|---|---|---|
| 576816 | 29 | 53 | 84 | 90 | 92 | 0.60 |
| 576860 | 25 | 53 | 72 | 86 | 85 | 0.80 |
| 576974 | 36 | 49 | 64 | 65 | 68 | 0.95 |
| 577061 | 0 | 3 | 0 | 4 | 0 | >20.00 |
| 577065 | 7 | 0 | 1 | 6 | 0 | >20.00 |
| 577083 | 0 | 19 | 55 | 71 | 75 | 3.35 |

TABLE 12

% inhibition of C9ORF72 exon 1 mRNA levels

| ISIS No | 246.9 nM | 740.7 nM | 2222.2 nM | 6666.7 nM | 20000.0 nM | $IC_{50}$ (µM) |
|---|---|---|---|---|---|---|
| 576816 | 45 | 78 | 93 | n.d. | n.d. | 0.26 |
| 576860 | 43 | 36 | 71 | 95 | 91 | 0.66 |
| 577061 | 8 | 36 | 70 | 67 | 76 | 2.03 |
| 577065 | 20 | 55 | 67 | 82 | 62 | 1.06 |
| 577083 | 30 | 43 | 85 | 88 | 92 | 0.71 |

Example 4: Effect of Antisense Inhibition of Human C9ORF72 in ALS Patient Primary Fibroblasts Antisense oligonucleotides, from the studies described above and targeting various regions of the C9ORF72 gene (SEQ ID NO: 2), were tested in ALS patient primary fibroblasts. The target location of each antisense oligonucleotide is specified in Table 13 below. As observed from the Table, several of the antisense oligonucleotides target intron 1 and, therefore, the pre-mRNA sequence of C9ORF72. Intron 1 contains a hexanucleotide repeat (GGGGCC), which is expanded to at least 30 repeats in a pathogenic cell (Renton et al., Neuron, 2011, 72, 257-268).

TABLE 13

Location of antisense oligonucleotides targeting SEQ ID NO: 1

| ISIS No | Location |
|---|---|
| 577061 | Intron 1 |
| 577065 | Intron 1 |
| 577083 | Intron 1 |
| 576816 | Exon 2 |
| 576860 | Intron 5 |
| 576974 | Exon 11 |

The effect of treatment of antisense oligonucleotide targeting C9ORF72 was assessed in primary fibroblasts derived from ALS patients. Primary fibroblasts derived from skin biopsy of a human ALS patient (Dr John Ravits lab) were plated in DMEM medium supplemented with 20% fetal bovine serum. The cells were treated with the antisense oligonucleotides targeting C9ORF72 at 25 nM concentration for 4 hrs. A set of cells was treated with a control oligonucleotide (ASO control), with no known human target, and served as a negative control. After 24 hrs of transfection, the cells were harvested in TriZol reagent for RNA quantification, or were fixed with 4% paraformaldehyde for in situ hybridization.

RNA Analysis

The cells were harvested and levels of certain mRNA variants of C9ORF72, as well as total C9ORF72 mRNA were analyzed. The mRNA variants measured were SEQ ID NO: 1 (variant 3) and SEQ ID NO: 6 (variant 2). As presented in Tables 1 and 3 listed above, SEQ ID NOs 1 and 6 encode portions of the C9ORF72 sequence that include intron 1. Because intron 1 includes the hexanucleotide repeat, reducing mRNA levels of these variants are therapeutic in pathogenic cells (cells containing hexanucleotide repeat expansions of more than 30 repeats). Certain other mRNA variants do not include the hexanucleotide repeat; for example, SEQ ID NO: 4. Therefore, it is possible to preferentially inhibit certain C9ORF72 variants by designing antisense oligonucleotides to target certain regions of the target C9ORF72 nucleic acid, such as, for example intron 1.

The levels of SEQ ID NO: 1 and 6 (variants 3 and 2, respectively) were measured in combination by primer probe set RTS3905, which targets exon 1. The level of total C9orf72 mRNA was measured by primer probe set RTS3750, which targets exon 2. The data is presented in Table 14. As compared to PBS control, Isis 577061 and Isis 577065 (each targeting Intron 1) reduced expression of variant 2/3 RNA by over 90% and reduced total RNA by 18% and 8%, respectively. Isis 577083 (targeting intron 1), Isis 576816 (targeting exon 2), Isis 576860 (targeting exon 5), and Isis 576974 (targeting exon 11) achieved between 75% and 96% inhibition of variant 2/3 RNA expression and total RNA expression. The ASO control did not significantly inhibit RNA levels, as expected.

TABLE 14

Percent inhibition, compared to the PBS control, of RNA levels of C9ORF72 in primary fibroblasts

| Oligo ID | Location | Variant 2/3 RNA | Total RNA |
|---|---|---|---|
| ASO control | n/a | 13 | 3 |
| 577061 | Intron 1 | 95 | 18 |
| 577065 | Intron 1 | 96 | 8 |
| 577083 | Intron 1 | 89 | 81 |
| 576816 | Exon 2 | 96 | 95 |
| 576860 | Intron 5 | 81 | 75 |
| 576974 | Exon 11 | 85 | 77 |

Analysis of C9ORF72 RNA Foci

In recent years, intracellular accumulation of expanded nucleotide repeats as RNA foci in the nucleus of affected cells has emerged as an important disease mechanism in frontotemporal dementia and ALS patients (DeJesus-Hernandez, M. et al., Neuron. 2011. 72: 245-56). C9ORF72 nuclear foci were detected using FISH with (5'TYE563-CCCCGGCCCCGGCCCC) (SEQ ID NO: 23) LNA probe (Exiqon). The data for the percentage of cells with foci is presented in Table 15. The results indicate that antisense oligonucleotides targeting C9ORF72 RNA decreased the percentage of cells containing C9ORF72 RNA foci.

Single and multiple RNA foci are detected in patient fibroblasts. The numbers of cells with single or multiple foci from fibroblasts that were treated with ISIS 576816 or the ASO control were counted. The data is presented in Table 16, and indicates that the antisense oligonucleotide targeting C9ORF72 reduced the number of foci per cell compared to the ASO control.

TABLE 15

Percent of primary fibroblasts with foci

|  | % cells |
|---|---|
| PBS | 37 |
| ASO control | 38 |
| 577061 | 9 |
| 577065 | 6 |
| 577083 | 6 |
| 576816 | 9 |
| 576860 | 12 |
| 576974 | 12 |

TABLE 16

Number of cells with single of multiple foci

| Foci# | 576816-treated | ASO Control |
|---|---|---|
| 0 | 82 | 66 |
| 1 | 14 | 10 |
| 2 | 2 | 9 |
| 3 | 2 | 5 |
| 4 | 0 | 5 |
| 5 | 0 | 2 |
| 6 | 0 | 0 |
| 7 | 0 | 0 |
| 8 | 0 | 2 |
| 9 | 0 | 0 |
| 10+ | 0 | 1 |

Example 5: Effect of siRNA Inhibition of Human C9ORF72 in ALS Patient Primary Fibroblasts siRNA targeting C9ORF72 and control siRNA targeting GAPDH were obtained from Thermo Scientific Dharmacon (On-Target plus Smartpool). The effect of treatment of siRNA in ALS patient fibroblasts was assessed.

Primary fibroblasts derived from a skin biopsy of a human ALS patients were plated in DMEM medium supplemented with 20% fetal bovine serum. The cells were treated with the siRNA targeting C9ORF72 at 40 nM concentration for 4 hrs. A set of cells was also treated with siRNA targeting GAPDH at 40 nM concentration for 4 hrs and served as the control. After transfection for 24 hrs, the cells were harvested in TriZol reagent for RNA quantification, or were fixed with 4% paraformaldehyde for in situ hybridization.

Total C9ORF72 RNA levels were measured using a primer set (Forward: TCCTGTAATGGAACTGCTTTCA, designated herein as SEQ ID NO: 21; Reverse: GGTATCT-GCTTCATCCAGCTTT, designated herein as SEQ ID NO: 22). siRNA treatment resulted in 73% inhibition of total C9ORF72 RNA levels compared to the control.

C9ORF72 nuclear foci were detected using FISH with (5'TYE563-CCCCGGCCCCGGCCCC) (SEQ ID NO: 23) LNA probe (Exiqon). The data is presented in Table 17. The results indicate that siRNA treatment against C9ORF72 does not reduce nuclear foci in the fibroblasts compared to the control.

TABLE 17

Percentage of cells with foci

|  | % cells |
|---|---|
| siRNA-GAPDH | 28 |
| siRNA-C9ORF72 | 31 |

Example 6: In Vivo Rodent Inhibition and Tolerability with Treatment of C9ORF72 Antisense Oligonucleotides In order to assess the tolerability of inhibition of C9orf72 expression in vivo, antisense oligonucleotides targeting a murine C9orf72 nucleic acid were designed and assessed in mouse and rat models.

ISIS 571883 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are phosphorothioate linkages. All cytosine residues throughout the gapmer are 5-methylcytosines. ISIS 571883 has a target start site of nucleoside 33704 on the murine C9ORF72 genomic sequence, designated herein as SEQ ID NO: 11 (the complement of GENBANK Accession No. NT_166289.1 truncated from nucleosides 3587000 to 3625000).

ISIS 603538 was designed as a 5-10-5 MOE gapmer, 20 nucleosides in length, wherein the central gap segment comprises ten 2'-deoxynucleosides and is flanked by wing segments on both the 5' end and on the 3' end comprising five nucleosides each. Each nucleoside in the 5' wing segment and each nucleoside in the 3' wing segment has a MOE modification. The internucleoside linkages are either phosphorothioate linkages or phosphate ester linkages (Gs Ao Co Co Gs Cs Ts Ts Gs As Gs Ts Ts Ts Gs Co Co Ao Cs A; wherein 's' denotes a phosphorothioate internucleoside linkage, 'o' denotes a phosphate ester linkage; and A, G, C, T denote the relevant nucleosides). All cytosine residues throughout the gapmer are 5-methylcytosines. ISIS 603538 has a target start site of nucleoside 2872 on the rat C9ORF72 mRNA sequence, designated herein as SEQ ID NO: 12 (GENBANK Accession No. NM_001007702.1).

Mouse Experiment 1

Groups of 4 C57BL/6 mice each were injected with 50 µg, 100 µg, 300 µg, 500 µg, or 700 µg of ISIS 571883 administered via an intracerebroventricular bolus injection. A control group of four C57/BL6 mice were similarly treated with PBS. Animals were anesthetized with 3% isofluorane and placed in a stereotactic frame. After sterilizing the surgical site, each mouse was injected −0.2 mm anterioposterior from the bregma na d 3 mm dorsoventral to the bregma with the above-mentioned doses of ISIS 571883 using a Hamilton syringe. The incision was closed with sutures. The mice were allowed to recover for 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely five sections using a mouse brain matrix.

RNA Analysis

RNA was extracted from a 2-3 mm brain section posterior to the injection site, from brain frontal cortex and from the lumbar section of the spinal cord tissue for analysis of C9orf72 mRNA expression. C9orf72 mRNA expression was measured by RT-PCR. The data is presented in Table 18. The results indicate that treatment with increasing doses of ISIS 571883 resulted in dose-dependent inhibition of C9orf72 mRNA expression.

The induction of the microglial marker AIF-1 as a measure of CNS toxicity was also assessed. The data is presented in Table 19. The results indicate that treatment with increasing doses of ISIS 571883 did not result in significant increases in AIF-1 mRNA expression. Hence, the injection of ISIS 571883 was deemed tolerable in this model.

TABLE 18

Percentage inhibition of C9orf72 mRNA expression compared to the PBS control

| Dose (µg) | Posterior brain | Cortex | Spinal cord |
|---|---|---|---|
| 50 | 22 | 8 | 46 |
| 100 | 22 | 12 | 47 |
| 300 | 55 | 47 | 67 |
| 500 | 61 | 56 | 78 |
| 700 | 65 | 65 | 79 |

TABLE 19

Percentage expression of AIF-1 mRNA expression compared to the PBS control

| Dose (µg) | Posterior brain | Spinal cord |
|---|---|---|
| 50 | 102 | 89 |
| 100 | 105 | 111 |
| 300 | 107 | 98 |
| 500 | 131 | 124 |
| 700 | 122 | 116 |

Mouse Experiment 2

Groups of 4 C57BL/6 mice each were injected with 500 µg of ISIS 571883 administered via an intracerebroventricular bolus injection in a procedure similar to that described above. A control group of four C57/BL6 mice were similarly treated with PBS. The mice were tested at regular time points after ICV administration.

Behavior Analysis

Two standard assays to assess motor behavior were employed; the rotarod assay and grip strength assay. In case of the rotarod assays, the time of latency to fall was measured. The data for the assays is presented in Tables 20 and 21. The results indicate that there were no significant changes in the motor behavior of the mice as a result of antisense inhibition of ISIS 571883 or due to the ICV injection. Hence, antisense inhibition of C9orf72 was deemed tolerable in this model.

TABLE 20

Latency to fall (sec) in the rotarod assay

| Weeks after injection | PBS | ISIS 571883 |
|---|---|---|
| 0 | 66 | 66 |
| 4 | 91 | 70 |
| 8 | 94 | 84 |

TABLE 21

Mean hindlimb grip strength (g) in the grip strength assay

| Weeks after injection | PBS | ISIS 571883 |
|---|---|---|
| 0 | 57 | 63 |
| 1 | 65 | 51 |
| 2 | 51 | 52 |
| 3 | 51 | 51 |
| 4 | 59 | 72 |
| 5 | 60 | 64 |
| 6 | 61 | 72 |
| 7 | 67 | 68 |
| 8 | 66 | 70 |
| 9 | 63 | 61 |
| 10 | 48 | 46 |

Rat Experiment

Groups of 4 Sprague-Dawley rats each were injected with 700 µg, 1,000 µg, or 3,000 µg of ISIS 603538 administered via an intrathecal bolus injection. A control group of four Sprague-Dawley rats were similarly treated with PBS. Animals were anesthetized with 3% isofluorane and placed in a stereotactic frame. After sterilizing the surgical site, each rat was injected with 30 µL of ASO solution administered via 8 cm intrathecal catheter 2 cm into the spinal canal with a 50 µL flush. The rats were allowed to recover for 4 weeks, after which animals were euthanized according to a humane protocol approved by the Institutional Animal Care and Use Committee.

RNA Analysis

RNA was extracted from a 2-3 mm brain section posterior to the injection site, from brain frontal cortex, and from the cervical and lumbar sections of the spinal cord tissue for analysis of C9orf72 mRNA expression. C9orf72 mRNA expression was measured by RT-PCR. The data is presented in Table 22. The results indicate that treatment with increasing doses of ISIS 603538 resulted in dose-dependent inhibition of C9orf72 mRNA expression.

The induction of the microglial marker AIF-1 as a measure of CNS toxicity was also assessed. The data is presented in Table 23. The results indicate that treatment with increasing doses of ISIS 603538 did not result in significant increases in AIF-1 mRNA expression. Hence, the injection of ISIS 603538 was deemed tolerable in this model.

TABLE 22

Percentage inhibition of C9orf72 mRNA expression compared to the PBS control

| Dose (µg) | Brain (1 mm section) | Cortex | Spinal cord (lumbar) | Spinal cord (cervical) |
|---|---|---|---|---|
| 700 | 21 | 4 | 86 | 74 |
| 1000 | 53 | 49 | 88 | 82 |
| 3000 | 64 | 62 | 88 | 80 |

TABLE 23

Percentage expression of AIF-1 mRNA expression compared to the PBS control

| Dose (μg) | Brain (1 mm section) | Cortex | Spinal cord (lumbar) | Spinal cord (cervical) |
|---|---|---|---|---|
| 700 | 97 | 119 | 98 | 89 |
| 1000 | 105 | 113 | 122 | 96 |
| 3000 | 109 | 141 | 156 | 115 |

Body Weight Analysis

Body weights of the rats were measured at regular time point intervals. The data is presented in Table 24. The results indicate that treatment with increasing doses of ISIS 603538 did not have any significant changes in the body weights of the rats.

TABLE 24

Body weights of the rats (% initial body weight)

| | Dose (μg) | Week 1 | Week 2 | Week 3 | Week 4 | Week 5 |
|---|---|---|---|---|---|---|
| PBS | | 100 | 94 | 103 | 105 | 109 |
| ISIS 603538 | 700 | 100 | 94 | 98 | 103 | 107 |
| | 1000 | 100 | 95 | 97 | 101 | 103 |
| | 3000 | 100 | 92 | 98 | 102 | 105 |

What is claimed is:

1. A method of reducing the percent of cells with foci and/or reducing the number of foci per cell in an animal identified as having foci comprising administering to the animal a therapeutically effective amount of a compound comprising a modified oligonucleotide consisting of 12 to 30 linked nucleosides, wherein the modified oligonucleotide is at least 90% complementary to a C9ORF72 nucleic acid, and wherein the modified oligonucleotide is not complementary to a C9ORF72 hexanucleotide repeat expansion; and thereby reducing the percent of cells with foci and/or reducing the number of foci per cell.

2. The method of claim 1, wherein the level of C9ORF72 mRNA is reduced, and optionally level of C9ORF72 protein is reduced.

3. The method of claim 1, wherein the animal has a disease selected from amyotrophic lateral sclerosis (ALS), frontotemporal dementia (FTD), corticalbasal degeneration syndrome (CBD), atypical Parkinsonian syndrome, or olivopontocerebellar degeneration (OPCD).

4. The method of claim 1, wherein the nucleobase sequence of the modified oligonucleotide is 100% complementary to an equal length portion of a C9ORF72 nucleic acid.

5. The method of claim 4, wherein the C9ORF72 nucleic acid has the nucleobase sequence of any of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, or SEQ ID NO: 10.

6. The method of claim 5, wherein the modified oligonucleotide is a single-stranded oligonucleotide.

7. The method of claim 6, wherein the single-stranded modified oligonucleotide is a gapmer.

8. The method of claim 6, wherein at least one internucleoside linkage of the modified oligonucleotide is a modified internucleoside linkage.

9. The method of claim 8, wherein each internucleoside linkage of the modified oligonucleotide is a modified internucleoside linkage.

10. The method of claim 8, wherein the modified internucleoside linkage is a phosphorothioate internucleoside linkage.

11. The method of claim 9, wherein the modified internucleoside linkage is a phosphorothioate internucleoside linkage.

12. The method of claim 6, wherein at least one nucleoside of the modified oligonucleotide comprises a modified nucleobase.

13. The method of claim 12, wherein the modified nucleobase is a 5-methylcytosine.

14. The method of claim 6, wherein at least one nucleoside of the modified oligonucleotide comprises a modified sugar.

15. The method of claim 14, wherein each nucleoside of the modified oligonucleotide comprises a modified sugar.

16. The method of claim 14, wherein the oligonucleotide comprises at least one modified nucleoside comprising a bicyclic sugar.

17. The method of claim 16, wherein the bicyclic sugar comprises a chemical bridge between the 4' and 2' positions of the sugar, wherein the chemical bridge is selected from: 4'-CH(R)—O-2' and 4'-(CH$_2$)$_2$—O-2', wherein each R is independently C$_1$-C$_6$ alkyl or C$_1$-C$_6$ alkoxy.

18. The method of claim 17, wherein the chemical bridge is 4'-CH(R)—O-2' and wherein R is methyl.

19. The method of claim 17, wherein the chemical bridge is 4'-CH(R)—O-2' and wherein R is H.

20. The method of claim 17, wherein the chemical bridge is 4'-CH(R)—O-2' and wherein R is CH$_2$—O—CH$_3$.

21. The method of claim 15, wherein the modified sugar is a bicyclic sugar comprising a chemical bridge between the 4' and 2' positions of the sugar, wherein the chemical bridge is selected from: 4'-CH(R)—O-2' and 4'-(CH$_2$)$_2$—O-2', wherein each R is independently C$_1$-C$_6$ alkyl or C$_1$-C$_6$ alkoxy.

22. The method of claim 21, wherein the chemical bridge is 4'-CH(R)—O-2' and wherein R is methyl.

23. The method of claim 21, wherein the chemical bridge is 4'-CH(R)—O-2' and wherein R is H.

24. The method of claim 21, wherein the chemical bridge is 4'-CH(R)—O-2' and wherein R is CH$_2$—O—CH$_3$.

25. The method of claim 14, wherein the oligonucleotide comprises at least one modified nucleoside comprising a 2'-O-methoxyethyl group.

26. The method of claim 15, wherein the oligonucleotide comprises at least one modified nucleoside comprising a 2'-O-methoxyethyl group.

27. The method of claim 1, wherein the animal has a C9ORF72 associated disease.

28. The method of claim 27, wherein the C9ORF72 associated disease is a C9ORF72 hexanucleotide repeat expansion associated disease.

\* \* \* \* \*